US008815558B2

(12) United States Patent
Frost et al.

(10) Patent No.: US 8,815,558 B2
(45) Date of Patent: Aug. 26, 2014

(54) HUMAN CHONDROITINASE GLYCOPROTEIN (CHASEGP), PROCESS FOR PREPARING THE SAME, AND PHARMACEUTICAL COMPOSITIONS COMPRISING THEREOF

(75) Inventors: Gregory I. Frost, Del Mar, CA (US); Anirban Kundu, San Diego, CA (US); Louis H. Bookbinder, San Diego, CA (US)

(73) Assignee: Halozyme, Inc., San Diego, CA (US)

( * ) Notice: Subject to any disclaimer, the term of this patent is extended or adjusted under 35 U.S.C. 154(b) by 114 days.

(21) Appl. No.: 12/475,221

(22) Filed: May 29, 2009

(65) Prior Publication Data
US 2010/0015698 A1 Jan. 21, 2010

Related U.S. Application Data

(62) Division of application No. 10/539,110, filed as application No. PCT/US03/40090 on Dec. 15, 2003, now Pat. No. 7,544,499.

(60) Provisional application No. 60/433,532, filed on Dec. 16, 2002.

(51) Int. Cl.
*C12N 9/24* (2006.01)
*C12P 21/06* (2006.01)
*C12N 15/00* (2006.01)
*C12N 1/20* (2006.01)
*C12N 5/00* (2006.01)
*C07H 21/04* (2006.01)

(52) U.S. Cl.
USPC .... 435/200; 435/69.1; 435/320.1; 435/252.3; 435/325; 536/23.2

(58) Field of Classification Search
None
See application file for complete search history.

(56) References Cited

U.S. PATENT DOCUMENTS

| 3,536,809 | A | 10/1970 | Applezweig | 424/435 |
|---|---|---|---|---|
| 3,598,123 | A | 8/1971 | Zaffaroni | 424/435 |
| 3,630,200 | A | 12/1971 | Higuchi | 424/427 |
| 3,845,770 | A | 11/1974 | Theeuwes et al. | 424/427 |
| 3,916,899 | A | 11/1975 | Theeuwes et al. | 424/424 |
| 4,008,719 | A | 2/1977 | Theeuwes et al. | 424/427 |
| 4,522,811 | A | 6/1985 | Eppstein et al. | 514/2 |
| 4,687,610 | A | 8/1987 | Vassilatos | 264/211.14 |
| 4,769,027 | A | 9/1988 | Baker et al. | 424/493 |
| 4,952,496 | A | 8/1990 | Studier et al. | 435/91.41 |
| 4,980,286 | A | 12/1990 | Morgan et al. | 435/371 |
| 5,059,595 | A | 10/1991 | Le Grazie | 424/468 |
| 5,073,543 | A | 12/1991 | Marshall et al. | 514/21 |
| 5,120,548 | A | 6/1992 | McClelland et al. | 424/473 |
| 5,215,899 | A | 6/1993 | Dattagupta | 435/6 |
| 5,354,566 | A | 10/1994 | Addesso et al. | 426/9 |
| 5,496,718 | A | 3/1996 | Hashimoto et al. | |
| 5,591,767 | A | 1/1997 | Mohr et al. | 514/413 |
| 5,639,476 | A | 6/1997 | Oshlack et al. | 424/468 |
| 5,674,533 | A | 10/1997 | Santus et al. | 424/493 |
| 5,733,566 | A | 3/1998 | Lewis | 424/426 |
| 5,763,205 | A | 6/1998 | Hashimoto et al. | |
| 5,773,277 | A | 6/1998 | Hashimoto et al. | |
| 6,001,630 | A | 12/1999 | Ichikawa et al. | |
| 6,184,023 | B1 | 2/2001 | Hashimoto et al. | |
| 7,544,499 | B2 | 6/2009 | Frost et al. | 435/200 |
| 2006/0104968 | A1 | 5/2006 | Bookbinder et al. | |
| 2009/0123367 | A1 | 5/2009 | Bookbinder et al. | |
| 2009/0181013 | A1 | 7/2009 | Bookbinder et al. | |
| 2009/0181032 | A1 | 7/2009 | Bookbinder et al. | |
| 2009/0214505 | A1 | 8/2009 | Bookbinder et al. | |
| 2009/0253175 | A1 | 10/2009 | Bookbinder et al. | |
| 2009/0304665 | A1 | 12/2009 | Frost et al. | |
| 2009/0311237 | A1 | 12/2009 | Frost et al. | |
| 2010/0003237 | A1 | 1/2010 | Keller et al. | |
| 2010/0003238 | A1 | 1/2010 | Frost et al. | |
| 2010/0074885 | A1 | 3/2010 | Schiff et al. | |
| 2010/0143457 | A1 | 6/2010 | Wei et al. | |
| 2010/0184845 | A1 | 7/2010 | Frost et al. | |

(Continued)

FOREIGN PATENT DOCUMENTS

| JP | 06153947 | 3/1994 |
|---|---|---|
| WO | WO 88/09810 | 12/1988 |

(Continued)

OTHER PUBLICATIONS

Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Branden et al., "Prediction, Engineering and Design of Protein Structures," Introductions to Protein Structure, Gerald Publishing Inc. p. 247, 1991.
Csoka et al., "Expression Analysis of Six Paralogous Human Hyaluronidase genes clustered on Chromosomes 3p21 and 7q31", Genomics 60(3):356-61, 1999.
Database GenBank, US National Library Library of Medicine (Bethesda, MD, USA) No. P19678 Gardel et al., Feb. 1991.

(Continued)

Primary Examiner — Iqbal H Chowdhury
(74) Attorney, Agent, or Firm — McKenna Long & Aldridge LLP; Stephanie Seidman; Karen G. Potter

(57) ABSTRACT

The invention relates to the discovery of novel Chondroitinase Glycoproteins (CHASEGPs), methods of manufacture, and potential uses in conditions where removal of chondroitin sulfates may be of therapeutic benefit. Chondroitinase Glycoproteins require both a substantial portion of the catalytic domain of the CHASEGP polypeptide and asparagine-linked glycosylation for optimal chondroitinase activity. The invention also includes carboxy-terminal deletion variants of CHASEGP that result in secreted variants of the protein to facilitate manufacture of a recombinant CHASEGP. Further described are suitable formulations of a substantially purified recombinant CHASEGP glycoprotein derived from a eukaryotic cell that generate the proper glycosylation required for its optimal activity. CHASEGP is useful for the degradation of glycosaminoglycans and chondroitin sulfate proteoglycans under clinical conditions where their removal is of therapeutic value.

14 Claims, No Drawings

(56) References Cited

U.S. PATENT DOCUMENTS

| | | |
|---|---|---|
| 2010/0284995 A1 | 11/2010 | Bookbinder et al. |
| 2011/0008309 A1 | 1/2011 | Bookbinder et al. |
| 2011/0053247 A1 | 3/2011 | Baker et al. |
| 2011/0152359 A1 | 6/2011 | Bookbinder et al. |

FOREIGN PATENT DOCUMENTS

| | | | |
|---|---|---|---|
| WO | WO 89/10134 | | 11/1989 |
| WO | WO 90/11364 | | 10/1990 |
| WO | WO 92/06180 | | 4/1992 |
| WO | WO 92/16640 | | 10/1992 |
| WO | WO 92/20316 | | 11/1992 |
| WO | WO 92/22635 | | 12/1992 |
| WO | WO 93/14188 | | 7/1993 |
| WO | WO 93/20221 | | 10/1993 |
| WO | WO 94/08598 | | 4/1994 |
| WO | WO 99/32619 | | 7/1999 |
| WO | WO 01/29058 | | 11/2001 |
| WO | WO 2004/028479 | | 4/2004 |
| WO | WO 2004-028479 | * | 4/2004 |
| WO | WO 2004/058147 | | 7/2004 |

OTHER PUBLICATIONS

DataBase GenBank, US National Library of Medicine (Bethesda, MD, USA) No. AF009010 Csoka et al., Oct. 1999.

DataBase GenBank, US National Library of Medicine (Bethesda, MD, USA) No. AK014599 Carninci et al., Nov. 1999.

DataBase GenBank, US National Library of Medicine (Bethesda, MD, USA) No. Q9D660 Carninci et al. Jun. 2001.

Database GenBank, US National Library of Medicine (Bethesda, MD, USA) No. Q9UL99, Csoka et al., May 2000.

Database GenBank, US National Library of Medicine (Bethesda, MD, USA) No. Q9Y6T9, Wilson et al., Nov. 1999.

Fiszer-Szafarz et al., "Human hyaluronidases: Electrophoretic multiple forms in somatic tissues and body fluids. Evidence for conserved hyaluronidase potential N-glycosylation sites in different mammalian species" Journal of Biochemical and Biophysical Methods, 45(2): 103-116 (2000).

Gacesa et al., "Effect of ionic strength and serum on the activity profile of bone testicular hyaluronidase", Biochem. Soc. Trans 7(5):1287-9, 1979.

Gold, "Purification and Properties of Hyaluronidase from Human Liver", J. Biochem. 205:69-74, 1982.

Hiyama et al., "Crystallization and Some Properties of Chondroitinase from *Arthrobacter aurescens*", J. Biol. Chem., 250(5):1824-1828, 1975.

Hiyama et al., "The Mode of Action of Two Chondroitinase-AC Preparations of Different Origin", J. Biochem (Tokyo) 80(6):1201-7, 1976.

Michelacci et al., "A Comparative Study Between a Chondroitinase B and a Chondroitinase AC from *Flavobacterium heparinum*: Isolation of a Chondroitinase AC-susceptible dodecasaccharide from Chondroitin sulphate B", J. Biochem 151(1):121-9, 1975.

Michelacci et al., "Isolation and Partial Characterization of an Induced Chondroitinase B from *Flavobacterium heparinum*", Biochem. Biophys. Res. Commun. 56(4):973-80, 1974.

Seffernick et al., "Melamine Deaminase and Atrazine Chlorohydrolase: 98 Percent Identical but Funtionally Different," Journal of Bacteriology, 183(8):2405-2410 (2001).

Suzuki et al., "Formation of Three Types of Disulfated Disaccharides from Chondroitin Sulfates by Chondroitinase Digestion", J. Biol. Chem. 243(7):1543-1550, 1968.

Whisstock et al., "Prediction of protein function from protein sequence and structure," Quarterly Review of Biophysics, 36(3): 307-340 (2003).

Witkowski et al., "Conversion of a beta-ketoacyl synthease to a malonyl decarboxylase by replacement of the active-site cysteine with glutamine," Biochemestry 38(36): 11643-50 (1999).

Yamagata et al., "Purification and Properties of Bacterial Chondroitinases and Chondrosulfatases", J. Biol. Chem. 243(7):1523-1535, 1968.

European Search Report from corresponding application EP 03814054.7.

International Search Report of corresponding international application PCT/US2003/40090.

Adams et al., "The c-myc oncogene driven by immunoglobulin enhancers induces lymphoid malignancy in transgenic mice," Nature 318:533-538 (1985).

Alexander et al., "Expression of the c-myc oncogene under control of an immunoglobulin enhancer in E mu-myc transgenic mice," Mol. Cell Biol. 7:1436-1444 (1987).

Altschul, S., "Basic local alignment search tool," J. Molec. Biol. 215(3):403-410 (1990).

Ashwell, G. and J. Harford, "Carbohydrate-specific receptors of the liver," Ann. Rev. Biochem. 51:531-554 (1982).

Benton, W. and R. Davis, "Screening lambdagt recombinant clones by hybridization to single plaques in situ," Science 196:180-182 (1977).

Bernoist, C. and P. Chambon, "In vivo sequence requirements of the SV40 early promotor region," Nature 290:304-310 (1981).

Bernstein et al., "Role for a bidentate ribonuclease in the initiation step of RNA interference," Nature 409:363-366 (2001).

Bitter et al., "Expression and secretion vectors for yeast," Methods in Enzymol 153:516-544 (1987).

Boesen et al., "Circumvention of chemotherapy-induced myelosuppression by transfer of the mdr1 gene," Biotherapy 6:291-302 (1994).

Bonner, W. and E. Cantey, "Colorimetric method for determination of serum hyaluronidase activity," Clin. Chim. Acta 13:746-752 (1966).

Bout et al., "Lung gene therapy: in vivo adenovirus-mediated gene transfer to rhesus monkey airway epithelium," Human Gene Therapy 5:3-10 (1994).

Bradbury, et al., "Chondroitinase ABC promotes functional recovery after spinal cord injury," Nature 416(6881):636-640 (2002).

Brinster et al., "Regulation of metallothionein—thymidine kinase fusion plasmids injected into mouse eggs," Nature 296:39-42 (1982).

Callewaert et al., "Ultrasensitive profiling and sequencing of N-linked oligosaccharides using standard DNA-sequencing equipment," Glycobiology 11:275-281 (2001).

Capecchi, M., "Altering the genome by homologous recombination," Science 244:1288-1292 (1989).

Carrillo et al., "The multiple-sequence alignment problem in biology," SIAM J Applied Math 48:1073-1082 (1988).

Certified English language translation of item EZ, Maeyama et al., "Chondroitinase AC—a unique illegible structure of ABC," Seikagaku 57:1189 (1985).

Certified English language translation of item FJ, Miyazono et al., "A structural analysis of the sugar chain (II)," Seikagaku 61:1023 (1989).

Chica et al. "Semi-rational approaches to engineering enzyme activity: combining the benefits of directed evolution and rational design," Curr Opin Biotechnol 16(4):378-384 (2005).

Chuang, C. and E. Meyerowitz, "Specific and heritable genetic interference by double-stranded RNA in *Arabidopsis thaliana*," Proc. Natl. Acad. Sci. USA 97:4985-4990 (2000).

Cline, M., "Perspectives for gene therapy: inserting new genetic information into mammalian cells by physical techniques and viral vectors," Pharmac. Ther. 29:69-92 (1985).

Clowes et al., "Long-term biological response of injured rat carotid artery seeded with smooth muscle cells expressing retrovirally introduced human genes," J. Clin. Invest. 93:644-651 (1994).

Colbere-Garapin et al., "A new dominant hybrid selective marker for higher eukaryotic cells," J Mol Biol 150:1-14 (1981).

Cole, G. and C. McCabe, "Identification of a developmentally regulated keratan sulfate proteoglycan that inhibits cell adhesion and neurite outgrowth," Neuron 7(6):1007-1018 (1991).

Cotten et al., "Receptor-mediated transport of DNA into eukaryotic cells," Meth. Enzymol. 217:618-644 (1993).

Cummings, R., "Use of lectins in analysis of glycoconjugates," Methods in Enzymol. 230:66-86 (1994).

Davies et al., "Regeneration of adult axons in white matter tracts of the central nervous system," Nature 390:680-683 (1997).

De Salegui et al., "A Comparison of Serum and Testicular Hyaluronidase," Arch. Biochem. Biophys. 121:548-554 (1967).

(56) References Cited

OTHER PUBLICATIONS

Deboer et al., "The tac promoter: a functional hybrid derived from the trp and lac promoters," Proc. Natl. Acad. Sci. USA 80:21-25 (1983).
Devereux et al, "A comprehensive set of sequence analysis programs for the VAX," Nucleic Acids Research 12:387-395 (1984).
Dexter et al., "Conditions controlling the proliferation of haemopoietic stem cells in vitro," J. Cell Physiol. 91(3):335-344 (1977).
Dillon, N., "Regulating gene expression in gene therapy," TIBTECH 11(5):167-173 (1993).
Dodet, B., "Commercial prospects for gene therapy," TIBTECH 11(5):182-189 (1993).
Dorfman, A. and M. Ott, "A turbidimetric method for the assay of hyaluronidase," J. Biol. Chem. 172:367-375 (1948).
Dzau et al., "Gene therapy for a cardiovascular disease," TIBTECH 11(5):205-210 (1993).
Elbashir et al., "Duplexes of 21-nucleotide RNAs mediate RNA interference in cultured mammalian cells," Nature 41(1):494-498 (2001).
Elbashir et al., "RNA interference is mediated by 21- and 22-nucleotide RNAs," Genes Dev. 15:188-200 (2001).
Findeis et al., "Targeted delivery of DNA for gene therapy via receptors," TIBTECH 11(5):202-205 (1993).
Fire et al., "Potent and specific genetic interference by double-stranded RNA in Caenorhabditis elegans," Nature (39)1:806-811 (1998).
Fire, A., "RNA-triggered gene silencing," Trends Genet. 15:358-363 (1999).
Friedmann, T. and H. Jinnah, "Gene therapy for disorders of the nervous system," TIBTECH 11(5):192-197 (1993).
Friedmann, T., "Gene therapy—a new kind of medicine," TIBTECH 11(5) 156-159 (1993).
Gardner et al., "The complete nucleotide sequence of an infectious clone of cauliflower mosaic virus by M13mp7 shotgun sequencing," Nucleic Acids Res. 9:2871-2888 (1981).
Gautier et al., "Alpha-DNA. IV: Alpha-anomeric and beta-anomeric tetrathymidylates covalently linked to intercalating oxazolopyridocarbazole. Synthesis, physicochemical properties and poly (rA) binding," Nucl. Acids Res. 15:6625-6641 (1987).
Geisert, E. and D. Bidanset, "A central nervous system keratan sulfate proteoglycan: localization to boundaries in the neonatal rat brain," Brain Res Dev Brain Res. 75(2):163-173 (1993).
GenBank Acc. No. 140198, Hypothetical 12.6 KDA Protein in SECF-TSX Intergenic Region, Retrieved from the Internet: <URL: ncbi.nlm.nih.gov/protein/140198, Published on Aug. 20, 2001 [Retrieved on Jan. 3, 2011] [2 pages].
GenBank Acc. No. Q59288, RecName: Full=Chondroitinase-AC; AltName: Full=Chondroitin sulfate AC lyase; AltName: Full=Chondroitin-AC eliminase; AltName: Full=Chondroitin-AC lyase; Flags: Precursor, Retrieved from the Internet: <URL: ncbi.nlm.nih.gov/protein/Q59288, Published on Nov. 30, 2010 [Retrieved on Jan. 3, 2011] [10 pages].
GenBank Acc. No. P84141, Chondroitinase (Chondroitin lyase), Retrieved from the Internet: <URL: ncbi.nlm.nih.gov/protein/p84141, Published on Nov. 28, 2006 [Retrieved on Jan. 3, 2011] [1 page].
GenBank Acc. No. Q46079, RecName: Full=Chondroitinase-B; AltName: Full=Chondroitin sulfate B lyase; AltName: Full=Chondroitin-B eliminase; AltName: Full=Chondroitin-B lyase; Flags: Precursor, Retrieved from the Internet: <URL: ncbi.nlm.nih.gov/protein/q46079, Published on Nov. 30, 2010 [Retrieved on Jan. 3, 2011] [8 pages].
Gilbert, W. and L. Villa-Komaroff, "Useful Proteins from Recombinant Bacteria," Scientific American 242(4):74-94 (1980).
Goldspiel et al., "Human gene therapy," Clinical Pharmacy 12:488-505 (1993).
Goochee et al., "The oligosaccharides of glycoproteins: bioprocess factors affecting oligosaccharide structure and their effect on glycoprotein properties," BioTechnology 9:1347-1355 (1991).
Gribskov, M. and R. Burgess, "Sigma factors from E. coli, B. subtilis, phage SP01, and phage T4 are homologous proteins," Nucl. Acids Res. 14:6745-6763 (1986).
Grosschedl et al., "Introduction of a mu immunoglobulin gene into the mouse germ line: specific expression in lymphoid cells and synthesis of functional antibody," Cell 38:647-658 (1984).
Grossman, M. and J. Wilson, "Retroviruses: delivery vehicle to the liver," Curr. Opin. in Genetics and Devel. 3:110-114 (1993).
Grunstein, M. and D. Hogness, "Colony hybridization: a method for the isolation of cloned DNAs that contain a specific gene," Proc. Natl. Acad. Sci. U.S.A. 72:3961 (1975).
Hamilton et al., "A species of small antisense RNA in post-transcriptional gene silencing in plants," Science 286:950-952 (1999).
Hammer et al., "Diversity of alpha-fetoprotein gene expression in mice is generated by a combination of separate enhancer elements," Science 235:53-58 (1987).
Hammond et al., "An RNA-directed nuclease mediates post-transcriptional gene silencing in Drosophila cells," Nature 404:293-296 (2000).
Hammond et al., "Post-transcriptional gene silencing by double-stranded RNA," Nature Rev Genet. 2:110-119 (2001).
Hanahan, D., "Heritable formation of pancreatic beta-cell tumours in transgenic mice expressing recombinant insulin/simian virus 40 oncogenes," Nature (3)15:115-122 (1985).
Hartman S. and R. Mulligan, "Two dominant-acting selectable markers for gene transfer studies in mammalian cells," Proc Natl Acad Sci 85:8047-8051 (1988).
Haselbeck, A. and W. Hosel., "Immunological detection of glycoproteins on blots based on labeling with digoxigenin," Methods in Mol. Biol. 14:161-173 (1993).
Herrera-Estrella et al., "Expression of chimaeric genes transferred into plant cells using a ti-plasmid-derived vector,"Nature 303:209-213 (1984).
Herrera-Estrella et al., "Light-inducible and chloroplast-associated expression of a chimaeric gene introduced into Nicotiana tabacum using a Ti plasmid vector," Nature 310(5973):115-120 (1984).
Hunkapiller et al, "A microchemical facility for the analysis and synthesis of genes and proteins," Nature 310:105-111 (1984).
Hutchison et al., "Mutagenesis at a specific position in a DNA sequence," J. Biol. Chem. 253:6551-6560 (1978).
Iida et al., "Cell surface chondroitin sulfate proteoglycans in tumor cell adhesion, motility and invasion," Semin. Cancer. Biol. 7(3)155-162 (1996).
Inoue et al., "Sequence-dependent hydrolysis of RNA using modified oligonucleotide splints and RNase H," FEBS Lett. 215:327-330 (1987).
Inoue et al., "Synthesis and hybridization studies on two complementary nona(2'-O-methyl)ribonucleotides," Nucl. Acids Res. 15:6131-6148 (1987).
Iozzo, R., "Matrix proteoglycans: from molecular design to cellular function," Annu. Rev. Biochem. 67:609-652 (1998).
Ishikawa et al., "Action of chondroitinase ABC on epidurally transplanted nucleus pulposus in the rabbit," Spine. 24(11):1071-1076 (1999).
IUPAC-IUB Commission on Biochemical Nomenclature "Abbreviated nomenclature of synthetic poypeptides-polymerized amino acids-revised recommendations—1971," Biochem.11(5):942-944 (1972).
Kanamori et al., "Deaminated neuraminic acid-rich glycoprotein of rainbow trout egg vitelline envelope. Occurrence of a novel alpha-2,8-linked oligo(deaminated neuraminic acid) structure in O-linked glycan chains," J. Biol. Chem. 265:21811-21819 (1990).
Kaneiwa et al., "Identification of human hyaluronidase-4 as a novel chondroitin sulfate hydrolase that preferentially cleaves the galactosaminidic linkage in the trisulfated tetrasaccharide sequence," Glycobiology 20(3):300-309 (2010).
Kelsey et al., "Species- and tissue-specific expression of human alpha 1-antitrypsin in transgenic mice," Genes and Devel. 1:161-171 (1987).
Kiem et al., "Retrovirus-mediated gene transduction into canine peripheral blood repopulating cells," Blood 83:1467-1473 (1994).

(56) References Cited

OTHER PUBLICATIONS

Kodo et al., "Antibody synthesis by bone marrow cells in vitro following primary and booster tetanus toxoid immunization in humans," J. Clin. Invest. 73:1377-1384 (1984).
Kohler, G. and C. Milstein, "Continuous cultures of fused cells secreting antibody of predefined specificity," Nature 256:495-497 (1975).
Koller, B. and O. Smithies, "Inactivating the beta 2-microglobulin locus in mouse embryonic stem cells by homologous recombination," Proc. Natl. Acad. Sci. USA 86:8932-8935 (1989).
Kollias et al., "Regulated expression of human A gamma-, beta-, and hybrid gamma beta-globin genes in transgenic mice: manipulation of the developmental expression patterns," Cell 46:89-94 (1986).
Kozak J., "Structural features in eukaryotic mRNAs that modulate the initiation of translation," J Biol. Chem. 266:19867-19870 (1991).
Kozarsky, K. and J. Wilson, "Gene therapy: adenovirus vectors," Current Opinion in Genetics and Development 3:499-503 (1993).
Krol et al., "Modulation of eukaryotic gene expression by complementary RNA or DNA sequences," BioTechniques 6:958-976 (1988).
Kroll et al., "A multifunctional prokaryotic protein expression system: overproduction, affinity purification, and selective detection," DNA Cell Biol 12:441-453 (1993).
Krumlauf et al., Developmental regulation of alpha-fetoprotein genes in transgenic mice, Mol. Cell. Biol. 5:1639-1648 (1985).
Leder et al., "Consequences of widespread deregulation of the c-myc gene in transgenic mice: multiple neoplasms and normal development," Cell 45:485-495 (1986).
Lemaitre et al., "Specific antiviral activity of a poly(L-lysine)-conjugated oligodeoxyribonucleotide sequence complementary to vesicular stomatitis virus N protein mRNA initiation site," Proc. Natl. Acad. Sci. USA 84:648-652 (1987).
Letsinger et al., "Cholesteryl-conjugated oligonucleotides: synthesis, properties, and activity as inhibitors of replication of human immunodeficiency virus in cell culture," Proc. Natl. Acad. Sci. USA 86:6553-6556 (1989).
Levine, J., "Increased expression of the NG2 chondroitin-sulfate proteoglycan after brain injury," J Neurosci. 14(8):4716-4730 (1994).
Li et al., "Coordinate regulation of cadherin and integrin function byt the chondroitin sulfate proteoglycan neurocan," J Cell Biol 149(6):1275-1288 (2000).
Li et al., "Importance of Glycosylation and Disulfide Bonds in Hyaluronidase Activity of Macaque Sperm Surface PH-20," J Androl 23(2):211-219 (2002).
Loeffler, J. and J. Behr, "Gene transfer into primary and established mammalian cell lines with lipopolyamine-coated DNA," Meth. Enzymol. 217:599-618 (1993).
Lowy et al., "Isolation of transforming DNA: cloning the hamster aprt gene," Cell 22:817-823 (1980).
Macdonald, R., "Expression of the pancreatic elastase I gene in transgenic mice," Hepatology 7:42S-51S(1987).
Maeyama et al., "Chondroitinase AC—a unique illegible structure of ABC," Seikagaku 57:1189 (1985). [in Japanese].
Magram et al., "Developmental regulation of a cloned adult beta-globin gene in transgenic mice," Nature 315:338-340 (1985).
Mason et al., "The hypogonadal mouse: reproductive functions restored by gene therapy," Science 234:1372-1378 (1986).
Mastrangeli et al., "Diversity of airway epithelial cell targets for in vivo recombinant adenovirus-mediated gene transfer," J. Clin. Invest. 91:225-234 (1993).
Mckeon et al., "Reduction of neurite outgrowth in a model of glial scarring following CNS injury is correlated with the expression of inhibitory molecules on reactive astrocytes," J Neurosci. 11(11):3398-3411 (1991).
Merrifield, J., "Solid phase peptide synthesis. I. The synthesis of a tetrapeptide," J Am Chem Soc 85:2149-2154 (1963).
Milev et al., "Interactions of the chondroitin sulfate proteoglycan phosphacan, the extracellular domain of a receptor-type protein tyrosine phosphatase, with neurons, glia, and neural cell adhesion molecules," J Cell Biol. 127(6 Pt 1):1703-1715 (1994).
Miller et al., "Use of retroviral vectors for gene transfer and expression," Meth. Enzymol. 217:581-599 (1993).
Mio et al., "Evidence that the serum inhibitor of hyaluronidase may be a member of the inter-alpha-inhibitor inhibitor family," J Biol Chem 275(42):32413-32421 (2000).
Mitani, K. and C. Caskey, "Delivering therapeutic genes—matching approach and application," TIBTECH 11(5):162-166 (1993).
Miyazono et al., "A structural analysis of the sugar chain (II)," Seikagaku 61:1023 (1989). [in Japanese].
Morgan, R. and W. Anderson, "Human gene therapy," An. Rev. Biochem. 62:191-217 (1993).
Mulligan, R., "The basic science of gene therapy," Science 260:926-932 (1993).
Nabel, G and P. Felgner., "Direct gene transfer for immunotherapy and immunization," TIBTECH 11:211-215 (1993).
Nadano et al., "A naturally occurring deaminated neuraminic acid, 3-deoxy-D-glycero-D-galacto-nonulosonic acid (KDN). Its unique occurrence at the nonreducing ends of oligosialyl chains in polysialoglycoprotein of rainbow trout eggs," J. Biol. Chem. 261:11550-11557 (1986).
Needleman, S. and C. Wunsch, "A general method applicable to the search for similarities in the amino acid sequence of two proteins," J Mol Biol. 48:443-453 (1970).
Nogrady, M., *Medicinal Chemistry A Biochemical Approach*, Oxford University Press, New York, pp. 388-392 (1985).
O'Reilly, M., "The preclinical evaluation of angiogenesis inhibitors," Invest New Drugs 15(1): 5-13 (1997).
Omitz et al., "Elastase I promoter directs expression of human growth hormone and SV40 T antigen genes to pancreatic acinar cells in transgenic mice," Cold Spring Harbor Symp. Quant. Biol. 50:399-409 (1986).
Pearson, W. and D. Lipman "Improved tools for biological sequence comparison," Proc. Natl. Acad. Sci. USA 85:2444-2448 (1988).
Pinkert et al., "An albumin enhancer located 10 kb upstream functions along with its promoter to direct efficient, liver-specific expression in transgenic mice," Genes and Devel. 1:268-276 (1987).
Pittelkow, M. and R. Scott, "New techniques for the in vitro culture of human skin keratinocytes and perspectives on their use for grafting of patients with extensive burns," Clinic Proc. 61:771-777 (1986).
Porath, J., "Immobilized metal ion affinity chromatography," Protein Expression and Purification 3:263-281 (1992).
Porteous et al., "How relevant are mouse models for human diseases to somatic gene therapy?" TIBTECH 11:173-181 (1993).
Powell et al., "Mechanisms of astrocyte-directed neurite guidance," Cell Tissue Res. 290(2):385-393 (1997).
Powell, E. and H. Geller, "Dissection of astrocyte-mediated cues in neuronal guidance and process extension," Glia. 26(1):73-83 (1999).
Pryce-Jones, R. and N. Lannigan, "Hyaluronidase: a colourimetric assay" [proceedings], J Pharm. Pharmacol. 31(Suppl):92P (1979).
Readhead et al., "Expression of a myelin basic protein gene in transgenic shiverer mice: correction of the dysmyelinating phenotype," Cell 48:703-712 (1987).
Rheinwald, J., "Serial cultivation of normal human epidermal keratinocytes," Meth. Cell Bio. 21A:229-254 (1980).
Rhodes et al., "Transformation of maize by electroporation of embryos," Methods Mol Biol 55:121-131 (1995).
Roberts et al., "Degradation of the proteoglycans of human articular cartilage by reactive oxygen metabolites," Basic Life Sci 49:353-356 (1988).
Robinson, C., "Gene therapy—proceeding from laboratory to clinic," TIBTECH 11:155 (1993).
Rodbard et al., "Statistical characterization of the random errors in the radioimmunoassay dose—response variable," Clin. Chem. 22:350-358 (1976).
Rosenfeld et al., "Adenovirus-mediated transfer of a recombinant alpha 1-antitrypsin gene to the lung epithelium in vivo," Science 252:431-434 (1991).
Rosenfeld et al., "In vivo transfer of the human cystic fibrosis transmembrane conductance regulator gene to the airway epithelium," Cell 68:143-155 (1992).

(56) References Cited

OTHER PUBLICATIONS

Ruoslahti, E. and Y. Yamaguchi, "Proteoglycans as modulators of growth factor activities," Cell 64(5):867-869 (1991).
Salmons, B. and W. Gunzberg, "Targeting of retroviral vectors for gene therapy," Human Gene Therapy 4:129-141 (1993).
Sambrook et al. (eds.), in: Molecular Cloning, a Laboratory Manual, Cold Spring Harbor Laboratory Press, vol. 3, p. B. 13 (1989).
Sarin et al., "Inhibition of acquired immunodeficiency syndrome virus by oligodeoxynucleoside methylphosphonates," Proc. Natl. Acad. Sci. USA 85:7448-7451 (1988).
Sarver et al., "Ribozymes as potential anti-HIV-1 therapeutic agents," Science 247:1222-1225 (1990).
Sasaki et al., "Effects of chondroitinase ABC on intradiscal pressure in sheep: an in vivo study," Spine 26(5):463-468 (2001).
Scharf et al., "Heat stress promoters and transcription factors," Results Probl Cell Differ 20:125-162 (1994).
Schwartz, R. and M. Dayhoff, Eds., "Matrices for detecting distant relationships", Atlas of Protein Sequence and Structure, National Biomedical Research Foundation, pp. 353-358 (1979).
Shani, M., "Tissue-specific expression of rat myosin light-chain," Nature 314:283-286 (1985).
Sharp, P., "RNA interference—2001," Genes Dev. 15:485-490 (2001).
Shilo, B. and R. Weinberg, "DNA sequences homologous to vertebrate oncogenes are conserved in *Drosophila melanogaster*," Proc. Natl. Acad Sci USA 78:6789-6792 (1981).
Sikora, K. "Gene therapy for cancer," TIBTECH 11(5):197-201 (1993).
Smith, T. and M. Waterman, "Comparison of biosequences," Advances in Applied Mathematics 2:482-489 (1981).
Smith, D. and K. Johnson, "Single-step purification of polypeptides expressed in *Escherichia coli* as fusions with glutathione S-transferase," Gene 7:31-40 (1988).
Snow et al., "Sulfated proteoglycans in astroglial barriers inhibit neurite outgrowth in vitro," Exp Neurol 109(1):111-130 (1990).
Snow, D. and P. Letourneau, "Neurite outgrowth on a step gradient of chondroitin sulfate proteoglycan (CS-PG)," J Neurobiol. 23(3):322-336 (1992).
Spatola, A., "Peptide backbone modifications," pp. 267-357 in Chemistry and Biochemistry of Amino Acids, Peptides, and Proteins, Weistein, Ed. vol. 7, Marcel Dekker:New York (1983).
Stein et al., "Physicochemical properties of phosphorothioate oligodeoxynucleotides," Nucl. Acids Res. 16:3209-3221 (1988).
Stemple, D. and D. Anderson, "Isolation of a stem cell for neurons and glia from the mammalian neural crest," Cell 71:973-985 (1992).
Swift et al., "Tissue-specific expression of the rat pancreatic elastase I gene in transgenic mice," Cell 38:639-646 (1984).
Tolstoshev, P., "Gene therapy, concepts, current trials and future directions," An. Rev. Phmacol. Toxicol. 32:573-596 (1993).
Townsend et al., "Separation of branched sialylated oligosaccharides using high-pH anion-exchange chromatography with pulsed amperometric detection," Anal. Biochem. 182:1-8 (1989).
Townsend, R., "Analysis of glycoconjugates using high-ph anion-exchange chromatography," in Carbohydrate Analysis: High-performance liquid chromatography and capillary electrophoresis (Z. El Rassi ed.). pp. 181-209 (1995).
Tuschl, T., "RNA interference and small interfering RNAs," Chem. Biochem. 2:239-245 (2001).
Tyle, P., "Iontophoretic devices for drug delivery," Pharmaceutical Research 3(6):3-18 (1986).
Valiyaveettil et al., "*Plasmodium falciparum* cytoadherence to human placenta: evaluation of hyaluronic acid and chondroitin 4-sulfate for binding of infected erythrocytes," Exp Parisitol 99(2):57-65 (2001).
Van Halbeek, H., "1H nuclear magnetic resonance spectroscopy of carbohydrate chains of glycoproteins," Methods Enzymol 230:132-168 (1994).
Varki, A., "Diversity in the sialic acids," Glycobiology 2: 25-40; Sialic Acids: Chemistry, Metabolism and Function, R. Schauer, Ed. (Springer-Verlag, N.Y. (1992).

Villa-Komaroff et al., "A bacterial clone synthesizing proinsulin," Proc. Natl. Acad. Sci. USA 75:3727-3731 (1978).
Vogel et al., "Aggrecan in bovine tendon," Matrix Biol 14(2):171-179 (1994).
Waeghe et al., "Determination, by methylation analysis, of the glycol-syl-linkage compositions of microgram quantities of complex carbohydrates," Carbohydr Res. 123:281-304 (1983).
Wagner et al., "Nucleotide sequence of the thymidine kinase gene of herpes simplex virus type 1," Proc. Natl. Acad. Sci. USA 78:1441-1445 (1981).
Walsh et al., "Gene therapy for human hemoglobinopathies," Proc. Soc. Exp. Biol. Med. 204:289-300 (1993).
Watson et al., Molecular Biology of the Gene, 4th Edition, The Benjamin/Cummings Pub. co., p. 224 (1987).
Whitlock, C. and O. Witte, "Long-term culture of B lymphocytes and their precursors from murine bone marrow," Proc Natl Acad Sci USA 79:3608-3612 (1982).
Wigler et al., "Transfer of purified herpes virus thymidine kinase gene to cultured mouse cells," Cell 11:223-232 (1977).
Wigler et al., "Transformation of mammalian cells with an amplifiable dominant-acting gene," Proc Natl Acad Sci. USA 77:3567-3570 (1980).
Williamson, R., "From genome mapping to gene therapy," TIBTECH 11(5):159-161 (1993).
Wivel, N., "Regulatory considerations for gene-therapy strategies and products," TIBTECH 11(5):189-191 (1993).
Wu, G. and C. Wu, "Delivery systems for gene therapy," Biotherapy 3:87-95 (1991).
Wu, G. and C. Wu, "Receptor-mediated in vitro gene transformation by a soluble DNA carrier system," J. Biol. Chem, 262:4429-4432 (1987).
Yamada et al., "The uniform galatose 4-sulfate structure in the carbohydrate-protein linkage region of human urinary trypsin inhibitor," Eur J Biochem 233:687-693 (1995).
Yamamoto et al., "Identification of a functional promoter in the long terminal repeat of *Rous sarcoma virus*," Cell 22:787-797 (1980).
Zamore et al., "RNAi: double-stranded RNA directs the ATP-dependent cleavage of mRNA at 21 to 23 nucleotide intervals," Cell 101:25-33 (2000).
Zijlstra et al., "Germ-line transmission of a disrupted beta 2-microglobulin gene produced by homologous recombination in embryonic stem cells," Nature 342:435-438 (1989).
Zon, G., "Oligonucleotide analogues as potential chemotherapeutic agents," Pharm. Res. 5:539-549 (1988).
Examination Report, issued Jul. 17, 2008, in connection with corresponding European Patent Application No. 03814054.7 [5 pages].
European Search Report, issued Feb. 18, 2011, in connection with corresponding European Patent Application No. 10183212.9 [7 pages].
U.S. Appl. No. 12/928,890, filed Dec. 21, 2010.
U.S. Appl. No. 13/068,025, filed Apr. 29, 2011.
U.S. Appl. No. 13/135,817, filed Jul. 15, 2011.
Arming et al., "In vitro mutagenesis of PH-20 hyaluronidase from human sperm," Eur J Biochem. 247(3):810-814 (1997).
Branden et al., "Prediction, engineering, and design of protein structures," *Introductions to Protein Structure*, Gerald Publishing Inc. p. 247 (1991).
Frost et al., "Purification, cloning, and expression of human plasma hyaluronidase," Biochem Biophys Res Commun 236(1):10-15 (1997).
Lalancette et al., "Characterization of an 80-kilodalton bull sperm protein identified as PH-20," Biol Reprod. 65(2):628-636 (2001).
Meyer et al., "The soluble hyaluronidase from bull testes is a fragment of the membrane-bound PH-20 enzyme," FEBS Lett. 18:413(2):385-388 (1997).
Letter/Written Disclosure of the Information Disclosure Statement for the above referenced application, mailed on Sep. 20, 2011, 2 pages.
Response to Examination Report, issued Feb. 18, 2011, for Canadian Patent Application No. 2,508,948, 20 pages.
Second Examination Report, issued Jun. 16, 2011 in connenction with Eurpean Patent application No. 10003894.2, 10 pages.

(56) References Cited

OTHER PUBLICATIONS

Summons to attend Oral Proceedings and Preliminary Opinion, issued Dec. 8, 2009, in connection with European Patent Application No. 03814054.7, 5 pages.
Response of Jan. 26, 2009 to Examination Report, issued Jul. 17, 2008, in connection with European Patent Application No. 03814054.7, 7 pages.
Response of Mar. 15, 2010 to Summons to Attend Oral Proceedings, issued Dec. 8, 2009 in connection with European Patent Application No. 03814054.7, 5 pages.
Response of Feb. 18, 2011 to Written Opinion, issued Jun. 18, 2010, in connection with European Patent Application No. 10003894.2, 9 pages.
Letter/Written Disclosure of the Supplemental Information Disclosure Statement for the above-referenced application, mailed on Sep. 19, 2012, 2 pages.
Response to European Search Report, issued Feb. 18, 2011, in connection with corresponding European Patent Application No. 10183212.9, 8 pages.
Office Action, issued Sep. 4, 2012, in connection with European Patent Application No. 10183212.9, 7 pages.
Response to Second Examination Report, issued Jun. 16, 2011, in connention with Eurpean Patent application No. 10003894.2, 12 pages.
Office Action, issued Jun. 15, 2012 in connection with Canadian Patent Application No. 2,508,948, 7 pages.
Csoka et al., "The six hyaluronidase-like genes in the human and mouse genomes," Matrix Biol, 20(8):499-508 (2001).
Hunnicutt et al., "Structural relationship of sperm soluble hyaluronidase to the sperm membrane protein PH-20," Biol Reprod, 54(6):1343-9 (1996).
European Search Report from Corresponding European Application No. 10003894.2.
Letter/Written Disclosure of the Supplemental Information Disclosure Statement for the above-referenced application, mailed Feb. 18, 2014, 2 pages.
Hunnicutt et al., "Sperm surface protein PH-20 is bifunctional: one activity is a hyaluronidase and a second, distinct activity is required in secondary sperm-zona binding," Biol Reprod. 55(1):80-86 (1996).
Stern et al., "Mammalian Hyaluronidases," Glycoforum, Jun. 23, 2000. Retrieved from the Internet. Retrieved from: <URL:glycoforum.gr.jp/science/hyaluronan/hapdf/HA15.pdf, 17 pages.
Summons to attend Oral Proceedings and Preliminary Opinion, issued Aug. 14, 2013, in connection with corresponding European Patent Application No. 10003894.2, 7 pages.
Response, dated Jan. 10, 2014, to Summons to attend Oral Proceedings and Preliminary Opinion, issued Aug. 14, 2013, in connection with corresponding European Patent Application No. 10003894.2, 9 pages.
Response, dated Dec. 17, 2012, to Office Action, issued Jun. 15, 2012 in connection with corresponding Canadian Patent Application No. 2,508,948, 34 pages.
Office Action, issued Aug. 1, 2013, in connection with corresponding Canadian Patent Application No. 2,508,948, 10 pages.
Response, filed Feb. 3, 2014, to Office Action, issued Aug. 1, 2013, in connection with corresponding Canadian Patent Application No. 2,508,948, 20 pages.
Summons to attend Oral Proceedings and Preliminary Opinion, issued Aug. 14, 2013, in connection with corresponding European Patent Application No. 10183212.9, 6 pages.
Response, dated Jan. 10, 2014, to Summons to attend Oral Proceedings and Preliminary Opinion, issued Aug. 14, 2013, in connection with European Patent Application No. 10183212.9, 7 pages.
Letter/Written Disclosure of the Supplemental Information Disclosure Statement for the above-referenced application, filed Apr. 7, 2014, 2 pages.
Decision of the Oral Proceedings, issued Mar. 21, 2014, in connection with European Patent Application No. 10183212.9, 12 pages.

* cited by examiner

HUMAN CHONDROITINASE GLYCOPROTEIN (CHASEGP), PROCESS FOR PREPARING THE SAME, AND PHARMACEUTICAL COMPOSITIONS COMPRISING THEREOF

CROSS REFERENCE TO RELATED APPLICATIONS

This application is a divisional application of U.S. application Ser. No. 10/539,110 filed Apr. 19, 2006, now issued as U.S. Pat. No. 7,544,499; which is a 35 USC § 371 National Stage application of International Application No. PCT/US2003/040090 filed Dec. 15, 2003; which claims the benefit under 35 USC § 119(e) to U.S. application Ser. No. 60/433,532 filed Dec. 16, 2002. The disclosure of each of the prior applications is considered part of and is incorporated by reference in the disclosure of this application.

BACKGROUND OF THE INVENTION

1. Field of the Invention

Eukaryotic Chondroitinase Glycoproteins (CHASEGP), portions thereof, particularly chondroitinase domains are provided. Also provided are prognostic, diagnostic and therapeutic methods using the chondroitinase glycoproteins and domains thereof and the encoding nucleic acid molecules.

2. Background Information

Glycosaminoglycans (GAGs) are complex linear polysaccharides of the extracellular matrix (ECM). GAG's are characterized by repeating disaccharide structures of an N-substituted hexosamine and a uronic acid, {hyaluronan (HA), chondroitin sulfate (CS), chondroitin (C), dernatan sulfate (DS), heparan sulfate (HS), heparin (H)], or a galactose, keratan sulfate (KS)}. Except for HA, all exist covalently bound to core proteins. The GAGs with their core proteins are structurally referred to as proteoglycans (PGs).

Chondroitin and dermatan sulfate are by far the most common glycosaminoglycans of the vertebrate body. Classification of chondroitin sulfates are: 1) CS-A (chondroitin-4-sulfate), 2) CS-B, or DS, containing 4-sulfated N-acetylgalactosamine and iduronic acid, and 3) CS-C (chondroitin-6-sulfate). Whereas the amino acid sequences, conformation, and biological functions of many of the CS-PG core proteins are now well established the precise structure of the GAG polymers are not firmly established. CS is comprised of between 15 and 50 disaccharide units of repeating beta-linked D-glucuronic acid and N-acetyl-D-galactosamine, the latter sulfated at the 4- or 6-position. Sulfation does not appear to be random, as assumed earlier. Repeating sulfation patterns have been detected, as well as other forms of repeating microheterogeneity including glucuronate-iduronate uronic acid epimerizations. The lack of reliable tools have to date, precluded the characterization. The bacterial chondroitinases exhibit cleavage specificity for glucuronate or iduronate residues (i.e. chondroitinase AC II and B, respectively). Unlike bacterial keratanases and heparinases, bacterial chondroitinases lack selective cleavage sites for specific sulfation sequences. Vertebrate chondroitinases may in fact have some form of such cleavage specificity and may be of critical importance for therapeutic intervention, as pharmaceuticals.

The CS- and DS-PGs are important ECM structures with both regulatory and structural roles. These molecules play both major structural components of bone, tendon, cartilage, scars, and fibrous connective tissue. CSPGs are also found in lesser amounts in most tissues, where they function as regulatory and signaling molecules involved in adhesion, migration, differentiation, and proliferation (Vogel, 1994). They bind growth factors, function as receptors, adhesion molecules, regulate deposition and distribution of other ECM polymers, and are themselves building blocks (Iozzo, 1998). Examples of these molecules include aggrecan, biglycan, brevican, decorin, neurocan, serglycin and versican. The peptide bikunin has a covalently bound CS chain, necessary for its activity as an inter-alpha-trypsin inhibitor (Yamada et al., 1995), and as a hyaluronidase inhibitor (Mio et al., 2000). CS-PGs also bind integrins, initiating cascades of signal transduction events (Iida et al., 1996; Li et al., 2000). A CS-PG is also a cell surface receptor for the malarial parasite in the human placenta (Valiyaveettil et al., 2001).

Following spinal cord injury, glial scars are produced by astrocytes and contain chondroitin sulfate proteoglycans (CSPGs). CSPGs play a crucial role in the inhibition of axon growth (Levine, 1994; Powell et al., 1997). For example, during fetal development, CSPGs repel axons and inhibit neural cell adhesion. CSPGs also play an important role in boundary formation (Snow et al., 1990, 1992; Powell and Geller, 1999). In addition the expression of CSPG increases following injury of CNS (McKeon et al., 1991; Davies et al., 1997).

Studies indicate that the inhibitory effects of CSPGs are principally due to the chondroitin sulfate (CS) glycosaminoglycan (GAG) sugar chain (Snow et al., 1990; Cole and McCable, 1991; Geisert and Bidanset, 1993). This is supported by the finding that administration of bacterial chondroitinases in fact promote axon regeneration when administered intrathecally. Moreover, electrophysiological experiments determined that regenerated CST axons established functional connections (Bradbury, et al 2002). In addition to their direct inhibitory effects, CSPGs could also interact with cell adhesion molecules or neurotrophic factors to influence neurite outgrowth (Roberts et al., 1988; Ruoslahti and Yamaguchi, 1991; Milev et al., 1994). Recombinant mammalian chondroitinases is thus useful to reverse the inhibition of CSPGs in the glial scar and to promote axon regeneration following injury.

Bacterial chondroitinases have also been utilized for the treatment of herniated disks in a process known as chemonucleolysis. Chondroitinase ABC can induce the reduction of intradiscal pressure in the lumbar spine. (Sasaki et al., 2001, Ishikawa et al., 1999). There are three types of disk injuries. A protruded disk is one that is intact but bulging. In an extruded disk, the fibrous wrapper has torn and the NP has oozed out, but is still connected to the disk. In a sequestered disk, a fragment of the NP has broken loose from the disk and is free in the spinal canal. Chemonucleolysis is effective on protruded and extruded disks, but not on sequestered disk injuries. In the United States, chemonucleolysis is approved only for use in the lumbar (lower) spine. In other countries, it has also been used successfully to treat cervical (upper spine) hernias. Chemonucleolysis is thus a conservative alternative to disk surgery when it is preferable to reduce disk pressure.

Chondroitinases are enzymes found throughout the animal kingdom. These enzymes degrade chondroitin sulfate through an endoglycosidase reaction. Specific examples of known chondroitinases include chondroitinase ABC (derived from Proteus vulgaris; Japanese Patent Application Laid-open No 6-153947, T. Yamagata, H. Saito, O. Habuchi, and S. Suzuki, J. Biol. Chem., 243, 1523 (1968), S. Suzuki, H. Saito, T. Yamagata, K. Anno, N. Seno, Y. Kawai, and T. Furuhashi, J. Biol. Chem., 243, 1543 (1968)), chondroitinase AC (derived from *Flavobacterium heparinum*; T. Yamagata, H. Saito, O. Habuchi, and S. Suzuki, J. Biol. Chem., 243, 1523 (1968)), chondroitinase ACII (derived from *Arthrobacter*

*aurescens*; K. Hiyama, and S. Okada, J. Biol. Chem., 250, 1824 (1975), K. Hiyama and S. Okada, J. Biochem. (Tokyo), 80, 1201 (1976)), chondroitinase ACIII (derived from *Flavobacterium* sp. Hp102; Hirofumi Miyazono, Hiroshi Kikuchi, Keiichi Yoshida, Kiyoshi Morikawa, and Kiyochika Tokuyasu, Seikagaku, 61, 1023 (1989)), chondroitinase B (derived from *Flavobacterium heparinum*; Y. M. Michelacci and C. P. Dietrich, Biochem. Biophys. Res. Commun., 56, 973 (1974), Y. M. Michelacci and C. P. Dietrich, Biochem. J., 151, 121 (1975), Kenichi Maeyama, Akira Tawada, Akiko Ueno, and Keiichi Yoshida, Seikagaku, 57, 1189 (1985)), chondroitinase C (derived from Flavobacterium sp. Hp102; Hirofumi Miyazono, Hiroshi Kikuchi, Kelichi Yosbida, Kiyoshi Morikawa, and Kiyochika Tokuyasu, Seikagaku, 61, 1023 (1939)), and the like.

Glycoproteins are composed of a polypeptide chain covalently bound to one or more carbohydrate moieties. There are two broad categories of glycoproteins with carbohydrates coupled through either N-glycosidic or O-glycosidic linkages to their constituent protein. The N- and O-linked glycans are attached to polypeptides through asparagine-N-acetyl-D-glucosamine and serine (threonine)-N-acetyl-D-galactosamine linkages, respectively. Complex N-linked oligosaccharides do not contain terminal mannose residues. They contain only terminal N-acetylglucosamine, galactose, and/or sialic acid residues. Hybrid oligosaccharides contain terminal mannose residues as well as terminal N-acetylglucosamine, galactose, and/or sialic acid residues.

With N-linked glycoproteins, an oligosaccharide precursor is attached to the amino group of asparagine during peptide synthesis in the endoplasmic reticulum. The oligosaccharide moiety is then sequentially processed by a series of specific enzymes that delete and add sugar moieties. The processing occurs in the endoplasmic reticulum and continues with passage through the cis-, medial- and trans-Golgi apparatus.

SUMMARY OF THE INVENTION

Provided herein are members of the hyaluronidase-like eukaryotic Chondroitinase Glycoprotein family, particularly the mammalian Chondroitinase Glycoproteins (also referred to herein as CHASEGPs). The CHASEGP provided herein is a CHASEGP family member, designated herein as CHASEGP. The chondroitinase domain and full-length protein, and uses thereof are also provided.

Proteins encoded by splice variants are also provided. Assays for identifying effectors, such as compounds, including small molecules, and conditions, such pH, temperature and ionic strength, that modulate the activation, expression or activity of CHASEGP are also provided herein. In exemplary assays, the effects of test compounds on the ability of a chondroitinase domain of CHASEGP to cleave a known substrate, typically a chondroitin sulfate or proteoglycan, are assessed. Agents, generally compounds, particularly small molecules, that modulate the activity of the chondroitinase domain are candidate compounds for modulating the activity of the CHASEGP. The chondroitinase domains can also be used to produce chondroitinase-specific antibodies. The chondroitinase domains provided herein include, but are not limited to, the N-terminal glycsoyl-hydrolase domain, or C-terminal truncated portions thereof that exhibit catalytic activity, in vitro chondroitinase assays, of any CHASEGP family member, including CHASEGP, generally from a mammal, including human, that, for example, is expressed in embryonic tissues at different levels from respective adult tissues.

Nucleic acid molecules encoding the proteins and chondroitinase domains are also provided. Nucleic acid molecules that encode a soluble chondroitinase domain or catalytically active portion thereof and also those that encode the full-length CHASEGP are provided. Nucleic acid encoding the chondroitinase domain (nucleotides 33-1200) and downstream nucleic acid in SEQ ID No. 3; and the chondroitinase domain of CHASEGP is set forth in SEQ ID No. 1 (amino acids 11-375) and in SEQ ID No. 2. The protein sequence and encoding nucleic acid sequence of the full-length CHASEGP are set forth in SEQ ID Nos. 1 and 3.

Also provided are nucleic acid molecules that hybridize to such CHASEGP-encoding nucleic acid along their full-length or along at least about 70%, 80% or 90% of the full-length and encode the chondroitinase domain or portion thereof are provided. Hybridization is generally effected under conditions of at least low, generally at least moderate, and often high stringency.

The isolated nucleic acid fragment is DNA, including genomic or cDNA, or is RNA, or can include other components, such as protein nucleic acid or other nucleotide analogs. The isolated nucleic acid may include additional components, such as heterologous or native promoters, and other transcriptional and translational regulatory sequences, these genes may be linked to other genes, such as reporter genes or other indicator genes or genes that encode indicators.

Also provided is an isolated nucleic acid molecule that includes the sequence of molecules that is complementary to the nucleotide sequence encoding CHASEGP or the portion thereof.

Also provided are fragments thereof or oligonucleotides that can be used as probes or primers and that contain at least about 10, 14, 16 nucleotides, generally less than 1000 or less than or equal-to 100, set forth in SEQ ID No. 3 or 4 (or the complement thereof); or contain at least about 30 nucleotides (or the complement thereof) or contain oligonucleotides that hybridize along their full-length (or at least about 70, 80 or 90% thereof) to any such fragments or oligonucleotides. The length of the fragments are a function of the purpose for which they are used and/or the complexity of the genome of interest. Generally probes and primers contain less than about 50, 150 or 500 nucleotides.

Also provided are plasmids containing any of the nucleic acid molecules provided herein. Cells containing the plasmids are also provided. Such cells include, but are not limited to, bacterial cells, yeast cells, fungal cells, plant cells, insect cells and animal cells.

Also provided is a method of producing CHASEGP by growing the above-described cells under conditions whereby the CHASEGP is expressed by the cells, and recovering the expressed CHASEGP polypeptide or glycoprotein. Methods for isolating nucleic acid encoding other CHASEGPs are also provided.

Also provided are cells, generally eukaryotic cells, such as mammalian cells and yeast cells, in which the CHASEGP polypeptide is expressed on the surface of the cells. Such cells are used in drug screening assays to identify compounds that modulate the activity of the CHASEGP polypeptide. These assays, including in vitro binding assays, and transcription based assays in which signal transduction mediated directly or indirectly, such as via activation of pro-growth factors, by the CHASEGP is assessed.

Also provided are peptides that are encoded by such nucleic acid molecules. Included among those polypeptides are the CHASEGP chondroitinase domain or a polypeptide with amino acid changes such that the specificity and/or chondroitinase activity remains substantially unchanged. In particular, a substantially purified mammalian CHASEGP polypeptide is provided that includes a chondroitinase catalytic domain and may additionally include other domains. The CHASEGP may form homodimers and can also form heterodimers with some other protein, such as a membrane-bound protein. Also provided is a substantially purified glycoprotein including a sequence of amino acids that has at least 60%, 70%, 80%, 81%, 82%, 83%, 84%, 85%, 86%, 87%, 88%, 89%, 90%, 91%, 92%, 93%, 94%, 95%, 96%, 97%, 98%, 99% identity to the CHASEGP where the percentage identity is determined using standard algorithms and gap penalties that maximize the percentage identity. A human CHASEGP polypeptide is exemplified, although other mammalian CHASEGP polypeptides are contemplated, such as that as set forth from mus musculus in SEQ ID NO. 2.

Splice variants of the CHASEGP, particularly those with a catalytically-active chondroitinase domain, are contemplated herein.

In other embodiments, substantially purified polypeptides that include a chondroitinase domain of a CHASEGP polypeptide or a catalytically active portion thereof, but that do not include the entire sequence of amino acids set forth in SEQ ID No. 1 are provided. Among these are polypeptides that include a sequence of amino acids that has at least 70%, 80%, 85%, 90%, 95% or 100% sequence identity to SEQ ID No. 1 or 2.

In a specific embodiment, a nucleic acid that encodes a eukaryotic chondroitinase glycoprotein, designated CHASEGP is provided. In particular, the nucleic acid includes the sequence of nucleotides set forth in SEQ ID No. 3, particularly set forth as nucleotides 744-2014 of SEQ ID No. 3, or nucleotides of SEQ ID No. 5 or a portion thereof that encodes a catalytically active polypeptide.

Also provided are nucleic acid molecules that hybridize under conditions of at least low stringency, generally moderate stringency, more typically high stringency to the SEQ ID No. 3 or 5 or degenerates thereof.

In one embodiment, the isolated nucleic acid fragment hybridizes to a nucleic acid molecule containing the nucleotide sequence set forth in SEQ ID No: 3 or 5 (or degenerates thereof) under high stringency conditions, in one embodiment contains the sequence of nucleotides set forth in SEQ ID Nos. 3 and 5. A full-length CHASEGP is set forth in SEQ ID No. 1 and is encoded by SEQ ID No. 3 or degenerates thereof.

Also provided are muteins of the chondroitinase domain of CHASEGP, particularly muteins in which the Cys residue in the chondroitinase domain that is free i.e., does not form disulfide linkages with any other Cys residue in the chondroitinase domain) is substituted with another amino acid substitution, typically, although not necessarily, with a conservative amino acid substitution or a substitution that does not eliminate the activity, and muteins in which a specific glycosylation site (s) is eliminated.

Hence muteins in which one or more of the Cys residues, particularly, a residue that is paired in the fill length molecule, but unpaired in the chondroitinase domain alone i.e., the Cys a residue position 455 (see SEQ ID Nos. 1) in the chondroitinase domain), is/are replaced with any amino acid, typically, although not necessarily, a conservative amino acid residue, such as Ser, are contemplated.

Muteins of CHASEGP, particularly those in which Cys residues, such as the unpaired Cys in the single chain chondroitinase domain, is replaced with another amino acid that does not eliminate the activity, are provided. Muteins in which other conservative or non-conservative amino acid substitutions in which catalytic activity is retained are also contemplated.

CHASEGP polypeptides, including, but not limited to splice variants thereof and nucleic acids encoding CHASEGPs, and domains, derivatives and analogs thereof are provided herein. Single chain secreted chondroitinase glycoproteins that have an N-terminus functionally equivalent to that generated by activation of a signal peptidase to form CHASEGP are also provided. There are three potential N-linked glycosylation sites at N86, N115 and N343 of CHASEGP as exemplified in SEQ ID NO: 1. Disulfide bonds form between the Cys residues C59-C351 and Cys residues C223 to C237 to form the core chondroitinase domain. There are additional potential disulfide bonds as follows: C376-C387, C381-C435 and C437-C446. Hence C455 is a free Cys in the single chain form of the chondroitinase domain.

N-linked glycosylation of the CHASEGPs are critical for their catalytic activity and stability. While altering the type of glycan modifying a glycoprotein can have dramatic affects on a protein's antigenicity, structural folding, solubility, and stability, most enzymes are not thought to require glycosylation for optimal enzyme activity. CHASEGPs are thus unique in this regard, that removal of N-linked glycosylation can result in near complete inactivation of the chondroitinase activity. The presence of N-linked glycans are critical for generating an active CHASEGP. Protein expression systems suitable for the introduction of critical N-linked glycosylation residues on CHASEGP are included. Additionally, the introduction of deglycosylated CHASEGP polypeptide in the presence of extracts capable of introducing N-linked glycans are included. In one aspect of the invention, complex glycosylation capped with sialylation is described whereas others capped with free mannose residues are contemplated as well. Most preferably, sialic acid is found in the terminal residues of N-linked glycosylation on CHASEGP.

N-linked oligosaccharides fall into several major types (oligomannose, complex, hybrid, sulfated), all of which have (Man)3-GlcNAc-GlcNAc-cores attached via the amide nitrogen of Asn residues that fell within -Asn-Xaa-Thr/Ser- sequences (where Xaa is not Pro). Glycosylation at an -Asn-Xaa-Cys- site has been reported for coagulation protein C. N-linked sites are often indirectly assigned by the appearance of a "blank" cycle during sequencing. Positive identification can be made after release of the oligosaccharide by PNGase F, which converts the glycosylated Asn to Asp. After PNGase F release, N-linked oligosaccharides can be purified using Bio-Gel P-6 chromatography, with the oligosaccharide pool subjected to preparative high pH anion exchange chromatography (HPAEC) (Townsend et al., (1989) Anal. Biochem. 182, 1-8). Certain oligosaccharide isomers can be resolved using HPAEC. Fucose residues will shift elution positions earlier in the HPAEC chromatogram, while additional sialic acid residues will increase the retention time. Concurrent treatment of glycoproteins whose oligosaccharide structures are known (e.g., bovine fetuin, a-1 acid glycoprotein, ovalbumin, RNAse B, transferrin) can facilitate assignment of the oligosaccharide peaks. The collected oligosaccharides can be characterized by a combination of compositional and methylation linkage analyses (Waegh et al., (1983) Carbohydrate Res. 123, 281-304), with anomeric configurations assigned by NMR spectroscopy (Van Halbeek (1993) in Methods Enzymol 230).

Hence, provided herein is a family of eukaryotic chondroitinase glycoproteins designated CHASEGPs, and functional domains, especially chondroitinase (or catalytic) domains thereof, muteins and other derivatives and analogs thereof. Also provided herein are nucleic acids encoding the CHASEGPs.

DETAILED DESCRIPTION OF THE INVENTION

A. Definitions

Unless defined otherwise, all technical and scientific terms used herein have the same meaning as is commonly understood by one of skill in the art to which the invention (s) belong. All patents, patent applications, published applications and publications, GenBank sequences, websites and other published materials referred to throughout the entire disclosure herein, unless noted otherwise, are incorporated by reference in their entirety. In the event that there are a plurality of definitions for terms herein, those in this section prevail.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11: 942-944).

As used herein, eukaryotic chondroitinase refers to a diverse family of glycosaminoglycan endoglucosaminidases, wherein a glutamate residue in the chondroitinase hydrolyzes the beta 1,4 linkages of chondroitin sulfates through an acid-base catalytic mechanism.

Of particular interest are CHASEGPs of mammalian, including human, origin. Those of skill in this art recognize that, in general, single amino acid substitutions in non-essential regions of a polypeptide do not substantially alter biological activity (see, e.g., Watson et al., (1987) Molecular Biology of the Gene, 4th Edition, The Benjamin/Cummings Pub. co., p. 224).

As used herein, membrane anchored CHASEGP, refers to a family of membrane anchored chondroitinases that share common structural features as described herein. Thus, reference, for example, to "CHASEGP" encompasses all glycoproteins encoded by the CHASEGP gene family, including but not limited to: Human HYAL4, mouse HYAL4, or an equivalent molecule obtained from any other source or that has been prepared synthetically or that exhibits the same activity. Sequences of encoding nucleic acid molecules and the encoded amino acid sequences of exemplary CHASEGPs and/or domains thereof are set forth, for example in SEQ ID NO: 3 and SEQ ID NO: 4. The term also encompasses CHASEGP with amino acid substitutions that do not substantially alter activity of each member and also encompasses splice variants thereof. Suitable substitutions, including, although not necessarily, conservative substitutions of amino acids, are known to those of skill in this art and can be made without eliminating the biological activity, such as the catalytic activity, of the resulting molecule.

As used herein a CHASEGP, whenever referenced herein, includes at least one or all of or any combination of: a polypeptide encoded by the sequence of nucleotides set forth in SEQ ID No. 3 or by a sequence of nucleotides that includes nucleotides that encode amino acids 1-481 of SEQ ID No. 1; a polypeptide encoded by a sequence of nucleotides that hybridizes under conditions of low, moderate or high stringency to the sequence of nucleotides set forth in is set form as nucleotides SEQ ID No. 3 or as SEQ ID No. 4; a polypeptide that includes the sequence of amino acids set forth as amino acids 1-425 of SEQ ID No. 5; a polypeptide that includes a sequence of amino acids having at least about 60%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with the sequence of amino acids set forth in SEQ ID No. 1 or 2 or as amino acids 1-425 of SEQ ID No. 6.

In particular, the CHASEGP polypeptide, with the chondroitinase domains as indicated in SEQ ID No. 6 is provided. The polypeptide is a single or two chain polypeptide. Smaller portions thereof that retain chondroitinase activity are also provided. The chondroitinase domains from CHASEGPs vary in size and constitution, including insertions and deletions in surface loops. Thus, for purposes herein, the catalytic domain is a portion of a CHASEGP, as defined herein, and is homologous to a domain of other hyaluronidase like sequences, such as HYAL1, HYAL2, HYAL3, and SPAM1, which have been previously identified; it was not recognized, however, that an isolated single chain form of the chondroitinase domain could function in in vitro assays. The Aspartate and Glutamate residues necessary for activity are present in conserved motifs.

The CHASEGP can be from any animal, particularly a mammal, and includes but are not limited to, humans, rodents, fowl, ruminants and other animals. The full-length polypeptide or secreted lipid anchorless form is contemplated or any domain thereof, including the chondroitinase domain.

As used herein, a "chondroitinase domain of an CHASEGP" refers to an beta 1,4 endoglucosaminidase domain of a CHASEGP that exhibits chondroitinase activity and shares homology and structural features with the hyaluronidase glycosyl-hydrolase family domains. Hence it is at least the minimal portion of the domain that exhibits chondroitinase activity as assessed by standard in vitro assays. Contemplated herein are such chondroitinase domains and catalytically active portions thereof. Also provided are truncated forms of the chondroitinase domain that include the smallest fragment thereof that acts catalytically as a single chain form.

A chondroitinase domain of an CHASEGP, whenever referenced herein, includes at least one or all of or any combination of or a catalytically active portion of: an N-linked glycoprotein polypeptide that includes the sequence of amino acids set forth in SEQ ID No. 1; a polypeptide encoded by a sequence of nucleotides that hybridizes under conditions of low, moderate or high stringency to the sequence of nucleotides set forth in SEQ ID No. 3 or 4; a polypeptide that includes the sequence of amino acids set forth in SEQ ID No. 1, 2 or 6; a polypeptide that includes a sequence of amino acids having at least about 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with the sequence of amino acids set forth in SEQ ID No. 1, 2; or 6; and/or a chondroitinase domain of a polypeptide encoded by a splice variant of the CHASEGP.

The chondroitinase domains of CHASEGPs vary in size and constitution, including insertions and deletions in surface loops. They retain conserved structure, including at least the proton donor, primary specificity pocket, oxyanion hole and/or other features of chondroitinase domains of beta 1,4 endoglucosaminidases. Thus, for purposes herein, the chondroitinase domain is a portion of an CHASEGP, as defined herein, and is homologous to a domain of other CHASEGPs. As with the larger class of enzymes of the hyaluronidase family, the CHASEGP catalytic domains share a high degree of amino acid sequence identity. The ASP and Glu residues necessary for activity are present in conserved motifs.

By active form is meant a form active in vivo and/or in vitro. As described herein, the chondroitinase domain also can exist as a secreted glycoprotein. It is shown herein that, at least in vitro, the single chain forms of the CHASEGPs and the catalytic domains or enzymatically active portions thereof (typically C-terminal truncations) exhibit chondroitinase activity. Hence provided herein are isolated forms of the chondroitinase domains of CHASEGPs and their use in in vitro drug screening assays for identification of agents that modulate the activity thereof.

As used herein, the catalytically active domain of a CHASEGP refers to the endoglucosaminidase domain.

CHASEGPs of interest include those that are active against chondroitin sulfates and chondroitin sulfate proteoglycans (CSPGs) in vivo and in vitro; and those in which substrates. As used herein, a human CHASEGP is one encoded by nucleic acid, such as DNA, present in the genome of a human, including all allelic variants and conservative variations as long as they are not variants found in other mammals.

As used herein, nucleic acid encoding a chondroitinase domain or catalytically active portion of a CHASEGP shall be construed as referring to a nucleic acid encoding only the recited single chain chondroitinase domain or active portion thereof, and not the other contiguous portions of the CHASEGP as a continuous sequence.

As used herein, catalytic activity refers to the activity of the CHASEGP as a chondroitinase. Function of the CHASEGP refers to its function in removal of chondroitin sulfate, including promotion of or involvement in initiation, growth or progression of axons, and also roles in signal transduction. Catalytic activity refers to the activity of the CHASEGP as a chondroitinase as assessed in in vitro glycosaminoglyan degrading enzyme assays that detect degradation of a selected substrate.

As used herein, "disease or disorder" refers to a pathological condition in an organism resulting from, e.g., infection or genetic defect, and characterized by identifiable symptoms.

As used herein, a splice variant refers to a variant produced by differential processing of a primary transcript of genomic nucleic acid, such as DNA, that results in more than one type of mRNA. Splice variants of CHASEGPs are provided herein.

As used herein, the chondroitinase domain of a CHASEGP protein refers to the chondroitinase domain of a CHASEFP that exhibits endoglucosaminidase activity. Hence it is at least the minimal portion of the protein that exhibits endoglucosaminidase activity as assessed by standard assays in vitro. Exemplary chondroitinase domains include at least a sufficient portion of sequences of amino acids set forth in SEQ ID No. 1 (encoded by nucleotides in SEQ ID No. 3) to exhibit endoglucosaminidase activity.

Also contemplated are nucleic acid molecules that encode a polypeptide that has endoglucosaminidase activity in an in vitro chondroitinase assay and that have at least 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with the full-length of a chondroitinase domain of an CHASEGP polypeptide, or that hybridize along their full-length or along at least about 70%, 80% or 90% of the full-length to a nucleic acids that encode a chondroitinase domain, particularly under conditions of moderate, generally high, stringency.

For the chondroitinase domains, residues at the in the N-terminal region can be critical for activity. It is shown herein that the chondroitinase domain of the CHASEGP is catalytically active. Hence the chondroitinase domain generally requires the N-terninal amino acids thereof for activity; the C-terminus portion can be truncated. The amount that can be removed can be determined empirically by testing the polypeptide for chondroitinase activity in an in vitro assay that assesses catalytic cleavage.

Hence smaller portions of the chondroitinase domains, particularly the single chain domains, thereof that retain chondroitinase activity are contemplated. Such smaller versions generally are C-terminal truncated versions of the chondroitinase domains. The chondroitinase domains vary in size and constitution, including insertions and deletions in surface loops. Such domains exhibit conserved structure, including at least one structural feature, such as the proton donor, and/or other features of chondroitinase domains of endoglucosaminidases. Thus, for purposes herein, the chondroitinase domain is a single chain portion of a CHASEGP, as defined herein, but is homologous in its structural features and retention of sequence of similarity or homology the chondroitinase domain of other hyaluronidase-like sequences. The glycoprotein exhibits chondroitinase activity as a single chain.

As used herein, by homologous means about greater than 25% nucleic acid sequence identity, such as 25% 40%, 60%, 70%, 80%, 90% or 95%. If necessary the percentage homology will be specified. The terms "homology" and "identity" are often used interchangeably. In general, sequences are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part/, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et Al. (1988) et al. (1988) Slam J Applied Math 48, 1073).

By sequence identity, the number of conserved amino acids are determined by standard alignment algorithms programs, and are used with default gap penalties established by each supplier. Substantially homologous nucleic acid molecules would hybridize typically at moderate stringency or at high stringency all along the length of the nucleic acid or along at least about 70%, 80% or 90% of the full-length nucleic acid molecule of interest. Also contemplated are nucleic acid molecules that contain degenerate codons in place of codons in the hybridizing nucleic acid molecule.

Whether any two nucleic acid molecules have nucleotide sequences that are at least, for example, 80%, 85%, 90%, 95%, 96%, 97%, 98% or 99% "identical" can be determined using known computer algorithms such as the "FAST A" progran, using for example, the default parameters as in Pearson et al. (1988; Proc. Natl. Acad. Sci. USA 85:2444); other programs include the GCG program package evereux, J., et at, nucleic acids research 12/ : 387 (1984)), BLASTP, BLASTN, FASTA (Altschul, et al., J. Molec. Biol. 403 (1990); Guide to Huge Computers, Martin J. Bishop, ed., Academic Press, San Diego, 1994, and Carillo et al. (1988) SIAM J Applied Math 48: 1073). For example, the BLAST function of the National Center for Biotechnology Information database can be used to determine identity. Other commercially or publicly available programs include, DNASTAR"MEGALIGN"PROGRAM (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program, e.g., Needleman et al. (1970), J Mol Biol. 48:443, as revised by Smith and Waterman Adv. Appl. Math (1981) 2:482). Briefly, the GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et at (1986) Nucl. Acids Res. 14: 6745, as described by Schwartz and Dayhoff, eds., Atlas Of Protein Sequence And Structure, National Biomedical Research Foundation, pp. 353-358 (1979); (2) a penalty of 3.0 for each gap and an additional 0.10 penalty for each symbol in each gap; and (3) no penalty for end gaps. Therefore, as used herein, the term "identity" represents a comparison between a test and a reference polypeptide or polynucleotide.

As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g. 10/100 amino acid difference (approximately 90% identity). Differences are defined as nucleic acid or amino acid substitutions, or deletions. At the level of homologies or identities above about 85-90%, the result should be independent of the program and gap parameters set; such high levels of identity can be assessed readily, often without relying on software.

As used herein, primer refers to an oligonucleotide containing two or more deoxyribonucleotides or ribonucleotides, typically more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

As used herein, animals include any animal, such as, but are not limited to, goats, cows, deer, sheep, rodents, pigs and humans. Non-human animals, exclude humans as the contemplated animal. The CHASEGPs provided herein are from any source, animal, plant, prokaryotic and fungal. Most CHASEGPs are of animal origin, including mammalian origin.

As used herein, genetic therapy involves the transfer of heterologous nucleic acid, such as DNA, into certain cells, target cells, of a mammal, particularly a human, with a disorder or conditions for which such therapy is sought. The nucleic acid, such as DNA, is introduced into the selected target cells in a manner such that the heterologous nucleic acid, such as DNA, is expressed and a therapeutic product encoded thereby is produced.

Alternatively, the heterologous nucleic acid, such as DNA, can in some manner mediate expression of DNA that encodes the therapeutic product, or it can encode a product, such as a peptide or RNA that in some manner mediates, directly or indirectly, expression of a therapeutic product. Genetic therapy can also be used to deliver nucleic acid encoding a gene product that replaces a defective gene or supplements a gene product produced by the mammal or the cell in which it is introduced. The introduced nucleic acid can encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutical useful time. The heterologous nucleic acid, such as DNA, encoding the therapeutic product can be modified prior to introduction into the cells of the afflicted host in order to enhance or otherwise alter the product or expression thereof. Genetic therapy can also involve delivery of an inhibitor or repressor or other modulator of gene expression.

As used herein, heterologous nucleic acid is nucleic acid that (if DNA encodes RNA) and proteins that are not normally produced in vivo by the cell in which it is expressed or that mediates or encodes mediators that alter expression of endogenous nucleic acid, such as DNA, by affecting transcription, translation, or other regulatable biochemical processes. Heterologous nucleic acid, such as DNA, can also be referred to as foreign nucleic acid, such as DNA. Any nucleic acid, such as DNA, that one of skill in the art would recognize or consider as heterologous or foreign to the cell in which is expressed is herein encompassed by heterologous nucleic acid; heterologous nucleic acid includes exogenously added nucleic acid that is also expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acid, such as DNA, that encodes other types of proteins, such as antibodies. Antibodies that are encoded by heterologous nucleic acid can be secreted or expressed on the surface of the cell in which the heterologous nucleic acid has been introduced.

Heterologous nucleic acid is generally not endogenous to the cell into which it is introduced, but has been obtained from another cell or prepared synthetically.

Generally, although not necessarily, such nucleic acid encodes RNA and proteins that are not normally produced by the cell in which it is expressed.

As used herein, a therapeutically effective product is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease.

As used herein, recitation that a glycoprotein consists essentially of the chondroitinase domain means that the only CHASEGP portion of the polypeptide is a chondroitinase domain or a catalytically active portion thereof The polypeptide can optionally, and generally will, include additional non-CHASEGP-derived sequences of amino acids.

As used herein, domain refers to a portion of a molecule, e.g., glycoproteins or the encoding nucleic acids, that is structurally and/or functionally distinct from other portions of the molecule.

As used herein, chondroitinase refers to an enzyme catalyzing hydrolysis of glycosaminoglycans.

For clarity reference to chondroitinase refers to all forms, and particular forms will be specifically designated. For purposes herein, the chondroitinase domain includes the membrane bound and soluble forms of a CHASEGP protein.

As used herein, nucleic acids include DNA, RNA and analogs thereof, including protein nucleic acids (PNA) and mixture thereof. Nucleic acids can be single or double-stranded. When referring to probes or primers, optionally labeled, with a detectable label, such as a fluorescent or radio-label, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous of sequence complementary to or identical a gene of interest. Probes and primers can be 10, 20, 30, 50, 100 or more nucleic acids long.

As used herein, nucleic acid encoding a fragment or portion of an CHASEGP refers to a nucleic acid encoding only the recited fragment or portion of CHASEGP, and not the other contiguous portions of the CHASEGP.

As used herein, operative linkage of heterologous nucleic to regulatory and effector sequences of nucleotides, such as promoters, enhancers, transcriptional and translational stop sites, and other signal sequences refers to the relationship between such nucleic acid, such as DNA, and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame. Thus, operatively linked or operationally associated refers to the functional relationship of nucleic acid, such as DNA, with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it can be necessary to remove, add or alter 5'untranslated portions of the clones to eliminate extra, potential inappropriate alternative translation initiation i.e. start) codons or other sequences that can interfere with or reduce expression, either at the level of transcription or translation. Alternatively, consensus ribosome binding sites (see, e,g., Kozak J. Biol. Chem. 266 : 19867-19870 (1991) can be inserted immediately 5' of the start codon and can enhance expression. The desirability of (or need for) such modification can be empirically determined.

As used herein, a sequence complementary to at least a portion of an RNA, with reference to antisense oligonucleotides, means a sequence having sufficient complimentary to be able to hybridize with the RNA, generally under moderate or high stringency conditions, forming a stable duplex; in the case of double-stranded CHASEGP antisense nucleic acids, a single strand of the duplex DNA (or dsRNA) can thus be tested, or triplex formation can be assayed. The ability to hybridize depends on the degree of complementarity and the length of the antisense nucleic acid. Generally, the longer the hybridizing nucleic acid, the more base mismatches with a CHASEGP encoding RNA it can contain and still form a stable duplex (or triplex, as the case can be). One skilled in the art can ascertain a tolerable degree of mismatch by use of standard procedures to determine the melting point of the hybridized complex.

For purposes herein, amino acid substitutions can be made in any of CHASEGPs and chondroitinase domains thereof provided that the resulting protein exhibits chondroitinase activity. Amino acid substitutions contemplated include conservative substitutions, such as those set forth in Table 1, which do not eliminate proteolytic activity. As described herein, substitutions that alter properties of the proteins, such as removal of cleavage sites and other such sites are also contemplated; such substitutions are generally non-conservative, but can be readily effected by those of skill in the art.

Suitable conservative substitutions of amino acids are known to those of skill in this art and can be made generally without altering the biological activity, for example enzymatic activity, of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). Also included within the definition, is the catalytically active fragment of a CHASEGP, particularly a single chain chondroitinase portion. Conservative amino acid substitutions are made, for example, in accordance with those set forth in TABLE 1 as follows:

TABLE 1 Original residue Conservative substitution Ala (A) Gly; Ser, Abu Arg (R) Lys, Orn Asn (N) Gln; His Cys (C) Ser Gin (Q) Asn Glu (E) ASP Gly (G) Ala; Pro His (H) Asn; Gin Ile (I) Leu; Val; Met; Nle; Nva; Leu (L); Val; Met; Nle; Nv Lys (K) Arg; Gin; Glu Met (M) Leu; Tyr; Ile; NLe Val Ornithine Lys; Arg Phe (F) Met; Leu; Tyr Ser (S) Thr Thr (T) Ser Trp (W) Tyr Tyr (Y) Trp; Phe Val (V) ILE; Leu; Met; Nle; Nv. Other substitutions are also permissible and can be determined empirically or in accord with known conservative substitutions.

As used herein, Abu is 2-aminobutyric acid; Orn is ornithine. As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, a probe or primer based on a nucleotide sequence disclosed herein, includes at least 10, 14, typically at least 16 contiguous sequence of nucleotides of SEQ ID No. 3, and probes of at least 30, 50 or 100 contiguous sequence of nucleotides of SEQ ID No. 3. The length of the probe or primer for unique hybridization is a function of the complexity of the genome of interest.

As used herein, amelioration of the symptoms of a particular disorder by administration of a particular pharmaceutical composition refers to any lessening, whether permanent or temporary, lasting or transient that can be attributed to or associated with administration of the composition.

As used herein, antisense polynucleotides refer to synthetic sequences of nucleotide bases complementary to mRNA or the sense strand of double-stranded DNA. Admixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double-stranded DNA, inhibition of RNA synthesis (transcription) occurs.

The resulting inhibition of translation and/or transcription leads to an inhibition of the synthesis of the protein encoded by the sense strand. Antisense nucleic acid molecule typically contain a sufficient number of nucleotides to specifically bind to a target nucleic acid, generally at least 5 contiguous nucleotides, often at least 14 or 16 or 30 contiguous nucleotides or modified nucleotides complementary to the coding portion of a nucleic acid molecule that encodes a gene of interest, for example, nucleic acid encoding a single chain chondroitinase domain of an CHASEGP.

As used herein, an array refers to a collection of elements, such as antibodies, containing three or more members. An addressable array is one in which the members of the array are identifiable, typically by position on a solid phase support. Hence, in general the members of the array are immobilized on discrete identifiable loci on the surface of a solid phase.

As used herein, antibody refers to an immunoglobulin, whether natural or partially or wholly synthetically produced, including any derivative thereof that retains the specific binding ability the antibody. Hence antibody includes any protein having a binding domain that is homologous or substantially homologous to an immunoglobulin binding domain. Antibodies include members of any immunoglobulin claims, including IgG IgM, IgA, IgD and IgE.

As used herein, antibody fragment refers to any derivative of an antibody that is less then full-length, retaining at least a portion of the full-length antibody's specific binding ability. Examples of antibody fragments include, but are not limited to Fab, Fab', F(ab)2, single chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, an Fv antibody fragment is composed of one variable heavy domain (VH) and one variable light domain linked by noncovalent interactions.

As used herein, a dsFV refers to an Fv with an engineered intermolecular disulfide bond.

As used herein, an F(ab)2 fragment is an antibody fragment that results from digestion of an immunoglobulin with pepsin at pH 4.0-4.5; it can be recombinantly expressed to produce the equivalent fragment.

As used herein, Fab fragments are antibody fragments that result from digestion of an immunoglobulin with papain; they can be recombinantly expressed to produce the equivalent fragment.

As used herein, scFVs refer to antibody fragments that contain a variable light chain V, and variable heavy chain (VH) covalently connected by a polypeptide linker in any order. The linker is of a length such that the two variable domains are bridged without substantial interference. Included linkers are (Gly-Ser)n residues with some Glu or Lys residues dispersed throughout to increase solubility.

As used herein, humanized antibodies refer to antibodies that are modified to include human sequences of amino acids so that administration to a human does not provoke an immune response. Methods for preparation of such antibodies are known. For example, to produce such antibodies, the hybridoma or other prokaryotic or eukaryotic cell, such as an E. coli or a CHO cell, that expresses the monoclonal antibody are altered by recombinant DNA techniques to express an antibody in which the amino acid, composition of the non-variable region is based on human antibodies. Computer programs have been designed to identify such regions.

As used herein, diabodies are dimeric scFV; diabodies typically have shorter peptide linkers than ScFVs, and they generally dimerize.

As used herein, production by recombinant means by using recombinant DNA methods means the use of the well known methods of molecular biology for expressing proteins encoded by cloned DNA.

As used herein the term assessing is intended to include quantitative and qualitative determination in the sense of obtaining an absolute value for the activity of an CHASEGP, or a domain thereof, present in the sample, and also of obtaining an index, ratio, percentage, visual or other value indicative of the level of the activity. Assessment can be direct or indirect and the chemical species actually detected need not of course be the proteolysis product itself but can for example be a derivative thereof or some further substance.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities can be observed in in vitro systems designed to test or use such activities. Thus, for purposes herein the biological activity of a luciferase is its oxygenase activity whereby, upon oxidation of a substrate, light is produced.

As used herein, functional activity refers to a polypeptide or portion thereof that displays one or more activities associated with a full-length protein.

Functional activities include, but are not limited to, biological activity, catalytic or enzymatic activity, antigenicity (ability to bind to or compete with a polypeptide for binding to an anti-polypeptide antibody), immunogenicity, ability to form multimers, the ability to Specifically bind to a receptor or ligand for the polypeptide.

As used herein, a conjugate refers to the compounds provided herein that include one or more CHASEGPs, including an CHASEGP, particularly single chain chondroitinase domains thereof, and one or more targeting agents. These conjugates include those produced by recombinant means as fusion proteins, those produced by chemical means, such as by chemical coupling, through, for example, coupling to sulfhydryl groups, and those produced by any other method whereby at least one CHASEGP, or a domain thereof, is linked, directly or indirectly via linker (s) to a targeting agent.

As used herein, a targeting agent is any moiety, such as a protein or effective portion thereof, that provides specific binding of the conjugate to a cell surface receptor, which, can internalize the conjugate or CHASEGP portion thereof. A targeting agent can also be one that promotes or facilitates, for example, affinity isolation or purification of the conjugate; attachment of the conjugate to a surface; or detection of the conjugate or complexes containing the conjugate.

As used herein, an antibody conjugate refers to a conjugate in which the targeting agent is an antibody.

As used herein, derivative or analog of a molecule refers to a portion derived from or a modified version of the molecule.

As used herein, an effective amount of a compound for treating a particular disease is an amount that is sufficient to ameliorate, or in some manner reduce the symptoms associated with the disease. Such amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms.

As used herein equivalent, when referring to two sequences of nucleic acids means that the two sequences in question encode the same sequence of amino acids or equivalent proteins. When equivalent is used in referring to two proteins or peptides, it means that the two proteins or peptides have substantially the same amino acid sequence with, only amino acid substitutions (such, as but not limited to, conservative changes such as those set forth in Table 1, above) that do not substantially alter the activity or function of the protein or peptide. When equivalent refers to a property, the property does not need to be present to the same extent (e.g., two peptides can exhibit different rates of the same type of enzymatic activity), but the activities are usually substantially the same. Complementary, when referring to two nucleotide sequences, means that the two sequences of nucleotides are capable of hybridizing, typically with less than 25%, 15%, 5% or 0% mismatches between opposed nucleotides. If necessary the percentage of complementarity will be specified. Typically the two molecules are selected such that they will hybridize under conditions of high stringency.

As used herein, an agent that modulates the activity of a protein or expression of a gene or nucleic acid either decreases or increases or otherwise alters the activity of the protein or, in some manner up-or down-regulates or otherwise alters expression of the nucleic acid in a cell.

As used herein, inhibitor of the activity of an CHASEGP encompasses any substance that prohibits or decrease production, post-translational modification(s), maturation, or membrane localization of the CHASEGP or any substance that interferes with or decreases the proteolytic efficacy of thereof, particularly of a single chain form in an in vitro screening assay.

As used herein, a method for treating or preventing neoplastic disease means that any of the symptoms, such as the tumor, metastasis thereof, the vascularization of the tumors or other parameters by which the disease is characterized are reduced, ameliorated, prevented, placed in a state of remission, or maintained in a state of remission. It also means that the hallmarks of neoplastic disease and metastasis can be eliminated, reduced or prevented by the treatment. Non-limiting examples of the hallmarks include uncontrolled degradation of the basement membrane and proximal extracellular matrix, migration, division, and organization of the endothelial cells into new functioning capillaries, and the persistence of such functioning capillaries.

As used herein, pharmaceutically acceptable salts, esters or other derivatives of the conjugates include any salts, esters or derivatives that can be readily prepared by those of skill in this art using known methods for such derivatization and that produce compounds that can be administered to animals or humans without substantial toxic effects and that either are pharmaceutical active or are prodrugs.

As used herein, a prodrug is a compound that, upon in vivo administration, is metabolized or otherwise converted to the biologically, pharmaceutically or therapeutically active form of the compound. To produce a prodrug, the pharmaceutical active compound is modified such that the active compound is regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

As used herein, a drug identified by the screening methods provided herein refers to any compound that is a candidate for use as a therapeutic or as a lead compound for the design of a therapeutic. Such compounds can be small molecules, including small organic molecules, peptides, peptide mimetics, antisense molecules or dsRNA, such as RNAi, antibodies, fragments of antibodies, recombinant antibodies and other such compounds that can serve as drug candidates or lead compounds.

As used herein, a peptidomimetic is a compound that mimics the conformation and certain stereochemical features of the biologically active form of a particular peptide. In general, peptidomimetics are designed to mimic certain desirable properties of a compound, but not the undesirable properties, such as flexibility, that lead to a loss of a biologically active conformation and bond breakdown. Peptidomimetics may be prepared from biologically active compounds by replacing certain groups or bonds that contribute to the undesirable properties with bioisosteres. Bioisosteres are known to those of skill in the art. For example the methylene bioisostere CH2S has been used as an amide replacement in enkephalin analogs (see, e.g. Spatola (1983) pp. 267-357 in Chemistry and Biochemistry of Amino Acids, Peptides, and Proteins, Weistein, Ed. volume 7, Marcel Dekker, New York). Morphine, which can be administered orally, is a compound that is a peptidomimetic of the peptide endorphin. For purposes herein, cyclic peptides are included among pepidomimetics.

As used herein, a promoter region or promoter element refers to a segment of DNA or RNA that controls transcription of the DNA or RNA to which it is operatively linked. The promoter region includes specific sequences that are sufficient for RNA polymerase recognition, binding and transcription initiation.

This portion of the promoter region is referred to as the promoter. In addition, the promoter region includes sequences that modulate this recognition, binding and transcription initiation activity of RNA polymerase. These sequences can be cis acting or can be responsive to trans acting factors. Promoters, depending upon the nature of the regulation, can be constitutive or regulated. Exemplary promoters contemplated for use in prokaryotes include the bacteriophage T7 and T3 promoters.

As used herein, a receptor refers to a molecule that has an affinity for a given ligand. Receptors can be naturally-occurring or synthetic molecules. Receptors can also be referred to in the art as anti-ligands. As used herein, the receptor and anti-ligand are interchangeable. Receptors can be used in their unaltered state or as aggregates with other species. Receptors can be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants such as on viruses, cells, or other materials, drugs, polynucleotides, nucleic acids, peptides, factors, lectins, sugars, polysaccharides, cells, cellular membranes, and organelles.

Examples of receptors and applications using such receptors, include but are not restricted to: a) enzymes: specific transport proteins or enzymes essential to survival of microorganisms, which could serve as targets for antibiotic (ligand) selection; b) antibodies: identification of a ligand-binding site on the antibody molecule that combines with the epitope of an antigen of interest can be investigated; determination of a sequence that mimics an antigenic epitope can lead to the development of vaccines of which the immunogen is based on one or more of such sequences or lead to the development of related diagnostic agents or compounds useful in therapeutic treatments such as for auto-immune diseases; c) nucleic acids: identification of ligand, such as protein or RNA, binding sites; d) catalytic polypeptides: polymers, including polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant (see, e.g., U.S. Pat. No. 5,215,899); e) hormone receptors: determination of the ligands that bind with high affinity to a receptor is useful in the development of hormone replacement therapies; for example, identification of ligands that bind to such receptors can lead to the development of drugs to control blood pressure; and f) opiate receptors: determination of ligands that bind to the opiate receptors in the brain is useful in the development of less-addictive replacements for morphine and related drugs.

As used herein, sample refers to anything which can contain an analyte for which an analyte assay is desired. The sample can be a biological sample, such as a biological fluid or a biological tissue. Examples of biological fluids include urine, blood, plasma, serum, saliva, semen, stool, sputum, cerebral spinal fluid, tears, mucus, sperm, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cells.

As used herein: stringency of hybridization in determining percentage mismatch is as follows: 1) high stringency: 0.1× SSPE, 0.1% SDS, 65° C.; 2) medium stringency: 0.2×SSPE, 0.1% SDS, 50° C.; and 3) low stringency: 1:0×SSPE, 0.1% SDS, 50° C. Those of skill in this art know that the washing step selects for stable hybrids and also know the ingredients of SSPE (see, e.g., Sambrook, E. F. Fritsch, T. Maniatis, in: Molecular Cloning, A Laboratory Manual, Cold spring Harbor Laboratory Press 1989 Vol 3, p. B. 13, see, also, numerous catalogs that describe commonly used laboratory solutions). SSPE is pH 7.4 phosphate-buffered 0.18 NaCl. Further, those of skill in the art recognize that the stability of hybrids is determined by the melting temperature (Tm), which is a function of the sodium ion concentration and temperature ($Tm=81.5°$ C.$-16.6+0.41$(% G+C)$-600/L$)), so that the only parameters in the wash conditions critical to hybrid stability are sodium ion concentration in the SSPE (or SSC) and temperature.

It is understood that equivalent stringencies can be achieved using alternative buffers, salts and temperatures. By way of example and not limitation, procedures using conditions of low stringency are as follows (see also Shilo and Weinberg, Proc. Natl. Acad Sci USA 78:6789-6792, 1981): filters containing DNA are pretreated for 6 hours at 40 C in a solution containing 35% formamide, 5×SSC, 50 mM Tris-HCl (pH 7.5), 5 mM EDTA, 0.1% PVP, 0.1% Ficoll 1% BSA, and 500 µg/ml denatured salmon sperm DNA (10×SSC is 1.5 M sodium chloride, and 0.15 M sodium citrate, adjusted to a pH 7).

Hybridizations are carried out in the same solution with the following modifications: 0.02% PVP, 0.02% Ficoll, 0.2% BSA, 100 µg/ml sperm DNA, 10% (wt/vol) dextran sulfate, and $5\text{-}20\times10^6$ cpm $^{32}$P-labled probe is used. Filters are incubated in hybridization mixture for 18-20 hours at 40° C. and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65-68° C. and reexposed to film. Other conditions of low stringency which can be used are well known in the art, e.g., as employed for cross-species hybridizations).

By way of example and not way of limitation, procedures using conditions of moderate stringency include, for example, but are not limited to, procedures using such conditions of moderate stringency are as follows: filters containing DNA are pretreated for 6 hours at 55° C. in a solution containing 6×SSC, 5× Denhardt's solution, 0.5% SDS and 100 ug/ml denatured salmon sperm DNA. Hybridizations are carried out in the same solution and $5\text{-}20\times10^6$ $^{32}$P labeled probe is used. Filters are incubated in hybridization mixture for 18-20 hours at 55° C. and then washed twice for 30 minutes at 60° C. in a solution containing 1×SSC and 0.1% SDS. Filters are blotted dry and exposed for autoradiography.

Other conditions of moderate stringency which can be used are well-known in the art. Washing of filters is done at 37° C. for 1 hour in a solution containing 2×SSC, 0.1% SDS.

By way of example and not way of limitation, procedures using conditions of high stringency are as follows: prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and $5\text{-}20\times10^6$ CPM $^{32}$P labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art.

The term substantially identical or substantially homologous or similar varies with the context as understood by those skilled in the relevant art and generally means at least 60% or 70%, preferably means at least 80%, 85% or more preferably at least 90%, and most preferably at least 95% identity.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, target cell refers to a cell that expresses a CHASEGP in vivo.

As used herein, test substance (or test compound) refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on an CHASEGP, particularly a single chain form that includes the chondroitinase domain or a sufficient portion thereof for activity, as determined by an in vitro method, such as the assays provided herein.

As used herein, the terms a therapeutic agent, therapeutic regimen, radioprotectant or chemotherapeutic mean conventional drugs and drug therapies, including vaccines, which are known to those skilled in the art. Radiotherapeutic agents are well known in the art.

As used herein, treatment means any manner in which the symptoms of a condition, disorder or disease are ameliorated or otherwise beneficially altered.

Treatment also encompasses any pharmaceutical use of the compositions herein.

As used herein, vector (or plasmid) refers to discrete elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, protein binding sequence refers to a protein or peptide sequence that is capable of specific binding to other protein or peptide sequences generally, to a set of protein or peptide sequences or to a particular protein or peptide sequence.

As used herein, epitope tag refers to a short stretch of amino acid residues corresponding to an epitope to facilitate subsequent biochemical and immunological analysis of the epitope tagged protein or peptide. Epitope tagging is achieved by including the sequence of the epitope tag to the protein-encoding sequence in an appropriate expression vector. Epitope tagged proteins can be affinity purified using highly specific antibodies raised against the tags.

As used herein, metal binding sequence refers to a protein or peptide sequence that is capable of specific binding to metal ions generally, to a set of metal ions or to a particular metal ion.

As used herein, a combination refers to any association between two or among more items.

As used herein, a composition refers to any mixture. It can be a solution, a suspension, liquid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions.

As used herein, a cellular extract refers to a preparation or fraction which is made from a lysed or disrupted cell.

As used herein, an agent is said to be randomly selected when the agent is chosen randomly without considering the specific sequences involved in the association of a protein alone or with its associated substrates, binding partners, etc. An example of randomly selected agents is the use a chemical library or a peptide combinatorial library, or a growth broth of an organism or conditioned medium.

As used herein, an agent is said to be rationally selected or designed when the agent is chosen on a non-random basis which takes into account the sequence of the target site and/or its conformation in connection with the agent's action. As described in the Examples, there are proposed binding sites for chondroitinase and (catalytic) sites in the glycoprotein having SEQ ID NO: 1 or SEQ ID NO: 2. Agents can be rationally selected or rationally designed by utilizing the peptide sequences that make up these sites. For example, a rationally selected peptide agent can be a peptide whose amino acid sequence is identical to the ATP or calmodulin binding sites or domains.

As used herein, N-linked sugar moiety refers to an oligosaccharide attached to a CHASEGP via the amide nitrogen of Asn residues. N-linked oligosaccharides fell into several major types (oligomannose, complex, hybrid, sulfated), all of which have (Man)3-GlcNAc-GlcNAc-cores attached via the amide nitrogen of Asn residues that fall within -Asn-Xaa-Thr/Ser- sequences (where Xaa is not Pro). N-linked sites are often indirectly assigned by the appearance of a "blank" cycle during sequencing. Positive identification can be made after release of the oligosaccharide by PNGase F, which converts the glycosylated Asn to Asp. After PNGase F release, N-linked oligosaccharides can be purified using Bio-Gel P-6 chromatography, with the oligosaccharide pool subjected to preparative high pH anion exchange chromatography (HPAEC) (Townsend et al., (1989) Anal. Biochem. 182, 1-8). Certain oligosaccharide isomers can be resolved using HPAEC. Fucose residues will shift elution positions earlier in the HPAEC chromatogram, while additional sialic acid residues will increase the retention time. Concurrent treatment of glycoproteins whose oligosaccharide structures are known (e.g., bovine fetuin, a-1 acid glycoprotein, ovalbumin, RNAse B, transferrin) can facilitate assignment of the oligosaccharide peaks. The collected oligosaccharides can be characterized by a combination of compositional and methylation linkage analyses (Waeghe et al., (1983) Carbohydr Res. 123, 281-304.), with anomeric configurations assigned by NMR spectroscopy (Van Halbeek (1993) in Methods Enzymol 230).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (.alpha. or. beta.), the ring bond, the ring position of the reducing saccharide involved in the bond, and then the name or abbreviation of the reducing saccharide (e.g., GlcNAc). The linkage between two sugars may be expressed, for example, as 2,3, 2.fw darw.3, or (2,3). Each saccharide is a pyranose.

Alternatively, oligosaccharides can be identified by fluorescence assisted carbohydrate electrophoresis (FACE) Callewaert et al. (2001) Glycobiology 11, 275-281.

As used herein, the term "sialic acid" refers to any member of a family of nine-carbon carboxylated sugars. The most common member of the sialic acid family is N-acetyl-neuraminic acid (2-keto-5-acetamindo-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261: 11550-11557; Kanamori et al. (1990) J. Biol. Chem. 265: 21811-21819. Also included are 9-substituted sialic acids such as a 9-O-C.sub.1-C.sub.6 acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) Glycobiology 2:25-40; Sialic Acids: Chemistry, Metabolism and Function, R. Schauer, Ed. (Springer-Verlag, N.Y. (1992)). The synthesis and use of sialic acid compounds in a sialation procedure is disclosed in international application WO 92/16640, published Oct. 1, 1992.

As used herein, PNGase refers to an Asparagine Peptide specific N-glycosidase F such as the Flavobacterium maningoseptum peptide-N-glycosidase F. PNGASE enzymes are characterized by their specificity towards N-linked rather than O-linked oligosaccharides. Characterization of PNGASE efficacy can be defined by both.

As used herein substantially terminated Sialation refers to N-linked oligosaccharides terminating with at least one sialic acid residue as a terminal sugar. Terminal sialic acids can be identified by FACE analysis of released carbohydrates following treatment with neuraminidase.

The circulatory lifetime of glycoproteins in the blood is highly dependent on the composition and structure of its N-linked carbohydrate groups. This fact is of direct relevance for therapeutic glycoproteins that are intended to be administered parenterally. In general, maximal circulatory half-life of a glycoprotein requires that its N-linked carbohydrate groups terminate in the sequence NeuAc-Gal-GlcNAc. Without the terminal sialic acid (NeuAc), the glycoprotein is rapidly cleared from the blood by a mechanism involving the recognition of the underlying N-acetylgalactosamine (GalNAc) or galactose (Gal) residues (Goochee et al. (1991) BioTechnology 9:1347-1355). For this reason, ensuring the presence of terminal sialic acid on N-linked carbohydrate groups of therapeutic glycoproteins is an important consideration for their commercial development.

Circulating glycoproteins are exposed to sialidase(s) (or neuraminidase) which can remove terminal sialic acid residues. Typically the removal of the sialic acid exposes galactose residues, and these residues are recognized and bound by galactose-specific receptors in hepatocytes (reviewed in Ashwell and Harford (1982) Ann. Rev. Biochem. 51:531). Liver also contains other sugar-specific receptors which mediate removal of glycoproteins from circulation. Specificities of such receptors also include N-acetylglucosamine, mannose, fucose and phosphomannose. Glycoproteins cleared by the galactose receptors of hepatocytes undergo substantial degradation and then enter the bile; glycoproteins cleared by the mannose receptor of Kupffer cells enter the reticuloendothelial system (reviewed in Ashwell and Harford (1982) Ann. Rev. Biochem. 51:53), B. Tissue Expression Profiles CHASEGP The CHASEGP is highly expressed in the placenta and skeletal muscle and is expressed at a low level in many other tissues. The CHASEGP transcript is found in skin, pooled human melanocyte, fetal heart, and pregnant uterus. CHASEGP is also expressed in germ cell tumors.

C. Identification and Isolation of CHASEGP Polypeptide Genes

The CHASEGP polypeptides and/or domains thereof; can be obtained by methods well known in the art for protein purification and recombinant protein expression. Any method known to those of skill in the art for identification of nucleic acids that encode desired genes can be used. Any method available in the art can be used to obtain a full-length (i.e., encompassing the entire coding region) cDNA or genomic DNA clone encoding a CHASEGP polypeptide. For example, the polymerase chain reaction (PCR) can be used to amplify a sequence that is expressed in normal tissues, e.g., nucleic acids encoding a CHASEGP polypeptide (SEQ. Nos: 1 and 2), in a genomic or cDNA library. Oligonucleotide primers that hybridize to sequences at the 3' and 5'termini of the identified sequences can be used as primers to amplify by PCR sequences from a nucleic acid sample (RNA or DNA—generally a cDNA library), from an appropriate source (e.g., placenta or skeletal muscle tissue).

PCR can be carried out, e.g., by use of a Perkin-Elmer Cetus thermal cycler and Taq polymerase (Gene Amp). The DNA being amplified can include mRNA or cDNA or genomic DNA from any eukaryotic species. One can choose to synthesize several different degenerate primers, for use in the PCR reactions.

It is also possible to vary the stringency of hybridization conditions used in priming the PCR reactions, to amplify nucleic acid homologs (e.g., to obtain CHASEGP polypeptide sequences from species other than humans or to obtain human sequences with homology to CHASEGP polypeptide) by allowing for greater or lesser degrees of nucleotide sequence similarity between the known nucleotide sequence and the nucleic acid homolog being isolated. For cross-species hybridization, low stringency to moderate stringency conditions are used. For same species hybridization, moderately stringent to highly stringent conditions are used. The conditions can be empirically determined.

After successful amplification of the nucleic acid containing all or a portion of the identified CHASEGP polypeptide sequence or of a nucleic acid encoding all or a portion of a CHASEGP polypeptide homolog, that segment can be molecularly cloned and sequenced, and used as a probe to isolate a complete cDNA or genomic clone. This, in turn, permits the determination of the gene's complete nucleotide sequence, the analysis of its expression, and the production of its protein product for functional analysis. Once the nucleotide sequence is determined, an open reading frame encoding the CHASEGP polypeptide gene protein product can be determined by any method well known in the art for determining open reading frames, for example, using publicly available computer programs for nucleotide sequence analysis. Once an open reading frame is defined, it is routine to determine the amino acid sequence of the protein encoded by the open reading frame. In this way, the nucleotide sequences of the entire CHASEGP polypeptide genes as well as the amino acid sequences of CHASEGP polypeptide proteins and analogs can be identified.

Any eukaryotic cell potentially can serve as the nucleic acid source for the molecular cloning of the CHASEGP polypeptide gene. The nucleic acids can be isolated from vertebrate, mammalian, human, porcine, bovine, feline, avian, equine, canine, as well as additional primate sources, insects, plants and other organisms. The DNA can be obtained by standard procedures known in the art from cloned DNA (e.g., a DNA "library"), by chemical synthesis, by cDNA cloning, or by the cloning of genomic DNA, or fragments thereof, purified from the desired cell (see, e.g., Sambrook et al. 1989, Molecular Cloning, A Laboratory Manual, 2d Ed., Cold Spring Harbor Laboratory Press, Cold Spring Harbor, New York; Glover, D. M. Ed., 1985, DNA Cloning: A Practical Approach, MRL Press, Ltd., Oxford, U. K. Vol. 1, 11. Clones derived from genomic DNA can contain regulatory and intron DNA regions in addition to coding regions; clones derived from cDNA will contain only exon sequences. For any source, the gene is cloned into a suitable vector for propagation thereof.

In the molecular cloning of the gene from genomic DNA, DNA fragments are generated, some of which will encode the desired gene.

The DNA can be cleaved at specific sites using various restriction enzymes. Alternatively, one can use DNAse in the presence of manganese to fragment the DNA, or the DNA can be physically sheared, for example, by sonication. The linear DNA fragments then can be separated according to size by standard techniques, including but not limited to, agarose and polyacrylamide gel electrophoresis and column chromatography.

Once the DNA fragments are generated, identification of the specific DNA fragment containing the desired gene can be accomplished in a number of ways.

For example, a portion of the CHASEGP polypeptide (of any species) gene (e.g., a PCR amplification product obtained as described above or an oligonucleotide having a sequence of a portion of the known nucleotide sequence) or its specific RNA, or a fragment thereof be purified and labeled, and the generated DNA fragments can be screened by nucleic acid hybridization to the labeled probe (Benton and Davis, Science 196:180 (1977); Grunstein and Hogness, Proc. Natl. Acad. Sci. U.S.A. 72:3961 (1975)). Those DNA fragments with substantial homology to the probe will hybridize. It is also possible to identify the appropriate fragment by restriction enzyme digestion (s) and comparison of fragment sizes with those expected according to a known restriction map if such is available or by DNA sequence analysis and comparison to the known nucleotide sequence of CHASEGP polypeptide. Further selection can be carried out on the basis of the properties of the gene. Alternatively, the presence of the gene can be detected by assays based on the physical, chemical, or- immunological properties of its expressed product. For example, cDNA clones, or DNA clones which hybrid-select the proper mRNA can be selected which produce a protein that, e.g., has similar or identical electrophoretic migration, isoelectric focusing behavior, proteolytic digestion maps, antigenic properties, chondroitinase activity. If an anti-CHASEGP polypeptide antibody is available, the protein can be identified by binding of labeled antibody to the putatively CHASEGP polypeptide synthesizing clones, in an ELISA (enzyme-linked immunosorbent assay)-type procedure.

Alternatives to isolating the CHASEGP polypeptide genomic DNA include, but are not limited to, chemically synthesizing the gene sequence from a known sequence or making cDNA to the mRNA that encodes the CHASEGP polypeptide.

For example, RNA for CDNA cloning of the CHASEGP polypeptide gene can be isolated from cells expressing the protein. The identified and isolated nucleic acids then can be inserted into an appropriate cloning vector. A large number of vector-host systems known in the art can be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene, La Jolla, Calif.). The insertion into a cloning vector can, for example, be accomplished by ligating the DNA fragment into a cloning vector which has complementary cohesive termini.

If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can include specific chemically synthesized oligonucleotides encoding restriction endonuclease recognition sequences. In an alternative method, the cleaved vector and CHASEGP polypeptide gene can be modified by homopolymeric tailing.

Recombinant molecules can be introduced into host cells via transformation, transfection, infection, electroporation, calcium precipitation and other methods, so that many copies of the gene sequence are generated.

In specific embodiments, transformation of host cells with recombinant DNA molecules that incorporate the isolated CHASEGP polypeptide gene, cDNA, or synthesized DNA sequence enables generation of multiple copies of the gene.

Thus, the gene can be obtained in large quantities by growing transformants, isolating the recombinant DNA molecules from the transformants and, when necessary, retrieving the inserted gene from the isolated recombinant DNA.

D. Vectors, Plasmids and Cells that Contain Nucleic Adds Encoding a CHASEGP Polypeptide or Chondroitinase Domain Thereof and Expression of CHASEGP Polypeptides Vectors and cells—For recombinant expression of one or more of the CHASEGP polypeptides, the nucleic acid containing all or a portion of the nucleotide sequence encoding the CHASEGP polypeptide can be inserted into an appropriate expression vector i.e., a vector that contains the necessary elements for the transcription and translation of the inserted protein coding sequence. The necessary transcriptional and translational signals can also be supplied by the native promoter for CHASEGP genes, and/or their flanking regions.

Also provided are vectors that contain nucleic acid encoding the CHASEGPs.

Cells containing the vectors are also provided. The cells include eukaryotic and prokaryotic cells, and the vectors are any suitable for use therein.

Prokaryotic and eukaryotic cells, including endothelial cells, containing the vectors are provided. Such cells include bacterial cells, yeast cells, fungal cells, plant cells, insect cells and animal cells. The cells are used to produce a CHASEGP polypeptide or chondroitinase domain thereof by (a) growing the above-described cells under conditions whereby the encoded CHASEGP polypeptide or chondroitinase domain of the CHASEGP polypeptide is expressed by the cell, and then (b) recovering the expressed chondroitinase domain protein. In the exemplified embodiments, the chondroitinase domain is secreted into the medium.

In one embodiment, the vectors include a sequence of nucleotides that encodes a polypeptide that has chondroitinase activity and contains all or a portion of only the chondroitinase domain, or multiple copies thereof of an CHASEGP protein are provided. Also provided are vectors that comprise a sequence of nucleotides that encodes the chondroitinase domain and additional portions of an CHASEGP protein up to and including a full length CHASEGP protein, as well as multiple copies thereof, are also provided. The vectors can selected for expression of the CHASEGP protein or chondroitinase domain thereof in the cell or such that the CHASEGP protein is expressed as a secreted protein. Alternatively, the vectors can include signals necessary for secretion of encoded proteins. When the chondroitinase domain is expressed the nucleic acid is linked to nucleic acid encoding a secretion signal, such as the *Saccharomyces cerevisae* a mating factor signal sequence or a portion thereof, or the native signal sequence.

A variety of host-vector systems can be used to express the protein coding sequence. These include but are not limited to mammalian cell systems infected with virus e.g. vaccinia virus, adenovirus, etc.); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements can be used.

Any methods known to those of skill in the art for the insertion of nucleic acid fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding CHASEGP polypeptide, or domains, derivatives, fragments or homologs thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for CHASEGP polypeptide. Promoters which can be used include but are not limited to the SV40 early promoter (Bemoist and Chambon, Nature 290:304-310 (1981) the promoter contained in the 3'long terminal repeat of Rous sarcoma virus (Yamamoto et al., Ce//22: 787-797 (1980) the herpes thymidine kinase promoter (Wagner et al., Proc. Natl. Acad. Sci. USA 78: 1441-1445 (1981) the regulatory sequences of the metallothionein gene (Brinster et al., Nature 296: 39-42 (1982)); prokaryotic expression vectors such as the β-Lactamase promoter (Villa-Kamaroff et al., Proc. Natl. Acad. Sci. USA 75: 3727-3731, 1978) or the TAC promoter, Deboer et al., Proc. Natl. Acad. Sci. USA 80:21-25, 1983); see also "Useful Proteins from Recombinant Bacteria": in Scientific American 242:79-94 (1980)); plant expression vectors containing the opaline synthetase promoter (Herrar-Estrella et al., Nature 303: 209-213 (1984)) or the cauliflower mosaic virus 35S RNA promoter (Garder et al., Nucleic Acids Res. 9:2871 (1981)), and the promoter of the photosynthetic enzyme ribulose bisphosphate carboxylase (Herrera-Estrella et al., Nature 310: 115-120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., Cell 38: 639-646 (1984); Ornitz et al., Cold Spring Harbor Symp. Quant. Biol. 50:399-409 (1986); Macdonald, Hepatology 7:425-515 (1987)); insulin gene control region which is active in pancreatic beta cells (Hanahan et al., Nature 315: 115-122 (1985)), immunoglobulin gene control region which is active in lymphoid cells (Grosschedl et al., Cell 38: 647-658 (1984); Adams et al., Nature 318: 533-538 (1985); Alexander et al., Mol. Cell Biol. 7:1436-1444 (1987)), mouse mammary tumor virus control region which is active in testicular, breast, lymphoid and mast cells (Leder et AL., Cell 45: 485-495 (1986)), albumin gene control region which is active in liver (Pinckert et al., Genes and Devel. 1:268-276 (1987)), alpha-fetoprotein gene control region which is active in liver (Krumlauf et al., Mol. Cell. Biol. 5 : 1639-1648 (1985); Hammer et al., Science 235: 53-58 1987)), alpha-1 antitrypsin gene control region which is active in liver (Kelsey et al., Genes And Devel. 1: 161-171 (1987)), beta globin gene control region which is active in myeloid cells (Mogram et al., Nature 315:338-340 (1985); Kollias et al., Cell 46:89-94 (1986)), myelin basic protein gene control region which is active in oligodendrocyte cells of the brain (Readhead et al., Cell 48: 703-712 (1987)), myosin light chain-2 gene control region which is active in skeletal muscle (Sani, Nature 314: 283-286 (1985)), and gonadotrophic releasing hormone gene control region which is active in gonadotrophs of the hypothalamus (Mason et al., Science 234:1372-1378 (1986)).

In a specific embodiment, a vector is used that contains a promoter operably linked to nucleic acids encoding a CHASEGP polypeptide, or a domain, fragment, derivative or homolog, thereof, one or more origins of replication, and optionally, one or more selectable markers (e.g., an antibiotic resistance gene).

Specific initiation signals may also be required for efficient translation of an CHASEGP sequence. These signals include the ATG initiation codon and adjacent sequences. In cases where CHASEGP, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al. (1994) Results Probl Cell Differ 20:125-62; Bittner et al. (1987) Methods in Enzymol 153:516-544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express CHASEGP may be transformed using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223-32) and adenine phosphoribosyltransferase (Lowy et al (1980) Cell 22:817-23) genes which can be employed in tk- or aprt-cells, respectively. Also, antimetabolite, antibiotic or herbicide resistance can be used as the basis for selection; for example, dhfr which confers resistance to methotrexate (Wigler M et al (1980) Proc Natl Acad Sci USA 77:3567-70); npt, which confers resistance to the aminoglycosides neomycin and G-418 (Colbere-Garapin F et al (1981) J Mol Biol 150:1-14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci USA 85:8047-51). Recently, the use of visible markers has gained popularity with such markers as anthocyanins, beta-glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121-131).

Identification of Transformants Containing the Polynucleotide Sequence

Although the presence/absence of marker gene expression suggests that the gene of interest is also present, its presence and expression should be confirmed. For example, if the CHASEGP is inserted within a marker gene sequence, recombinant cells containing CHASEGP can be identified by the absence of marker gene function. Alternatively, a marker gene can be placed in tandem with a CHASEGP sequence under the control of a single promoter. Expression of the marker gene in response to induction or selection usually indicates expression of the tandem CHASEGP as well.

Purification of CHASEGP

Host cells transformed with a CHASEGP nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing CHASEGP can be designed with signal sequences which direct secretion of CHASEGP through a prokaryotic or eukaryotic cell membrane. Other recombinant constructions may join CHASEGP to nucleotide sequence encoding a polypeptide domain which will facilitate purification of soluble proteins (Kroll D J et al (1993) DNA Cell Biol 12:441-53; cf discussion of vectors infra containing fusion proteins).

CHASEGP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and CHASEGP is useful to facilitate purification. One such expression vector provides for expression of a fusion protein compromising an CHASEGP and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263-281) while the enterokinase cleavage site provides a means for purifying the chemokine from the fusion protein.

In addition to recombinant production, fragments of CHASEGP may be produced by direct peptide synthesis using solid-phase techniques (cf Stewart et al (1969) Solid-Phase Peptide Synthesis, W H Freeman Co, San Francisco; Merrifield J (1963) J Am Chem Soc 85:2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of CHASEGP may be chemically synthesized separately and combined using chemical methods to produce the full length molecule.

Expression vectors containing the coding sequences, or portions thereof, of a CHASEGP polypeptide, is made, for example, by subcloning the coding portions into the Eco RI restriction site of each of the three PGEX vectors (glutathione S-transferase expression vectors (Smith and Johnson, Gene 7: 31-40 (1988)). This allows for the expression of products in the correct reading frame. Exemplary vectors and systems for expression of the chondroitinase domains of the CHASEGP polypeptides include the well-known *Pichia* vectors (available, for example, from Invitrogen, San Diego, Calif.), particularly those designed for secretion of the encoded proteins. The protein can also be expressed cytoplasmically, such as in the inclusion bodies. One exemplary vector is described in the examples.

Plasmids for transformation of *E. coli* cells, include, for example, the pET expression vectors (see, U.S. Pat. No. 4,952,496; available from Novagen, Madison, Wis.; see, also literature published by Novagen describing the system). Such plasmids include pET 11a, which contains the T71ac promoter, T7 terminator, the inducible *E. coli* lac operator, and the lac repressor gene; pET 12A-C, which contains the T7 promoter, T7 terminator, and the *E. COLI* OMPT secretion signal; and pET 15B and PET19B (Novagen, Madison, Wis.), which contain a His-Tag leader sequence for use in purification with a His column and a thrombin cleavage site that permits cleavage following purification over the column; the T7-lac promoter region and the T7 terminator.

The vectors are introduced into host cells, such as *Pichia* cells and bacterial cells, such as *E. coli*, and the proteins expressed therein. Exemplary *Pichia* strains, include, for example, GS115. Exemplary bacterial hosts contain chromosomal copies of DNA encoding T7 RNA polymerase operably linked to an inducible promoter, such as the LACUV promoter (see, U.S. Pat. No. 4,952,496). Such hosts include, but are not limited to, the lysogenic *E. coli* strain BL21 (DE3).

Expression and production of proteins The CHASEGP domains, derivatives and analogs can be produced by various methods known in the art. For example, once a recombinant cell expressing a CHASEGP polypeptide, or a domain, fragment or derivative thereof, is identified, the individual gene product can be isolated and analyzed. This is achieved by assays based on the physical and/or functional properties of the protein, including, but not limited to, radioactive labeling of the product followed by analysis by gel electrophoresis, immunoassay, cross-linking to marker-labeled product, and assays of proteolytic activity.

The CHASEGP polypeptides can be isolated and purified by standard methods known in the art (either from natural sources or recombinant host cells expressing the complexes or proteins), including but not restricted to column chromatography (e.g., ion exchange, affinity, gel exclusion, reversed-phase high pressure and fast protein liquid), differential centrifugation, differential solubility, or by any other standard technique used for the purification of proteins.

Functional properties can be evaluated using any suitable assay known in the art. Alternatively, once a CHASEGP polypeptide or its domain or derivative is identified, the amino acid sequence of the protein can be deduced from the nucleotide sequence of the gene which encodes it. As a result, the protein or its domain or derivative can be synthesized by standard chemical methods known in the art (e.g. see Hunkapiller et al, Nature 310:105-111 (1984)).

Manipulations of CHASEGP polypeptide sequences can be made at the protein level. Also contemplated herein are CHASEGP polypeptide proteins, domains thereof, derivatives or analogs or fragments thereof, which are differentially modified during or after translation, e.g., by glycosylation, acetylation, phosphorylation, amidation, derivatization by known protecting/blocking groups, proteolytic cleavage, linkage to an antibody molecule or other cellular ligand.

Any of numerous chemical modifications can be carried out by known techniques, including but not limited to specific chemical cleavage by cyanogen bromide, trypsin, chymotrypsin, papain, V8 chondroitinase, NABH4, acetylation, formylation, oxidation, reduction, metabolic synthesis in the presence of tunicamycin and other such agents.

In addition, domains, analogs and derivatives of a CHASEGP polypeptide can be chemically synthesized. For example, a peptide corresponding to a portion of a CHASEGP polypeptide, which includes the desired domain or which mediates the desired activity in vitro can be synthesized by use of a peptide synthesizer.

Furthermore, if desired, nonclassical amino acids or chemical amino acid analogs can be introduced as a substitution or addition into the CHASEGP polypeptide sequence. Non-classical amino acids include but are not limited to the D-isomers of the common amino acids, a-amino isobutyric acid, 4-aminobutyric acid, Abu, 2-aminobutyric acid, E-ABU, e-Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, ca-methyl amino acids, na-methyl amino acids, and amino acid analogs in general, furthermore, the amino acid can be d (dextrorotary) or l (levorotary).

In cases where natural products are suspected of being mutant or are isolated from new species, the amino acid sequence of the CHASEGP polypeptide isolated from the natural source, as well as those expressed in vitro, or from synthesized expression vectors in vivo or in vitro, can be determined from analysis of the DNA sequence, or alternatively, by direct sequencing of the isolated protein. Such analysis can be performed by manual sequencing or through use of an automated amino acid sequenator.

Modifications—A variety of modifications of the CHASEGP polypeptides and domains are contemplated herein. A CHASEGP-encoding nucleic acid molecule can be modified by any of numerous strategies known in the art (Sambrook ET A/. (1990), Molecular Cloning, A Laboratory Manual, 2d ed., Cold Spring Harbor Laboratory, Cold Spring Harbor, N.Y.). The sequences can be cleaved at appropriate sites with restriction endonuclease (s), followed by further enzymatic modification if desired, isolated, and ligated in vitro. In the production of the gene encoding a domain, derivative or analog of CHASEGP, care should be taken to ensure that the modified gene retains the original translational reading frame, uninterrupted by translational stop signals, in the gene region where the desired activity is encoded.

Additionally, the CHASEGP-encoding nucleic acid molecules can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Also, as described herein muteins with primary sequence alterations, such as replacements of Cys residues and elimination or addition of glycosylation sites are contemplated; the CHASEGP of SEQ ID No. 1 has three potential glycosylation sites. Such mutations can be effected by any technique for mutagenesis known in the art, including, but not limited to, chemical mutagenesis and in vitro site-directed mutagenesis (Hutchinson et al., J. Biol. Chem. 253: 6551-6558 (1978)), use of TABE Linkers Pharmacia). In one embodiment, for example, a CHASEGP polypeptide or domain thereof is modified to include a fluorescent label. In other specific embodiments, the CHASEGP polypeptide is modified to have a heterobifonctional reagent, such heterobifunctional reagents can be used to crosslink the members of the complex.

In addition, domains, analogs and derivatives of a CHASEGP can be chemically synthesized. For example, a peptide corresponding to a portion of a CHASEGP, which includes the desired domain or which mediates the desired activity in vitro can be synthesized by use of a peptide synthesizer. Furthermore, if desired, nonclassical amino acids or chemical amino acid analogs can be introduced as a substitution or addition into the CHASEGP sequence. Non-classical amino acids include but are not limited to the D-isomers of the common amino acids, a-amino isobutyric acid, 4-aminobutyric acid, Abu, 2-aminobutyric acid, S-ABU, e-Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as ti-methyl amino acids, ca-methyl amino acids, na-methyl amino acids, and amino acid analogs in general. Furthermore, the amino acid can be "d" (dextrorotary) or "l" (levorotary).

E. Generation of a Functionally Glycosylated CHASEGP with N-linked Sugar Moieties Properly N-glycosylated CHASEGP is required to generate a catalytically stable protein. N-linked glycosylation of CHASEGP can be achieved through various techniques. Glycosylation of CHASEGP can be achieved by introducing nucleic acids encoding CHASEGP into cells of eukaryotic origin capable of N-linked glycosylation or alternatively, by contacting CHASEGP polypeptide with cell free extracts or purified enzymes capable of introducing the desired N-linked sugar moieties.

F. Selection of Expression System

Eukaryotic cell expression systems vary in the extent and type of glycosylation they introduce into an ectopically expressed polypeptide.

N-glycosylation of CHASEGP polypeptide in vitro. CHASEGP polypeptide can be N-glycosylated by contact of CHASEGP polypeptide with cell-free extracts containing activity capable of transferring N-linked sugars to CHASEGP polypeptide such as canine microsomal membranes or through coupled transcription and translation as is commercially available (Promega Madison Wis.).

G. Detection and Characterization of N-linked Sugar Moieties on CHASEGP

Determining whether a protein is in fact glycosylated is the initial step in glycoprotein glycan analysis. Polyacrylamide gel electrophoresis in the presence of sodium dodecyl sulfate (SDS-PAGE) has become the method of choice as the final step prior to protein sequencing. Glycosylated proteins often migrate as diffuse bands by SDS-PAGE. A marked decrease in band width and change in migration position after treatment with peptide-N4-(N-acetyl-D-glucosaminyl) asparagine amidase (PNGase F) is considered diagnostic of N-linked glycosylation. If the other types of glycosylation are predominant other approaches must be used. Lectin blotting methods provide an approach which is independent of the class of glycosylation (N versus O). Lectins, carbohydrate-binding proteins from various plant tissues, have both high affinity and narrow specificity for a wide range of defined sugar epitopes found on glycoprotein glycans (Cummings, R. D. (1994) Methods in Enzymol. 230, 66-86.). When conjugated with biotin or digoxigenin, they can be easily identified on membrane blots through a colorimetric reaction utilizing avidin or anti-digoxigenin antibodies conjugated with alkaline phosphatase (Haselbeck, et al. (1993) Methods in Mol. Biol. 14, 161-173.), analogous to secondary antibody-alkaline phosphatase reactions employed in Western blotting. Screening with a panel of lectins with well-defined specificity can provide considerable information about a glycoprotein's carbohydrate complement. Importantly, the color development amplification is sufficiently high that 10-50 ng of a glycoprotein can easily be seen on a membrane blot of an SDS-PAGE. Although lectins exhibit very high affinity for their cognate ligands, some do reveal significant avidity for structurally-related epitopes. Thus, it is important to carefully note the possibility of cross-reactivity when choosing a panel of lectins, and apply those with the highest probability of individually distinguishing complex, hybrid and high mannose N-linked glycans from O-linked structures.

Monosaccharide analysis can also be used to determine whether CHASEGP is glycosylated and as in the case of lectin analysis provides additional information on structural features. Quantitative monosaccharide composition analysis i) identifies glycosylated proteins, ii) gives the molar ratio of individual sugars to protein, iii) suggests, in some cases, the presence of oligosaccharide classes, iv) is the first step in designing a structural elucidation strategy, and v) provides a measure of production consistency for recombinant glycoprotein therapeutics. In recent years high-pH anion-exchange chromatography with pulsed amperometric detection (HPAEC-PAD) has been extensively used to determine monosaccharide composition (Townsend, et al. (1995) in Carbohydrate Analysis: High-performance liquid chromatography and capillary electrophoresis (Z. El Rassi ed.). pp. 181-209.). More recently, fluorophore-based labeling methods have been introduced and many are available in kit form. A distinct advantage of fluorescent methods is an increase in sensitivity (50-fold). One potential disadvantage is that different monosaccharides may demonstrate different selectivity for the fluorophore during the coupling reaction, either in the hydrolysate or in the external standard mixture. However, the increase in sensitivity and the ability to identify which monosaccharides are present from a small portion of the total amount of available glycoprotein, as well as the potential for greater sensitivity using laser induced fluorescence makes this approach attractive.

Monosaccharide composition analysis of small amounts of CHASEGP is best performed on PVDF (PSQ) membranes, after either electroblotting (Weitzhandler et al, (1993) J. Biol. Chem. 268, 5121-5130.) or if smaller aliquots are to be analyzed on dot blots. PVDF is an ideal matrix for carbohydrate analysis since neither mono- or oligosaccharides bind to the membrane, once released by either acid or enzymatic hydrolysis.

H. Screening Methods

The chondroitinase domains, as shown herein, can be used in a variety of methods to identity compounds that modulate the activity thereof.

Several types of assays are exemplified and described herein. It is understood that the chondroitinase domains can be used in other assays. It is shown here, however, that the chondroitinase domains exhibit catalytic activity. As such they are ideal for in vitro screening assays.

They can also be used in binding assays. The CHASEGP full length zymogens, activated enzymes, and chondroitinase domains are contemplated for use in any screening assay known to those of skill in the art, including those provided herein. Hence the following description, if directed to chondroitinase assays is intended to apply to use of a single chain chondroitinase domain or a catalytically active portion thereof of any chondroitinase, including a CHASEGP. Other assays, such as binding assays are provided herein, particularly for use with a CHASEGP, including any variants, such as splice variants thereof.

1. Catalytic Assays for identification of agents that modulate the chondroitinase activity of a SCHASEGP protein. Methods for identifying a modulator of the catalytic activity of a CHASEGP, particularly a single chain chondroitinase domain or catalytically active portion thereof, are provided herein. The methods can be practiced by: contacting the CHASEGP, a full-length zymogen or activated form, and particularly a single-chain domain thereof, with a substrate of the CHASEGP in the presence of a test substance, and detecting the proteolysis of the substrate, whereby the activity of the CHASEGP is assessed, and comparing the activity to a control. For example, a control can be the activity of the CHASEGP assessed by contacting a CHASEGP, including a full-length zymogen or activated form, and particularly a single-chain domain thereof, particularly a single-chain domain thereof, with a substrate of the CHASEGP, and detecting the proteolysis of the substrate, whereby the activity of the CHASEGP is assessed. The results in the presence and absence of the test compounds are compared. A difference in the activity indicates that the test substance modulates the activity of the CHASEGP. Activators of CHASEGP activation cleavage are also contemplated; such assays are discussed below.

In one embodiment a plurality of the test substances are screened simultaneously in the above screening method. In another embodiment, the CHASEGP is isolated from a target cell as a means for then identifying agents that are potentially specific for the target cell.

In another embodiment, a test substance is a therapeutic compound, and whereby a difference of the CHASEGP activity measured in the presence and in the absence of the test substance indicates that the target cell responds to the therapeutic compound.

One method includes the steps of (a) contacting the CHASEGP polypeptide or chondroitinase domain thereof with one or a plurality of test compounds under conditions conducive to interaction between the ligand and the compounds; and (b) identifying one or more compounds in the plurality that specifically binds to the ligand.

Another method provided herein includes the steps of a) contacting a CHASEGP polypeptide or chondroitinase domain thereof with a substrate of the CHASEGP polypeptide, and detecting the degradation of substrate, whereby the activity of the CHASEGP polypeptide is assessed; b) contacting the CHASEGP polypeptide with a substrate of the CHASEGP polypeptide in the presence of a test substance, and detecting the degradation of the substrate, whereby the activity of fee CHASEGP polypeptide is assessed; and c) comparing the activity of the CHASEGP polypeptide assessed in steps a) and b), whereby the activity measured in step a) differs from the activity measured in step b) indicates that the test substance modulates the activity of the CHASEGP polypeptide.

In another embodiment, a plurality of the test substances are screened simultaneously. In comparing the activity of a CHASEGP polypeptide in the presence and absence of a test substance to assess whether the test substance is a modulator of the CHASEGP polypeptide, it is unnecessary to assay the activity in parallel, although such parallel measurement is typical. It is possible to measure the activity of the CHASEGP polypeptide at one time point and compare the measured activity to a historical value of the activity of the CHASEGP polypeptide.

For instance, one can measure the activity of the CHASEGP polypeptide in the presence of a test substance and compare with historical value of the activity of the CHASEGP polypeptide measured previously in the absence of the test substance, and vice versa. This can be accomplished, for example, by providing the activity of the CHASEGP polypeptide on an insert or pamphlet provided with a kit for conducting the assay.

Methods for selecting substrates for a particular CHASEGP are described in the EXAMPLES, and particular chondroitinase assays are exemplified.

Combinations and kits containing the combinations optionally including instructions for performing the assays are provided. The combinations include a CHASEGP polypeptide and a substrate of the CHASEGP polypeptide to be assayed; and, optionally reagents for detecting proteolysis of the substrate. The substrates, which can be chromogenic or fluorogenic molecules, including glycosaminoglycans, subject to proteolysis by a particular CHASEGP polypeptide, can be identified empirically by testing the ability of the CHASEGP polypeptide to cleave the test substrate. Substrates that are cleaved most effectively, i.e., at the lowest concentrations and/or fastest rate or under desirable conditions, are identified.

Additionally provided herein is a kit containing the above-described combination. The kit optionally includes instructions for identifying a modulator of the activity of a CHASEGP polypeptide. Any CHASEGP polypeptide is contemplated as target for identifying modulators of the activity thereof.

2. Binding assays. Also provided herein are methods for identification and isolation of agents, particularly compounds that bind to CHASEGPs. The assays are designed to identify agents that bind to the isolated chondroitinase domain (or a protein, other than a CHASEGP polypeptide, that contains the chondroitinase domain of a CHASEGP polypeptide), and to the activated form, including the activated form derived from the full length zymogen or from an extended chondroitinase domain. The identified compounds are candidates or leads for identification of compounds for treatments of disorders and diseases involving aberrant chondroitinase activity. The CHASEGP polypeptides used in the methods include any CHASEGP polypeptide as defined herein, including the CHASEGP single chain chondroitinase domain or proteolytically active portion thereof.

A variety of methods are provided herein. These methods can be performed in solution or in solid phase reactions in which the CHASEGP polypeptide (s) or chondroitinase domain (s) thereof are linked, either directly or indirectly via a linker, to a solid support. Screening assays are described in the Examples, and these assays have been used to identify candidate compounds.

For purposes herein, all binding assays described above are provided for CHASEGP.

Methods for identifying an agent, such as a compound, that specifically binds to a CHASEGP single chain chondroitinase domain, a full-length activated CHASEGP or two chain chondroitinase domain thereof are provided herein. The method can be practiced by (a) contacting the CHASEGP with one or a plurality of test agents under conditions conducive to binding between the CHASEGP and an agent; and (b) identifying one or more agents within the plurality that specifically binds to the CHASEGP.

For example, in practicing such methods the CHASEGP polypeptide is mixed with a potential binding partner or an extract or fraction of a cell under conditions that allow the association of potential binding partners with the polypeptide. After mixing, peptides, polypeptides, proteins or other molecules that have become associated with a CHASEGP are separated from the mixture. The binding partner that bound to the CHASEGP can then be removed and further analyzed. To identify and isolate a binding partner, the entire protein, for instance the entire disclosed protein of SEQ ID No. 1 can be used. Alternatively, a fragment of the protein can be used.

A variety of methods can be used to obtain cell extracts or body fluids, such as blood, serum, urine, sweat, synovial fluid, CSF and other such fluids.

For example, cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the CHASEGP under conditions in which association of the protein with the binding partner can occur. A variety of conditions can be used, including conditions that resemble conditions found in the cytoplasm of a human cell or in a body fluid, such as blood. Features, such as osmolarity pH, temperature, and the concentration of cellular extract used, can be varied to optimize the association of the protein with the binding partner. Similarly, methods for isolation of molecules of interest from body fluids are known.

After mixing under appropriate conditions, the bound complex is separated from the mixture. A variety of techniques can be used to separate the mixture. For example, antibodies specific to a CHASEGP can be used to immunoprecipitate the binding partner complex. Alternatively, standard chemical separation techniques such as chromatography and density/sediment centrifugation can be used.

After removing the non-associated cellular constituents in the extract, the binding partner can be dissociated from the complex using conventional methods. For example, dissociation can be accomplished by altering the salt concentration or pH of the mixture.

To aid in separating associated binding partner pairs from the mixed extract, the CHASEGP can be immobilized on a solid support. For example, the protein can be attached to a nitrocellulose matrix or acrylic beads. Attachment of the protein or a fragment thereof to a solid support aids in separating peptide/binding partner pairs from other constituents found in the extract. The identified binding partners can be either a single protein or a complex made up of two or more proteins.

Alternatively, the nucleic acid molecules encoding the single chain chondroitinases can be used in a yeast two-hybrid system. The yeast two-hybrid system has been used to identify other protein partner pairs and can readily be adapted to employ the nucleic acid molecules herein described.

Another in vitro binding assay, particularly for a CHASEGP, uses a mixture of a polypeptide that contains at least the catalytic domain of one of these proteins and one or more candidate binding targets or substrates. After incubating the mixture under appropriate conditions, the ability of the CHASEGP or a polypeptide fragment thereof containing the catalytic domain to bind to or interact with the candidate substrate is assessed. For cell-free binding assays, one of the components includes or is coupled to a detectable label. The label can provide for direct detection, such as radioactivity, luminescence, optical or electron density, etc., or indirect detection such as an epitope tag, an enzyme, etc. A variety of methods can be employed to detect the label depending on the nature of the label and other assay components. For example, the label can be detected bound to the solid substrate or a portion of the bound complex containing the label can be separated from the solid substrate, and the label thereafter detected.

3. Detection of signal transduction CHASEGP, which is a membrane anchored protein, can be involved directly or indirectly in signal transduction directly as a cell surface receptor or indirectly by activating proteins, such as pro-growth factors that can initiate signal transduction.

In addition, secreted CHASEGP, such as the soluble domain of CHASEGP as described in SEQ ID NO. 6, can be involved in signal transduction either directly by binding to or interacting with a cell surface receptor or indirectly by activating proteins, such as pro-growth factors that can initiate signal transduction. Assays for assessing signal transduction are well known to those of skill in the art, and can be adapted for use with the CHASEGP polypeptide.

Assays for identifying agents that affect or alter signal transduction mediated directly or indirectly, such as via activation of a pro-growth factor, by a CHASEGP, particularly the full length or a sufficient portion to anchor the extracellular domain or a functional portion thereof of a CHASEGP on the surface of a cell are provided. Such assays include, for example, transcription based assays in which modulation of a transduced signal is assessed by detecting an effect on an expression from a reporter gene (see, e.g., U.S. Pat. No. 5,436,128).

4. Methods for Identifying Agents that Modulate the Expression a Nucleic Acid Encoding a CHASEGP Another embodiment provides methods for identifying agents that modulate the expression of a nucleic acid encoding a CHASEGP. Such assays use any available means of monitoring for changes in the expression level of the nucleic acids encoding a CHASEGP.

Assay formats can be used to monitor the ability of the agent to modulate the expression of a nucleic acid encoding a CHASEGP. For instance, mRNA expression can be monitored directly by hybridization to the nucleic acids.

Cell lines are exposed to the agent to be tested under appropriate conditions and time and total RNA or mRNA is isolated by standard procedures (see, e.g. Sambrook et al (1989) MOLECULAR CLONING: A LABORATORY MANUAL, 2nd Ed. Cold Spring Harbor Laboratory Press). Probes to detect differences in RNA expression levels between cells exposed to the agent and control cells can be prepared from the nucleic acids. It is typical, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe: target hybrid and potential probe: non-target hybrids.

For example, N-and C-terminal fragments of the CHASEGP can be expressed in bacteria and used to search for proteins which bind to these fragments. Fusion proteins, such as His-tag or GST fusion to the N-or C-terminal regions of the CHASEGP can be prepared for use as a substrate. These fusion proteins can be coupled to, for example, Glutathione-Sepharose beads and then probed with cell lysates or body fluids. Prior to lysis, the cells or body fluids can be treated with a candidate agent which can modulate a CHASEGP or proteins that interact with domains thereon. Lysate proteins binding to the fusion proteins can be resolved by SDS-PAGE, isolated and identified by protein sequencing or mass spectroscopy, as is known in the art.

Antibody probes are prepared by immunizing suitable mammalian hosts in appropriate immunization protocols using the peptides, polypeptides or proteins if they are of sufficient length (e.g., 4, 5, 6, 7, 8, 9, 10, 11, 12, 13, 14, 15, 20, 25, 30, 35, 40 or more consecutive amino acids the CHASEGP polypeptide or if required to enhance immunogenicity, conjugated to suitable carriers. Methods for preparing immunogenic conjugates with carriers, such as bovine serum albumin (BSA), keyhole limpet hemocyanin (KLH), or other carrier proteins are well known in the art. In some circumstances, direct conjugation using, for example, carbodiimide reagents can be effective; in other instances linking reagents such as those supplied by Pierce Chemical Co., Rockford, Ill., can be desirable to provide accessibility to the hapten. Hapten peptides can be extended at either the amino or carboxy terminus with a Cys residue or interspersed with cysteine residues, for example, to facilitate linking to a carrier.

Administration of the immunogens is conducted generally by injection over a suitable time period and with use of suitable adjuvants, as is generally understood in the art. During the immunization schedule, titers of antibodies are taken to determine adequacy of antibody formation.

Anti-peptide antibodies can be generated using synthetic peptides corresponding to, for example, the carboxy terminal amino acids of the CHASEGP.

Synthetic peptides can be as small as 1-3 amino acids in length, generally at least 4 or more amino acid residues long. The peptides can be coupled to KLH using standard methods and can be immunized into animals, such as rabbits or ungulates.

Polyclonal antibodies can then be purified, for example using Actigel beads containing the covalently bound peptide.

While the polyclonal antisera produced in this way can be satisfactory for some applications, for pharmaceutical compositions, use of monoclonal preparations are generally used. Immortalized cell lines which secrete the desired monoclonal antibodies can be prepared using the standard method of Kohler et al., (Nature 256:495-7 (1975)) or modifications which effect immortalization of lymphocytes or spleen cells, as is generally known. The immortalized cell lines secreting the desired antibodies are screened by immunoassay in which the antigen is the peptide hapten, polypeptide or protein.

When the appropriate immortalized cell culture secreting the desired antibody is identified, the cells can be cultured either in vitro or by production in vivo via ascites fluid. Of particular interest, are monoclonal antibodies that recognize the catalytic domain or activation cleavage site (region) of a CHASEGP.

The antibodies or fragments can also be produced. Regions that bind specifically to the desired regions of receptor also can be produced in the context of chimeras with multiple species origin.

Agents that are assayed in the above method can be randomly selected or rationally selected or designed.

The agents can be, as examples, peptides, small molecules, and carbohydrates. A skilled artisan can readily recognize that there is no limit as to the structural nature of the agents.

The peptide agents can be prepared using standard solid phase (or solution phase) peptide synthesis methods, as is known in the art. In addition, the DNA encoding these peptides can be synthesized using commercially available oligonucleotide synthesis instrumentation and produced recombinantly using standard recombinant production systems. The production using solid phase peptide synthesis is necessitated if non-gene-encoded amino acids are to be included.

I. Pharmaceutical Compositions and Modes of Administration

1. Components of the compositions. Pharmaceutical compositions containing an active CHASEGP ate provided herein. Also provided are combinations of compounds that modulate the activity of a CHASEGP polypeptide and another treatment or compound for treatment of a chondroitin sulfatase disorder, such as an antibody compound.

The CHASEGP polypeptide and a second agent can be packaged as separate compositions for administration together or sequentially or intermittently. Alternatively, they can be provided as a single composition for administration or as two compositions for administration as a single composition. The combinations can be packaged as kits.

A. CHASEGP glycoprotein inhibitors. Any CHASEGP glycoprotein inhibitors, including those described herein when used alone or in combination with other compounds, that can alleviate, reduce, ameliorate, prevent, or place or maintain in a state of remission of clinical symptoms or diagnostic markers associated with increased chondroitinase activity, including undesired and/or uncontrolled scarring, can be used in the present combinations.

In one embodiment, the CHASEGP polypeptide inhibitor is an antibody or fragment thereof that specifically reacts with a CHASEGP polypeptide or the chondroitinase domain thereof, an inhibitor of the CHASEGP polypeptide production, an inhibitor of CHASEGP polypeptide membrane-localization, or any inhibitor of the expression of or, especially, the activity of a CHASEGP polypeptide. B. Anti-angiogenic agents and anti-tumor agents. Any anti-angiogenic agents and anti-tumor agents, including those described herein, when used alone or in combination with other compounds, that can alleviate, reduce, ameliorate, prevent, or place or maintain in a state of remission of clinical symptoms or diagnostic markers associated with undesired and/or uncontrolled angiogenesis and/or tumor growth and metastasis, particularly solid neoplasms, vascular malformations and cardiovascular disorders, chronic inflammatory diseases and aberrant wound repairs, circulatory disorders, crest syndromes, dermatological disorders, or ocular disorders, can be used in the combinations. Also contemplated are anti-tumor agents for use in combination with an inhibitor of a CHASEGP polypeptide. C. Anti-tumor agents and anti-angiogenic agents of the compounds identified by the methods provided herein or provided herein can be used in combination with anti-tumor agents and/or anti-angiogenesis agents.

2. Formulations and route of administration of the compounds herein and agents can be formulated as pharmaceutical compositions, typically for single dosage administration. The concentrations of the compounds in the formulations are effective for delivery of an amount, upon administration, that is effective for the intended treatment. Typically, the compositions are formulated for single dosage administration. To formulate a composition, the weight fraction of a compound or mixture thereof is dissolved, suspended, dispersed or otherwise mixed in a selected vehicle at an effective concentration such that the treated condition is relieved or ameliorated.

Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient in the composition or can be combined with other active ingredients. Liposomal suspensions, including tissue-targeted liposomes, can also be suitable as pharmaceutically acceptable carriers. These can be prepared according to methods known to those skilled in the art. For example, liposome formulations can be prepared as described in U.S. Pat. No. 4,522,811.

The active compound is included in the pharmaceutically acceptable carrier in an amount sufficient to exert a therapeutically useful effect in the absence of undesirable side effects on the patient treated. The therapeutically effective concentration can be determined empirically by testing the compounds in known in vitro and in vivo systems, such as the assays provided herein.

The concentration of active compound in the drug composition depends on absorption, inactivation and excretion rates of the active compound, the physicochemical characteristics of the compound, the dosage schedule, and amount administered as well as other factors known to those of skill in the art.

Typically a therapeutically effective dosage is contemplated. The amounts administered can be on the order of 0.001 to 1 mg/ml, including about 0.005-0.05 mg/ml and about 0.01 mg/ml, of blood volume. Pharmaceutical dosage unit forms are prepared to provide from about 1 mg to about 1000 mg, including from about 10 to about 500 mg, and including about 25-75 mg of the essential active ingredient or a combination of essential ingredients per dosage unit form. The precise dosage can be empirically determined.

The active ingredient can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of the claimed compositions and combinations containing them.

Pharmaceutically acceptable derivatives include acids, salts, esters, hydrates, solvates and prodrug forms. The derivative is typically selected such that its pharmacokinetic properties are superior to the corresponding neutral compound.

Thus, effective concentrations or amounts of one or more of the compounds provided herein or pharmaceutically acceptable derivatives thereof are mixed with a suitable pharmaceutical carrier or vehicle for systemic, topical or local administration to form pharmaceutical compositions. Compounds are included in an amount effective for ameliorating or treating the disorder for which treatment is contemplated. The concentration of active compound in the composition depends on absorption, inactivation, excretion rates of the active compound, the dosage schedule, amount administered, particular formulation as well as other factors known to those of skill in the art.

Solutions or suspensions used for parenteral, intradermal, subcutaneous, or topical application can include any of the following components; a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; cheating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds can be used. Such methods are known to those of skill in this art, and include, but are not limited to, using cosolvents, such as dimethylsulfoxide (DMSO), using surfactants, such as TWEEN surfactant and pluronic; or dissolution in aqueous sodium bicarbonate. Derivatives of the compounds, such as prodrugs of the compounds can also be used in formulating effective pharmaceutical compositions. For ophthalmic indications, the compositions are formulated in an ophthalmically acceptable carrier. For the ophthalmic uses herein, local administration, either by topical administration or by injection are contemplated. Time-release formulations are also desirable. Typically, the compositions are formulated for single dosage administration, so that a single dose administers an effective amount.

Upon mixing or addition of the compound with the vehicle, the resulting mixture can be a solution, suspension, emulsion or other composition. The form of the resulting mixture depends upon a number of factors, including the intended mode of administration and the solubility of the compound in the selected carrier or vehicle. If necessary, pharmaceutically acceptable salts or other derivatives of the compounds are prepared.

The compound is included in the pharmaceutically acceptable carrier in an amount sufficient to exert a therapeutically useful effect in the absence of undesirable side effects on the patient treated. It is understood that number and degree of side effects depends upon the condition for which the compounds are administered. For example, certain toxic and undesirable side effects are tolerated when treating life-threatening illnesses that would not be tolerated when treating disorders of lesser consequence.

The compounds also can be mixed with other active materials, that do not impair the desired action, or with materials that supplement the desired action known to those of skill in the art. The formulations of the compounds and agents for use herein include those suitable for oral, rectal, topical, inhalational, buccal (e.g., sublingual), parenteral (e.g., subcutaneous, intramuscular, intradermal, or intravenous), transdermal administration or any route. The most suitable route in any given case depends on the nature and severity of the condition being treated and on the nature of the particular active compound which is being used. The formulations are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutical therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art.

Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof A multiple-dose form is a plurality of identical unit-dosage forms packaged in a single container to be administered in segregated unit-dose form.

Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art (see e.g., Remington's Pharmaceutical Sciences, Mack Publishing Company, Easton, Pa., 15th Edition, 1975). The composition or formulation to be administered contains a quantity of the active compound in an amount sufficient to alleviate the symptoms of the treated subject.

Dosage forms or compositions containing active ingredient in the range of 0.005% to 100% with the balance made up from non-toxic carrier can be prepared. For oral administration, the pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art.

The pharmaceutical preparation can also be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles e.g., almond oil, oily esters, or fractionated vegetable oils); and preservatives (e.g., methyl or propyl-p-hydroxybenzoates or sorbic acid).

Formulations suitable for rectal administration can be presented as unit dose suppositories. These can be prepared by admixing the active compound with one or more conventional solid carriers, for example, cocoa butter, and then shaping the resulting mixture.

Formulations suitable for topical application to the skin or to the eye generally are formulated as an ointment, cream, lotion, paste, gel, spray, aerosol and oil. Carriers which can be used include Vaseline gel, lanoline, polyethylene glycols, alcohols, and combinations of two or more thereof. The topical formulations can further advantageously contain 0.05 to 15 percent by weight of thickeners selected from among hydroxypropylmethylcellulose, methylcellulose, polyvinylpyrrolidone, polyvinyl alcohol, poly (alkylene glycols), poly/hydroxyalkyl, (meth) acrylates or poly (meth) acrylamides. A topical formulation is often applied by instillation or as an ointment into the conjunctival sac. It also can be used for irrigation or lubrication of the eye, facial sinuses, and external auditory meatus. It can also be injected into the anterior eye chamber and other places. The topical formulations in the liquid state can be also present in a hydrophilic three-dimensional polymer matrix in the form of a strip, contact lens, and the like from which the active components are released.

For administration by inhalation, the compounds for use herein can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

Formulations suitable for buccal (sublingual) administration include, for example, lozenges containing the active compound in a flavored base, usually sucrose and acacia or tragacanth; and pastilles containing the compound in an inert base such as gelatin and glycerin or sucrose and acacia.

The compounds can be formulated for parenteral administration by injection, e.g., by bolus injection or continuous infusion. Formulations for injection can be presented in unit dosage form, e.g., in ampules or in multi-dose containers, with an added preservative. The compositions can be suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water or other solvents, before use.

Formulations suitable for transdermal administration can be presented as discrete patches adapted to remain in intimate contact with the epidermis of the recipient for a prolonged period of time. Such patches suitably contain the active compound as an optionally buffered aqueous solution of, for example, 0.1 to 0.2 M concentration with respect to the active compound. Formulations suitable for transdermal administration can also be delivered by iontophoresis (see e.g., Pharmaceutical Research 3 (6), 318 (1986)) and typically take the form of an optionally buffered aqueous solution of the active compound.

The pharmaceutical compositions can also be administered by controlled release means and/or delivery devices (see e.g., in U.S. Pat. Nos. 3,536,809; 3,598,123; 3,630,200; 3,845,770; 3,847,770; 3,916,899; 4,008,719; 4,687,610; 4,769,027; 5,059,595; 5,073,543; 5,120,548; 5,354,566; 5,591,767; 5,639,476; 5,674,533 and 5,733,566).

Desirable blood levels can be maintained by a continuous infusion of the active agent as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

The efficacy and/or toxicity of the CHASEGP polypeptide inhibitor (s), alone or in combination with other agents also can be assessed by the methods known in the art (See generally, O & Apos; Reilly, Investigational New Drugs, 15: 5-13 (1997)).

The active compounds or pharmaceutically acceptable derivatives can be prepared with carriers that protect the compound against rapid elimination from the body, such as time release formulations or coatings.

Kits containing the compositions and/or the combinations with instructions for administration thereof are provided. The kit can further include a needle or syringe, typically packaged in sterile form, for injecting the complex, and/or a packaged alcohol pad. Instructions are optionally included for administration of the active agent by a clinician or by the patient.

Finally, the compounds or CHASEGP polypeptides or chondroitinase domains thereof or compositions containing any of the preceding agents can be packaged as articles of manufacture containing packaging material, a compound or suitable derivative thereof provided herein, which is effective for treatment of a diseases or disorders contemplated herein, within the packaging material, and a label that indicates that the compound or a suitable derivative thereof is for treating the diseases or disorders contemplated herein. The label can optionally include the disorders for which the therapy is warranted.

J. Methods of Treatment

The compounds identified by the methods herein are used for treating or preventing abnormal accumulations of CHASEGP substrates in an animal, particularly a mammal, including a human, is provided herein. In one embodiment, the method includes administering to a mammal an effective amount of a CHASEGP glycoprotein, whereby the disease or disorder is treated or prevented.

In an embodiment, a CHASEGP inhibitor used in the treatment or prevention is administered with a pharmaceutically acceptable carrier or excipient. The mammal treated can be a human. The inhibitors provided herein are those identified by the screening assays. In addition, antibodies and antisense nucleic acids or double-stranded RNA (dsRNA), such as RNAi, are contemplated.

1. Antisense treatment in a specific embodiment, as described hereinabove, CHASEGP polypeptide function is reduced or inhibited by CHASEGP polypeptide antisense nucleic acids, to treat or prevent excessive chondroitinase activity. The therapeutic or prophylactic use of nucleic acids of at least six nucleotides, generally up to about 150 nucleotides, that are antisense to a gene or cDNA encoding CHASEGP polypeptide or a portion thereof is provided. A CHASEGP polypeptide "antisense" nucleic acid as used herein refers to a nucleic acid capable of hybridizing to a portion of a CHASEGP polypeptide RNA (generally mRNA) by virtue of some sequence complementarity, and generally under high stringency conditions. The antisense nucleic acid can be complementary to a coding and/or noncoding region of a CHASEGP polypeptide mRNA. Such antisense nucleic acids have utility as therapeutics that reduce or inhibit CHASEGP polypeptide function, and can be used in the treatment or prevention of disorders as described supra.

The CHASEGP polypeptide antisense nucleic acids are of at least six nucleotides and are generally oligonucleotides (ranging from 6 to about 150 nucleotides including 6 to 50 nucleotides). The antisense molecule can be complementary to all or a portion of the chondroitinase domain. For example, the oligonucleotide is at least 10 nucleotides, at least 15 nucleotides, at least 100 nucleotides, or at least 125 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide can include other appending groups such as peptides, or agents facilitating transport across the cell membrane (see e.g., Letsinger et al., Proc. Natl. Acad. Sci. USA 86: 6553-6556 (1989); Lemaitre et al., Proc. Natl. Acad. Sci. USA 84: 648-652 (1987); PCT Publication No. WO 88/09810, published Dec. 15, 1988) or blood-brain barrier (see e.g., PCT Publication No. WO 89/10134, published Apr. 25, 1988), hybridization-triggered cleavage agents (see e.g., Krol et al., BioTechniques 6: 958-976 (1988)) or intercalating agents (see e.g., Zon. Pharm. Res. 5:539-549 (1988)).

The CHASEGP polypeptide antisense nucleic acid generally is an oligonucleotide, typically single-stranded DNA or RNA or an analog thereof or mixtures thereof. For example, the oligonucleotide includes a sequence antisense to a portion of a nucleic acid that encodes a huma CHASEGP polypeptide. The oligonucleotide can be modified at any position on its structure with substituents generally known in the art.

The CHASEGP polypeptide antisense oligonucleotide can include at least one modified base moiety which is selected from the group including, but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-apos-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-n-2-carboxypropyl) uracil, (ACP3) w, and 2,6-diaminopurne.

In another embodiment, the oligonucleotide includes at least one modified sugar moiety selected from the group including but not limited to arabinose, 2-fluoroarabinose, xylulose, and hexose. The oligonucleotide can include at least one modified phosphate backbone selected from a phosphorothioate, a phosphorodithioate, a phosphoramidothioate, a phosphoramidate, a phosphordiamidate, a methylphosphonate, an alkyl phosphotriester, and a formacetal or analog thereof.

The oligonucleotide can be an a-anomeric oligonucleotide. An a-anomeric oligonucleotide forms specific double-stranded hybrids with complementary RNA in which the strands run parallel to each other (Gautier et al., Nucl. Acids Res. 15: 6625-6641 (1987)).

The oligonucleotide can be conjugated to another molecule, such as, but are not limited to, a peptide, hybridization triggered cross-linking agent, transport agent or a hybridization-triggered cleavage agent. The oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al., Nucl. Acids Res. 16: 3209 (1988)), methylphosphonate oligonucleotides can be prepared by use of controlled pore glass polymer supports (Sarin et al., Proc. Natl. Acad. Sci. USA 85: 7448-7451 (1988)), etc. In a specific embodiment, the CHASEGP polypeptide antisense oligonucleotide includes catalytic RNA or a ribozyme (see, e.g., PCT International Publication WO 90/11364, published Oct. 4, 1990; Sarver et al., Science 247:1222-1225 (1990)). In another embodiment, the oligonucleotide is a 2'-0-methylribonucleotide (Inoue et al., Nucl. Acids Res. 15: 6131-6148 (1987)), or a chimeric RNA-DNA analogue Inoue et al., FEBS Lett. 215: 327-330 (1987)).

Alternatively, the oligonucleotide can be double-stranded RNA (dsRNA) such as RNAi.

In an alternative embodiment, the CHASEGP polypeptide antisense nucleic acid is produced intracellularly by transcription from an exogenous sequence.

For example, a vector can be introduced in vivo such that it is taken up by a cell, within which cell the vector or a portion thereof is transcribed, producing an antisense nucleic acid (RNA). Such a vector would contain a sequence encoding the CHASEGP polypeptide antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the CHASEGP polypeptide antisense RNA can be by any promoter known in the art to act in mammalian, including human, cells. Such promoters can be inducible or constitutive. Such promoters include but are not limited to: the SV40 early promoter region (Bernoist and Chambon, Nature 290: 304-310 (1981), the promoter contained in the 3' long terminal repeat of Rous sarcoma virus (Yamamoto et al., Ce//22: 787-797 (1980), the herpes thymidine kinase promoter (Wagner et al., Proc. Natl. Acad. Sci. USA 78:1441-1445 (1981), the regulatory sequences of the metallothionein gene (Brinster et al., Nature 296: 39-42 (1982), etc.

The antisense nucleic acids include sequence complementary to at least a portion of an RNA transcript of a CHASEGP polypeptide gene, including a human CHASEGP polypeptide gene. Absolute complementarity is not required. The amount of CHASEGP polypeptide antisense nucleic acid that is effective in the treatment or prevention of neoplastic disease depends on the nature of the disease, and can be determined empirically by standard clinical techniques.

Where possible, it is desirable to determine the antisense cytotoxicity in cells in vitro, and then in useful animal model systems prior to testing and use in humans.

2. RNA interference RNA interference (RNAi) (see, e.g. Chuang et al. (2000) Proc. Natl. Acad. Sci. USA 97:4985) can be employed to inhibit the expression of a gene encoding a CHASEGP. Interfering RNA (RNAi) fragments, particularly double-stranded (ds) RNAi, can be used to generate loss-of-CHASEGP function. Methods relating to the use of RNAi to silence genes in organisms including, mammals, C. elegans, Drosophila and plants, and humans are known (see, e.g., Fire et al. (1998) Nature 391: 806-811; Fire (1999) Trends Genet. 15: 358-363; Sharp (2001) Genes Dev. 15:485-90; Hammond et al. (2001) Nature Rev, Genet. 2:110-119; Tuschl (2001) Chem. Biochem. 2:239-245; Hamilton et al. (1999) Science 286: 950-952; Hammond et al. (2000) Nature 404:293-296; Zamore et al. (2000) Cell 101:25-33; Bernstein et al. (2001) Nature 409: 363-366; Elbashir et al. (2001) Genes Dev. 15:188-200; Elbashir et al. (2001) Nature 411:494-498; International PCT application No. WO 01/29058; International PCT application No. WO 99/32619).

Double-stranded RNA (dsRNA)-expressing constructs are introduced into a host, such as an animal or plant using, a replicable vector that remains episomal or integrates into the genome. By selecting appropriate sequences, expression of dsRNA can interfere with accumulation of endogenous mRNA encoding a CHASEGP. RNAi also can be used to inhibit expression in vitro.

Regions include at least about 21 (or 21) nucleotides that are selective (i.e. unique) for CHASEGP are used to prepare the RNAi. Smaller fragments of about 21 nucleotides can be transformed directly (i.e., in vitro or in vivo) into cells; larger RNAi dsRNA molecules are generally introduced using vectors that encode them. dsRNA molecules are at least about 21 bp long or longer, such as 50, 100, 150, 200 and longer. Methods, reagents and protocols for introducing nucleic acid molecules into cells in vitro and in vivo are known to those of skill in the art.

3. Gene Therapy in an exemplary embodiment, nucleic acids that include a sequence of nucleotides encoding a CHASEGP polypeptide or functional domains or derivative thereof are administered to promote CHASEGP polypeptide function, by way of gene therapy. Gene therapy refers to therapy performed by the administration of a nucleic acid to a subject. In this embodiment, the nucleic acid produces its encoded protein that mediates a therapeutic effect by promoting CHASEGP polypeptide function. Any of the methods for gene therapy available in the art can be used (see, Goldspiel et al., Clinical Pharmacy 12:488-505 (1993); Wu and Wu, Biotherapy 3: 87-95 (1991); Tolstoshev, An. Rev. Pharmacol. Toxicol. 32: 573-596 (1993); Mulligan, Science 260: 926-932 (1993); and Morgan and Anderson, An. Rev. Biochem. 62:191-217 (1993); TIBTECH 11 5:155-215 (1993). For example, one therapeutic composition for gene therapy includes a CHASEGP polypeptide-encoding nucleic acid that is part of an expression vector that expresses a CHASEGP polypeptide or domain, fragment or chimeric protein thereof in a suitable host. In particular, such a nucleic acid has a promoter operably linked to the CHASEGP polypeptide coding region, the promoter being inducible or constitutive, and, optionally, tissue-specific. In another particular embodiment, a nucleic acid molecule is used in which the CHASEGP polypeptide coding sequences and any other desired sequences are flanked by regions that promote homologous recombination at a desired site in the genome, thus providing for intrachromosomal expression of the CHASEGP protein nucleic acid (Koller and Smithies, Proc. Natl. Acad. Sci. USA 86: 8932-8935 (1989); Zijlstra et al., Nature 342: 435-438 (1989)).

Delivery of the nucleic acid into a patient can be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, J. Biol. Chem, 262: 4429-4432 (1987)) (which can be used to target cell types specifically expressing the receptors), etc. In another embodiment, a nucleic acid-ligand complex can be formed in which the ligand is a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO 92/20316 dated Nov. 26, 1992 (Findeis et al.); WO 93/14188 dated Jul. 22, 1993 (Clarke et al), WO 93/20221 dated Oct. 14, 1993 (Young)). Alternatively, the nucleic acid can be introduced intracellularly and incorporated within host cell DNA for expression, by homologous recombination (Koller and Smithies, Proc. Natl. Acad. Sci. USA 86: 8932-8935 (1989); Zijistra et al., Nature 342:435-438 (1989)).

In a specific embodiment, a viral vector that contains the CHASEGP polypeptide nucleic acid is used. For example, a retroviral vector can be used (see Miller et al., Meth. Enzymol. 217:581-599 (1993)). These retroviral vectors have been modified to delete retroviral sequences that are not necessary for packaging of the viral genome and integration into host cell DNA. The CHASEGP polypeptide nucleic acid to be used in gene therapy is cloned into the vector, which facilitates delivery of the gene into a patient. More detail about retroviral vectors can be found in Boesen et al., Biotherapy 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest 93: 644-651 (1994); Kiem et al., Blood 83:1467-1473 (1994); Salmons and Gunzberg, Human Gene Therapy 4:129-141 (1993); and Grossman and Wilson, Curr. Opin. In Genetics And Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5: 3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); and Mastrangeli et al., J. Clin. Invest. 91: 225-234 (1993).

Adeno-associated virus (AAV) has also been proposed for use in gene therapy (Walsh et al., Proc. Soc. Exp. Biol. Med. 204: 289-300 (1993).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, Meth. Enzymol. 217: 599-618 (1993); Cohen et al., Meth. Enzymol. 217: 618-644 (1993); Cline, Pharmac. Ther. 29: 69-92 (1985)) and can be used, provided that the necessary developmental and physiological functions of the recipient cells are not disrupted. The technique should provide for the stable transfer of the nucleic acid to the cell, so that the nucleic acid is expressible by the cell and generally heritable and expressible by its cell progeny.

The resulting recombinant cells can be delivered to a patient by various methods known in the art. In an embodiment, epithelial cells are injected, e.g., subcutaneously. In another embodiment, recombinant skin cells can be applied as a skin graft onto the patient. Recombinant blood cells (e.g., hematopoietic stem or progenitor cells) can be administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., such as stem cells obtained from bone marrow, umbilical cord blood, peripheral blood, fetal liver, and other sources thereof.

For example, a cell used for gene therapy is autologous to the patient. In an embodiment in which recombinant cells are used in gene therapy, a CHASEGP polypeptide nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment.

Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, Cell 71:973-985 (1992)).

Epithelial stem cells (ESC) or keratinocytes can be obtained from tissues such as the skin and the lining of the gut by known procedures (Rheinwald, Meth. Cell Bio. 21A: 229 (1980)). In stratified epithelial tissue such as the skin, renewal occurs by mitosis of stem cells within the germinal layer, the layer closest to the basal lamina. Stem cells within the lining of the gut provide for a rapid renewal rate of this tissue. ESC or keratinocytes obtained from the skin or lining of the gut of a patient or donor can be grown in tissue culture (Rheinwald, Meth. Cell Bio. 21A: 229 (1980); Pittelkow and Scott, CaNo. Clinic Proc. 61: 771 (1986)). If the ESC are provided by a donor, a method for suppression of host versus graft reactivity (e.g., irradiation, drug or antibody administration to promote moderate immunosuppression) also can be used.

With respect to hematopoietic stem cells (HSC), any technique which provides for the isolation, propagation, and maintenance in vitro of HSC can be used in this embodiment. Techniques by which this can be accomplished include (a) the isolation and establishment of HSC cultures from bone marrow cells isolated from the future host, or a donor, or (b) the use of previously established long-term HSC cultures, which can be allogeneic or xenogeneic.

Non-autologous HSC generally are used with a method of suppressing transplantation immune reactions of the future host/patient. In a particular embodiment, human bone marrow cells can be obtained from the posterior iliac crest by needle aspiration (see, e.g., Kodo et al., J. Clin. Invest 73:1377-1384 (1984)). For example, the HSC can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., J. Cell Physiol. 91: 335 (1977)) or Witlock-Witte culture techniques (Witlock and Witte, Proc. Natl. Acad. Sci. USA 79: 3608-3612 (1982)).

In a specific embodiment, the nucleic acid to be introduced for purposes of gene therapy includes an inducible promoter operably linked to the coding region, such that expression of the nucleic acid is controllable by controlling the presence or absence of the appropriate inducer of transcription.

3. Prodrugs A method for treating tumors is provided. The method is practiced by administering a prodrug that is cleaved at a specific site by a CHASEGP to release an active drug or precursor that can be converted to active drug in vivo. Upon contact with a cell that expresses CHASEGP activity, the prodrug is converted into an active drug. The prodrug can be a conjugate that contains the active agent, such as an anti-tumor drug, such as a cytotoxic agent, or other therapeutic agent (TA), linked to a substrate for the targeted CHASEGP, such that the drug or agent is inactive or unable to enter a cell, in the conjugate, but is activated upon cleavage. The prodrug, for example, can contain an chondroitin sulfate molecule, typically a relatively short, less than about 20 disaccharide units, that is catalytically cleaved by the targeted CHASEGP. Cytotoxic agents, include, but are not limited to, alkylating agents, antiproliferative agents and tubulin binding agents. Others include, vinca drugs, mitomycins, bleomycins and taxanes.

K. Animal Models

Transgenic animal models and animals, such as rodents, including mice and rats, cows, chickens, pigs, goats, sheep, monkeys, including gorillas, and other primates, are provided herein. In particular, transgenic non-human animals that contain heterologous nucleic acid encoding a CHASEGP polypeptide or a transgenic animal in which expression of the polypeptide has been altered, such as by replacing or modifying the promoter region or other regulatory region of the endogenous gene are provided. Such an animal can by produced by promoting recombination between endogenous nucleic acid and an exogenous CHASEGP gene that could be over-expressed or mis-expressed, such as by expression under a strong promoter, via homologous or other recombination event.

Transgenic animals can be produced by introducing the nucleic acid using any know method of delivery, including, but not limited to, microinjection, lipofection and other modes of gene delivery into a germline cell or somatic cells, such as an embryonic stem cell. Typically the nucleic acid is introduced into a cell, such as an embryonic stem cell (ES), followed by injecting the ES cells into a blastocyst, and implanting the blastocyst into a foster mother, which is followed by the birth of a transgenic animal. Generally introduction of a heterologous nucleic acid molecule into a chromosome of the animal occurs by a recombination between the heterologous CHASEGP-encoding nucleic acid and endogenous nucleic acid. The heterologous nucleic acid can be targeted to a specific chromosome. In some instances, knockout animals can be produced. Such an animal can be initially produced by promoting homologous recombination between a CHASEGP polypeptide gene in its chromosome and an exogenous CHASEGP polypeptide gene that has been rendered biologically inactive (typically by insertion of a heterologous sequence, e.g., an antibiotic resistance gene). In one embodiment, this homologous recombination is performed by transforming embryo-derived stem (ES) cells with a vector containing the insertionally inactivated CHASEGP polypeptide gene, such that homologous recombination occurs, followed by injecting the ES cells into a blastocyst, and implanting the blastocyst into a foster mother, followed by the birth of the chimeric animal ("knockout animal") in which a CHASEGP polypeptide gene has been inactivated (see Capecchi, Science 244:1288-1292 (1989)). The chimeric animal can be bred to produce homozygous knockout animals, which can then be used to produce additional knockout animals. Knockout animals include, but are not limited to, mice, hamsters, sheep, pigs, cattle, and other non-human mammals. For example, a knockout mouse is produced. The resulting animals can serve as models of specific diseases, such as cancers, that exhibit under-expression of a CHASEGP polypeptide. Such knockout animals can be used as animal models of such diseases e.g., to screen for or test molecules for the ability to treat or prevent such diseases or disorders.

Other types of transgenic animals also can be produced, including those that over-express the CHASEGP polypeptide. Such animals include "knock-in" animals that are animals in which the normal gene is replaced by a variant, such as a mutant, an over-expressed form, or other form. For example, one species', such as a rodents endogenous gene can be replaced by the gene from another species, such as from a human. Animals also can be produced by non-homologous recombination into other sites in a chromosome; including animals that have a plurality of integration events.

After production of the first generation transgenic animal, a chimeric animal can be bred to produce additional animals with over-expressed or mis-expressed CHASEGP polypeptides. Such animals include, but are not limited to, mice, hamsters, sheep, pigs, cattle and other non-human mammals. The resulting animals can serve as models of specific diseases, such as cancers, that are exhibit over-expression or mis-expression of a CHASEGP polypeptide. Such animals can be used as animal models of such diseases e.g., to screen for or test molecules for the ability to treat or prevent such diseases or disorders. In a specific embodiment, a mouse with over-expressed or mis-expressed CHASEGP polypeptide is produced.

The following examples are included for illustrative purposes only and are not intended to limit the scope of the invention.

EXAMPLE 1

Microtiter Based Chondroitinase Assays

This example provides for several, rapid assays for measurement of chondroitinase activity.
Biotinylated C6S04 Assay
The free carboxyl groups on glucuronic acid residues of chondroitin 6-sulfate from shark cartilage (Sigma) are biotinylated in a one step reaction using biotin-hydrazide (Pierce), Sulfo NHS (Pierce) and 1-Ethyl dimethylaminopropyl-carbodiimide (Sigma). This biotinylated C6O4 substrate is covalently coupled to a 96 well microtiter plate in a second reaction. At the completion of the enzyme reaction, residual substrate is detected with an avidin-peroxidase reaction that can be read in a standard ELISA plate reader. As the substrate is covalently bound to the microtiter plate, artifacts such as pH-dependent displacement of the biotinylated substrate does not occur. The sensitivity permits rapid measurement of chondroitinase activity from cultured cells and biological samples with an inter-assay variation of less than 10%.
Methods
One hundred mg of human chondroitin sulfate type C (Sigma Chemicals) was dissolved in 0.1 M MES, pH 5.0, to a final concentration of 1 mg/ml and allowed to dissolve for at least 24 hr at 4° C. prior to coupling of biotin. Sulfo-NHS (Pierce; Rockford Ill.) was added to the CS04 MES solution to a final concentration of 0.184 mg/ml. Biotin hydrazide (Pierce) was dissolved in DMSO as a stock solution of 100 mM and added to the CS04 solution to a final concentration of 1 mM. A stock solution of 1-ethyl -3-(3-dimethylaminopropyl)carbidodiimide (EDAC) was prepared as a 100 mM stock solution in distilled water and added to the CS04 biotin solution at a final concentration of 30 mM. This solution was left stirring overnight at 4° C. Unlinked biotin and EDAC were removed by dialysis against water with 3 changes of 1000× volume of water. The dialyzed, biotinylated CS04 (bCS04) was aliquoted and stored at −20° C. for up to several months.

Sulfo-NHS was diluted to 0.184 mg/ml in water with the bCS04 at a concentration of 0.2 mg/ml and pipetted into 96 well COVALINK-NH plates (NUNC; Placerville N.J.) at 50 µl per well. EPAC was diluted to 0.123 mg/ml in water and pipetted into the COVALINK-NH plates with the bCS04 solution resulting in a final concentration of 10 µg/well bCS04 and 6.15 µg/well EDAC. The plates were incubated overnight at 4° C. or for 2 hr at 23° C., which gave comparable results. After covalent immobilization of bCS04 on the microtiter plates, the coupling solution was removed by shaking and the plates were washed 3 times in PBS containing 2M NaCl and 50 mM MgSO4 (Buffer A). The plates could be stored at 4° C. for up to one week.

The COVALINK-NH plates with immobilized bCS04 were equilibrated with 100 µl/well assay buffer—either 0.1 M formate, pH 3.7, 0.1 M NaCl, 1% TRITON X-100 detergent, 5 mM saccharolactone for lysosomal chondroitinase; or 0.1 M formate pH 4.5, 0.15 M NaCl, 1% TRTTON X-100 detergent, 5 mM saccharolactone for neutral-active enzymes. A set of standards for the calibration of enzyme activity against "relative Turbidity Reducing Units" (rTRU's) was generated by diluting bovine testicular hyaluronidase (Sigma Type VI-S) in neutral enzyme buffer from 1.0 to $1 \times 10^6$ rTRU/well and assaying 100 µl/well in triplicate. Samples of acid-active Chondroitinase were diluted in lysosomal assay buffer from 1:10 to 1:130,000 were pipetted in triplicate at 100 µl/well. For most assays of tissue extracts and human plasma, a 30 min incubation at 37° C. was sufficient. Positive and negative control wells (no enzyme or no ABC (see below), respectively) were included in triplicate.

The reaction was terminated by the addition of 200 µl/well of 6M Guanidine HCl followed by three washes of 300 µl/well with PBS, 2 M NaCl, 50 MM $MgSO_4$, 0.05% TWEEN 20 detergent (Buffer B). An avidin biotin complex (ABC) kit (Vector Labs; Burlingame Calif.) was prepared in 10 ml of PBS containing 0.1% TWEEN 20 detergent, which was pre-incubated for 30 min at room temperature during the incubation. The ABC solution was added (100 µl/well) and incubated for 30 min at room temperature. The plate was washed five times with Buffer B, then an o-phenylenediamine (OPD) substrate was added at 100 µl/well by dissolving one 10 mg tablet of OPD in 10 ml of 0.1 M citrate-$PO_4$ buffer, pH 5.3 and adding 7.5 μl of 30% $H_2O_2$. The plate was incubated in the dark for 10-15 min, then read using a 492 nm filter in an ELISA plate reader (Titertek Multiskan PLUS; ICN) monitored by computer using the Delta Soft II plate reader software from Biometallics (Princeton N.J.). A standard curve using the bovine testicular hyaluronidase was generated by a four parameter curve fit of the commercial hyaluronidase preparation and unknown samples were interpolated through their absorbance at 492 nm.

To analyze pH dependence of chondroitinases, purified recombinant CHASEGP and bovine testicular hyaluronidase are used. The pH dependence of enzyme activity is measured by diluting purified CHASEGP or partially purified bovine testicular hyaluronidase to 0.1 rTRU in the following buffers: 50 mM formate, pH 3-4.5; 50 mM acetate, pH 5-6; 50 mM MES, pH 6-7; or 50 mM HEPES, pH 7-8. Samples are assayed for 30 min at 37° C. and activity was expressed as a percent of maximal activity. NaCl was not used in buffers, as it can alter the pH optima of testicular hyaluronidase preparations (Gold, Biochem. J. 205:69-74, 1982; Gacesa et al. Biochem. Soc, Trans. 7:1287-1289, 1979); physiological salt concentrations (0.15 M) decreased the apparent pH optimum, an effect that was more pronounced in purified preparations of the testicular enzyme than in the original crude sample.
Results Chondroitin-6 sulfate from shark cartilage was biotinylated in a one step reaction using biotin-hydrazide and EDAC. By limiting the EDAC, which couples the free carboxyl groups on C604 with biotin hydrazide, only a small fraction of the total glucuronic acid residues on C604 were labeled. This amount of EDAC ($3 \times 10^{-5}$ M) added to C604 ($2.8 \times 10^{-3}$ M) results in a maximum of one molecule of biotin hydrazide coupled per 93 disaccharide units of C604.

A four-parameter curve fit of bacterial chondroitinase (Seiakagaku, JP) diluted from 1.0 to $1 \times 10^{-6}$ U/well, was prepared. Four parameter curve fits were established from the equation $y=((A-D)/(1+(conc/C)^B))+D$ where logit $y=\ln(y^1/1-y^1)$, $y^1=(y-D)/(A-D)$, $B=b/\ln 10$ and $C=EXP(a/B)$. The four parameters (A,B,C,D) were calculated with a software program that utilized the 2+2 algorithm with linear regression (Rodbard et al, Clin. Chem. 22:350, 1976). This curve fit incorporates the sigmoidal aspects the standard curve. A standard logarithmic curve also can be utilized over a shorter range of values to establish a standard curve fit.

EXAMPLE 2

Other Glycosamnoglycan Degrading Enzyme Assays

In addition to the microtiter based assay using Chondroitin4 and 6 Sulfate, the substrate specificity of CHASEGP towards other glycosaminoglycans or proteoglycans can be tested using a gel shift assay with purified substrates.

Many glycosaminoglycan-degrading enzyme assays have been based upon the measurement of the generation of new reducing N-acetylamino groups (Bonner and Cantey, Clin. Chim. Acta 13:746-752, 1966), or loss of viscosity (De Salegui et sl., Arch. Biochem. Biophys. 121:548-554, 1967) or turbidity (Dorfman and Ott, J. Biol Chem. 172:367, 1948). With purified substrates all of these methods suffice for determination of the presence or absence of endoglucosamidic activity.
Methods Gel shift assay-Purified substrates are mixed with recombinant CHASEGP to test for endoglucosidase activity that results in a shift in substrate mobility within the gel. Chondroiti-4 and 6 sulfate, dernatan sulfate, heparan-sulfate are obtained from Sigma Chemical. Each test substrate is diluted to 0.1 mg/ml in a buffer range from pH 3.5-7.5. 10 ul samples of purified CHASEGP or conditioned media from CHASEGP expressing cells as well as are mixed with 90 ul of test substrate in desired buffer and incubated for 3 hours at 37 C. Following incubation samples are neutralized with sample buffer (Tris EDTA PH 8.0, Bromophenol Blue and glycerol) followed by electrophoresis. Glycosaminoglycans are detected by staining the gels in 0.5% Alcian Blue in 3% Glacial Acetic Acid overnight followed by destaining in 7% Glacial Acetic Acid. Degradation is determined by comparison substrate mobility in the presence and absence of enzyme.

Other methods for the detection of chondroitinase activity include modification of an Alcian Blue assay for hyaluronidase activity (Pryce-Jones, R. H., and Lannigan, N. A. (1997) J. Pharm. Pharmacol. 31, 92P). Hyaluronan is substituted for chondroitin 4 or 6 sulfate and non precipitated alcian blue in solution becomes visible with increased enzyme activity.

EXAMPLE 3

Cloning of CHASEGP cDNA

The following example provides methods for obtaining CHASEGP cDNA suitable for the expression of recombinant protein in a heterologous system. These methods do not include the 624 bp 5' untranslated region (UTR) that can be inhibitory for proper gene expression in some cell types as is found with the UTR in the HYAL1 gene.

The CHASEGP cDNA was determined to be 2414 nucleotides in length containing an open reading frame of 1445 nucleotides. There is an AUG translation initiation codon at nucleotides 642-644 that is not in a strong context for translation but and an upstream stop codon at nucleotides 624-626. The 5' UTR is unusually large, which inhibit translation by preventing the ribosome from binding to the correct initiating methionine codon. Csoka et al (Genomics. Sep. 15, 1999;60 (3):356-61.) al demonstrated that by northern blot, transcripts for CHASEGP in skeletal muscle showed a band approximately 400 bp shorter than that in placenta. The CHASEGP isoform in skeletal muscle does not contain this large UTR and is more efficiently translated. The protein is predicted to consist of 481 amino acids SEQ ID No. 1 with a calculated molecular mass of 54 kDa. Overall, the CHASEGP cDNA coding sequence is 57% identical to human SPAM1, and the amino acid identity is 44%.

The majority of the CHASEGP open reading frame was obtained from an approximately 1.8 kb I.M.A.G.E. Consortium Clone from a human placental library (GenBank Acc. No. 140198). This clone contains the entire CHASEGP open reading frame minus the initiation codon and lysine at positions 1 and 2, respectively. Miniprep plasmid DNA isolated from clone 140198 was amplified by PCR using a forward primer including a Met and Lys and a reverse primer including the stop codon of human CHASEGP. The resultant PCR product was gel purified and cloned into a Topo cloning vector to yield the CHASEGP ORF. Positive clones identified by PCR and DNA sequencing were then be utilized for construction of CHASEGP expression plasmids.

EXAMPLE 4

Generation of a CHASEGP Expression Plasmid

The following example provides methods for generation of a catalytically active secreted recombinant CHASEGP expression vector capable of glycosylation in mammalian cells.

CHASEGP constructs and primer design-Wild type GPI anchored CHASEGP was PCR amplified from a CHASEGP clone in PCRII vector with flanking 5'-NheI(SEQ ID NO. 7) and 3'-BamH1 (SEQ ID NO. 8) primers and cloned between compatible NheI and BamH1 sites in IresPuro2 vector (Clontech, Palo Alto Calif.). In order to construct secreted forms of CHASEGP, truncation mutants lacking the hydrophobic C terminal are constructed. Using a GPI cleavage prediction program the GPI anchor cleavage site was located around amino acid position 457 in the full-length protein. A set of seven 3' primers were used to construct a set of seven progressively truncated deletion mutants starting at position 457 and deleted progressively by one amino acid. These primers were designed to have compatible NheI (5') and BamH1 (3') sites to clone the truncation mutants in vector Irespuro2 either untagged with a stop codon in the 3' primer, or as a C terminus His tagged protein for ease of purification and detection. Reverse primers SEQ ID NO. 9, SEQ ID NO. 10, and SEQ ID NO. 11 were used to generate deletion mutants ending at position 457, 456 and 455 without a 6 His tag. Other mutant primers were generated with the same base design with the appropriate modifications to include and exclude the particular amino acids. For generating his tagged variants the same set of primers are used except that primers lack the stop codon in the respective reverse primers, the forward primer remaining the same. Overlapping primers were used to construct a six amino acid spacer followed by six Histidine within BamH1 and Not1 sites in Irespuro2 such that His tagged mutants were generated by ligation of the PCR amplified and restriction digested products within the NheI and BamH1 sites in the his tag containing Irespuro2 vector.

For sequencing PCR products, bands were excised, and eluted with the Gel Extraction Kit (Boehringer Mannheim). All sequencing reactions were performed on double stranded DNA with the Taq dye deoxy terminator cycle sequencing kit (Applied Biosystems) according to the manufacturer's instructions, and run on an ABI Prism™ automated sequencer (Applied Biosystems).

Although the invention has been described with reference to the above example, it will be understood that modifications and variations are encompassed within the spirit and scope of the invention. Accordingly, the invention is limited only by the following claims.

What is claimed is:

1. An isolated nucleic acid molecule encoding a C-terminal truncated mammalian chondroitinase polypeptide, wherein:
the nucleic acid molecule consists of a sequence of nucleotides that encodes a truncated polypeptide consisting of the sequence of amino acids set forth in SEQ ID NO:6 or a sequence of amino acids that has at least 96% sequence identity to a polypeptide consisting of the sequence of amino acids set forth in SEQ ID NO:6, wherein the encoded truncated polypeptide is soluble and has chondroitinase activity.

2. The isolated nucleic acid molecule of claim 1 that consists of a sequence of nucleotides selected from among:
(a) a sequence of nucleotides set forth as SEQ ID NO.5;
(b) a sequence of nucleotides that has at least 96% sequence identity to a nucleic acid molecule consisting of the sequence set forth in SEQ IDNO: 5; and
(c) a sequence of nucleotides comprising degenerate codons of (a) or (b).

3. A vector, comprising the nucleic acid molecule of claim 1, wherein the vector encodes and directs expression of the truncated polypeptide.

4. The vector of claim 3 that is a eukaryotic vector.

5. The vector of claim 3, wherein the nucleic acid molecule is operably linked to a sequence of nucleotides that directs secretion of the encoded polypeptide.

6. The isolated nucleic acid molecule of claim 1 that consists of the sequence of nucleotides set forth in SEQ ID NO:5.

7. The isolated nucleic acid molecule of claim 1 that consists of the sequence of nucleotides set forth in SEQ ID NO:5 or a portion thereof that encodes a catalytically active polypeptide.

8. The isolated nucleic acid molecule of claim 1 that consists of a sequence of nucleotides that encodes a truncated polypeptide consisting of the sequence of amino acid residues set forth in SEQ ID NO:6.

9. an isolated cell or a cell culture, comprising a vector of claim 3.

10. The cell of claim 9 that is a prokaryotic cell or a eukaryotic cell.

11. The cell of claim 9 that is a mammalian cell.

12. The isolated nucleic acid molecule of claim 1 that is cDNA.

13. The isolated nucleic acid molecule of claim 8 that is cDNA.

14. A vector, comprising the nucleic acid molecule of claim 8, wherein the vector encodes and directs expression of the truncated polypeptide.

* * * * *

UNITED STATES PATENT AND TRADEMARK OFFICE
CERTIFICATE OF CORRECTION

PATENT NO.         : 8,815,558 B2
APPLICATION NO.    : 12/475221
DATED              : August 26, 2014
INVENTOR(S)        : Frost et al.

It is certified that error appears in the above-identified patent and that said Letters Patent is hereby corrected as shown below:

IN THE SPECIFICATION:

At column 1, line 33, please replace "dernatan sulfate" with —dermatan sulfate—;

At column 3, line 13, please replace "Yosbida" with —Yoshida—;

At column 3, line 61, please replace "glycsoyl-hydrolase" with —glycosyl-hydrolase—;

At column 5, line 15, please replace "mus musculus" with —*Mus musculus*—;

At column 6, line 17, please replace "affects" with —effects—;

At column 6, line 38, please replace "fell" with —fall—;

At column 7, line 62, please replace "set form as" with —set forth as—;

At column 9, line 28, please replace "glycosaminoglyan" with —glycosaminoglycan—;

At column 9, line 40, please replace "CHASEFP" with —CHASEGP—;

At column 9, lines 63, please replace "N-terninal" with —N-terminal—;

At column 10, lines 30-31, please replace "Carillo et Al. (1988) et al. (1988) Slam J Applied Math 48, 1073" with —Carrillo et al. (1988) SIAM J Applied Math 48, 1073—;

At column 10, line 46, please replace "progran" with —program—;

At column 10, line 48, please replace "evereux" with —Devereux—;

At column 10, line 52, please replace "Carillo" with —Carrillo—;

At column 11, line 67, please replace "therapeutical" with —therapeutically—;

At column 14, line 13, please replace "Gin" with —Gln—;

At column 14, line 14, please replace "Gin" with —Gln—;

At column 14, line 15, please replace "Gin" with —Gln—;

At column 15, line 29, please replace "variable light chain V," with —variable light chain VL—;

At column 18, line 4, please replace "pepidomimetics" with —peptidomimetics—;

Signed and Sealed this
Twenty-fourth Day of February, 2015

Michelle K. Lee
*Deputy Director of the United States Patent and Trademark Office*

CERTIFICATE OF CORRECTION (continued)
U.S. Pat. No. 8,815,558 B2

At column 19, line 45, please replace "labled" with —labeled—;

At column 21, line 67, please replace "fell" with —fall—;

At column 22, line 47, please replace "acetamindo" with —acetamido—;

At column 25, line 27, please replace "isolectric" with —isoelectric—;

At column 25, line 38, please replace "CDNA" with —cDNA—;

At column 27, line 13, please replace "Bemoist" with —Benoist—;

At column 27, line 16, please replace "Ce//22" with —Cell 22—;

At column 27, line 27, please replace "Herrar-Estrella" with —Herrera-Estrella—;

At column 27, line 29, please replace "Garder" with —Gardner—;

At column 27, line 50, please replace "Pinckert" with —Pinkert—;

At column 28, line 59, please replace "phosphinotricin" with —phosphinothricin—;

At column 31, line 22, please replace "3-amino propionoic acid" with —3-amino propanoic acid—;

At column 32, line 3, please replace "heterobifonctional" with —heterobifunctional—;

At column 32, lines 42-43, please replace "ET A/." with —et al.—;

At column 34, line 6, please replace "SCHASEGP" with —CHASEGP—;

At column 34, line 52, please replace "fee CHASEGP" with —the CHASEGP—;

At column 36, line 30, please replace "Ce//22" with —Cell 22—;

At column 42, line 9, please replace "acaciagelatin" with —acacia gelatin—;

At column 42, line 10, please replace "polvinylpyrrolidine" with —polyvinylpyrrolidine—;

At column 42, line 22, please replace "cyclodextrine" with —cyclodextrin—;

At column 45, line 39, please replace "diaminopurne" with —diaminopurine—;

At column 51, line 66, please replace "C604" with —C6SO4—;

At column 52, line 19, please replace "carbidodiimide" with —carbodiimide—;

At column 52, line 29, please replace "EPAC" with —EDAC—;

At column 52, line 43, please replace "TRTTON" with —TRITON—;

At column 52, line 58, please replace "50 MM" with —50 mM—;

At column 53, line 29, please replace "C604" with —C6SO4—;

At column 53, line 30, please replace "C604" with —C6SO4—;

At column 53, line 31, please replace "C604" with —C6SO4—;

At column 53, line 33, please replace "C604" with —C6SO4—;

At column 53, line 58, please replace "et sl.," with —et al.,—.

At column 53, line 65, please replace "endoglucosidase" with —endoglycosidase—;

At column 53, line 67, please replace "dernatan" with —dermatan—.

CERTIFICATE OF CORRECTION (continued)
U.S. Pat. No. 8,815,558 B2

IN THE CLAIMS:

Column 71, lines 12 to 19 should read,

2. The isolated nucleic acid molecule of claim 1 that consists of a sequence of nucleotides selected from among:

(a) a sequence of nucleotides set forth as SEQ ID NO:5;

(b) a sequence of nucleotides that has at least 96% sequence identity to a nucleic acid molecule consisting of the sequence set forth in SEQ ID NO:5; and (c) a sequence of nucleotides comprising degenerate codons of (a) or (b).

Column 72, lines 11 to 12 should read,

9. An isolated cell or a cell culture, comprising a vector of claim 3.

UNITED STATES PATENT AND TRADEMARK OFFICE
CERTIFICATE OF CORRECTION

| | | |
|---|---|---|
| PATENT NO. | : 8,815,558 B2 | Page 1 of 1 |
| APPLICATION NO. | : 12/475221 | |
| DATED | : August 26, 2014 | |
| INVENTOR(S) | : Frost et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 161 days.

Signed and Sealed this
Twenty-first Day of July, 2015

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 481
<212> TYPE: PRT
<213> ORGANISM: Homo sapiens

<400> SEQUENCE: 1

Met Lys Val Leu Ser Glu Gly Gln Leu Lys Leu Cys Val Val Gln Pro
1               5                   10                  15

Val His Leu Thr Ser Trp Leu Leu Ile Phe Phe Ile Leu Lys Ser Ile
            20                  25                  30

Ser Cys Leu Lys Pro Ala Arg Leu Pro Ile Tyr Gln Arg Lys Pro Phe
        35                  40                  45

Ile Ala Ala Trp Asn Ala Pro Thr Asp Gln Cys Leu Ile Lys Tyr Asn
    50                  55                  60

Leu Arg Leu Asn Leu Lys Met Phe Pro Val Ile Gly Ser Pro Leu Ala
65                  70                  75                  80

Lys Ala Arg Gly Gln Asn Val Thr Ile Phe Tyr Val Asn Arg Leu Gly
                85                  90                  95

Tyr Tyr Pro Trp Tyr Thr Ser Gln Gly Val Pro Ile Asn Gly Gly Leu
            100                 105                 110

Pro Gln Asn Ile Ser Leu Gln Val His Leu Glu Lys Ala Asp Gln Asp
        115                 120                 125

Ile Asn Tyr Tyr Ile Pro Ala Glu Asp Phe Ser Gly Leu Ala Val Ile
    130                 135                 140

Asp Trp Glu Tyr Trp Arg Pro Gln Trp Ala Arg Asn Trp Asn Ser Lys
145                 150                 155                 160

Asp Val Tyr Arg Gln Lys Ser Arg Lys Leu Ile Ser Asp Met Gly Lys
                165                 170                 175

Asn Val Ser Ala Thr Asp Ile Glu Tyr Leu Ala Lys Val Thr Phe Glu
            180                 185                 190

Glu Ser Ala Lys Ala Phe Met Lys Glu Thr Ile Lys Leu Gly Ile Lys
        195                 200                 205

Ser Arg Pro Lys Gly Leu Trp Gly Tyr Tyr Leu Tyr Pro Asp Cys His
    210                 215                 220
```

```
Asn Tyr Asn Val Tyr Ala Pro Asn Tyr Ser Gly Ser Cys Pro Glu Asp
225                 230                 235                 240

Glu Val Leu Arg Asn Asn Glu Leu Ser Trp Leu Trp Asn Ser Ser Ala
            245                 250                 255

Ala Leu Tyr Pro Ser Ile Cys Val Trp Lys Ser Leu Gly Asp Ser Glu
        260                 265                 270

Asn Ile Leu Arg Phe Ser Lys Phe Arg Val His Glu Ser Met Arg Ile
    275                 280                 285

Ser Thr Met Thr Ser His Asp Tyr Ala Leu Pro Val Phe Val Tyr Thr
290                 295                 300

Arg Leu Gly Tyr Arg Asp Glu Pro Leu Phe Phe Leu Ser Lys Gln Asp
305                 310                 315                 320

Leu Val Ser Thr Ile Gly Glu Ser Ala Ala Leu Gly Ala Ala Gly Ile
            325                 330                 335

Val Ile Trp Gly Asp Met Asn Leu Thr Ala Ser Lys Ala Asn Cys Thr
        340                 345                 350

Lys Val Lys Gln Phe Val Ser Ser Asp Leu Gly Ser Tyr Ile Ala Asn
    355                 360                 365

Val Thr Arg Ala Ala Glu Val Cys Ser Leu His Leu Cys Arg Asn Asn
370                 375                 380

Gly Arg Cys Ile Arg Lys Met Trp Asn Ala Pro Ser Tyr Leu His Leu
385                 390                 395                 400

Asn Pro Ala Ser Tyr His Ile Glu Ala Ser Glu Asp Gly Glu Phe Thr
            405                 410                 415

Val Lys Gly Lys Ala Ser Asp Thr Asp Leu Ala Val Met Ala Asp Thr
        420                 425                 430

Phe Ser Cys His Cys Tyr Gln Gly Tyr Glu Gly Ala Asp Cys Arg Glu
    435                 440                 445

Ile Lys Thr Ala Asp Gly Cys Ser Gly Val Ser Pro Ser Pro Gly Ser
450                 455                 460

Leu Met Thr Leu Cys Leu Leu Leu Ala Ser Tyr Arg Ser Ile Gln
465                 470                 475                 480

Leu

<210> SEQ ID NO 2
<211> LENGTH: 481
<212> TYPE: PRT
<213> ORGANISM: Mus musculus
<220> FEATURE:
<221> NAME/KEY: SIGNAL
<222> LOCATION: (1)..(34)

<400> SEQUENCE: 2

Met Gln Leu Leu Pro Glu Gly Gln Leu Arg Leu Cys Val Phe Gln Pro
1               5                   10                  15

Val His Leu Thr Ser Gly Leu Leu Ile Leu Phe Ile Leu Lys Ser Ile
            20                  25                  30

Ser Ser Leu Lys Pro Ala Arg Leu Pro Val Tyr Gln Arg Lys Pro Phe
        35                  40                  45

Ile Ala Ala Trp Asn Ala Pro Thr Asp Leu Cys Leu Ile Lys Tyr Asn
    50                  55                  60

Leu Thr Leu Asn Leu Lys Val Phe Gln Met Val Gly Ser Pro Arg Leu
65                  70                  75                  80

Lys Asp Arg Gly Gln Asn Val Val Ile Phe Tyr Ala Asn Arg Leu Gly
            85                  90                  95
```

Tyr Tyr Pro Trp Tyr Thr Ser Glu Gly Val Pro Ile Asn Gly Gly Leu
            100                 105                 110

Pro Gln Asn Thr Ser Leu Gln Val His Leu Lys Gly Ala Gly Gln Asp
            115                 120                 125

Ile Asn Tyr Tyr Ile Pro Ser Glu Asn Phe Ser Gly Leu Ala Val Ile
130                 135                 140

Asp Trp Glu Tyr Trp Arg Pro Gln Trp Ala Arg Asn Trp Asn Thr Lys
145                 150                 155                 160

Asp Ile Tyr Arg Gln Lys Ser Arg Thr Leu Ile Ser Asp Met Lys Glu
            165                 170                 175

Asn Ile Ser Ala Ala Asp Ile Glu Tyr Ser Ala Lys Ala Thr Phe Glu
            180                 185                 190

Lys Ser Ala Lys Ala Phe Met Glu Glu Thr Ile Lys Leu Gly Ser Lys
            195                 200                 205

Ser Arg Pro Lys Gly Leu Trp Gly Tyr Tyr Leu Tyr Pro Asp Cys His
            210                 215                 220

Asn Tyr Asn Val Tyr Ala Thr Asn Tyr Thr Gly Ser Cys Pro Glu Glu
225                 230                 235                 240

Glu Val Leu Arg Asn Asn Asp Leu Ser Trp Leu Trp Asn Ser Ser Thr
            245                 250                 255

Ala Leu Tyr Pro Ala Val Ser Ile Arg Lys Ser Phe Ala Asp Ser Glu
            260                 265                 270

Asn Thr Leu His Phe Ser Arg Phe Arg Val Arg Glu Ser Leu Arg Ile
            275                 280                 285

Ser Thr Met Thr Ser Gln Asp Tyr Ala Leu Pro Val Phe Val Tyr Thr
            290                 295                 300

Gln Leu Gly Tyr Lys Glu Glu Pro Leu Leu Phe Pro Phe Lys Gln Asp
305                 310                 315                 320

Leu Ile Ser Thr Ile Gly Glu Ser Ala Ala Leu Gly Ala Ala Gly Ile
            325                 330                 335

Val Val Trp Gly Asp Met Asn Leu Thr Ser Ser Glu Glu Asn Cys Thr
            340                 345                 350

Lys Val Asn Arg Phe Val Asn Ser Asp Phe Gly Ser Tyr Ile Ile Asn
            355                 360                 365

Val Thr Arg Ala Ala Glu Val Ser Ser Arg His Leu Cys Lys Asn Asn
            370                 375                 380

Gly Arg Cys Val Arg Lys Thr Trp Lys Ala Ala His Tyr Leu His Leu
385                 390                 395                 400

Asn Pro Ala Ser Tyr His Ile Glu Ala Ser Glu Asp Gly Glu Phe Ile
            405                 410                 415

Val Arg Gly Arg Ala Ser Asp Thr Asp Leu Ala Val Met Ala Glu Asn
            420                 425                 430

Phe Leu Cys His Cys Tyr Glu Gly Tyr Glu Gly Ala Asp Cys Arg Glu
            435                 440                 445

Met Thr Glu Ala Ser Gly Pro Ser Gly Leu Ser Leu Ser Ser Ser Ser
            450                 455                 460

Val Ile Thr Leu Cys Leu Leu Val Leu Ala Gly Tyr Gln Ser Ile Gln
465                 470                 475                 480

Leu

<210> SEQ ID NO 3
<211> LENGTH: 2414
<212> TYPE: DNA

<213> ORGANISM: Homo sapiens

<400> SEQUENCE: 3

```
cgcccgggca ggtctttatt ttatttatgc tatctatttc ttttccttt ttttttttt      60
tttttgagat gaagtcttac tctgttgccc aggctggagt gtagtggtgt gatctcggct    120
cgctgcagcc actgcctcct gggttcaggt gattctcctg acttagcctc ctgagtggct    180
gggactgcag gagcatgcca tcatgcccag ctgattttg tattttagt agagatgggg      240
tttcaccgtg ttggccagaa tggtttgcat tcctgacctc aagtgatctg cctgcctcag    300
cctcccaaaa tgttgggtac aggggtgagc accgtgcct tgctattaat gccatctatt     360
tcactgaaga ttccgcctct catttcttga gtcatttttt ttaaatttcc ttaaattgga    420
cttcacattt tctgatgcct ccttgtttag cttaataact gaccttctga attcttttt    480
aggaaaatca ggaatttctt cttggtttgg agccattgct ggacatcctt tgccattcaa    540
cctctgattt gcacaaggtg actaaaggac cagcagcaaa caaaacgttt ggtcttctag    600
agtgcactaa agcagaagat acgtaacatt tttatcttac catgaaagta ttatctgaag    660
gacagttaaa gctttgtgtt gttcaaccag tacatctcac ttcatggctc cttatatttt    720
ttattctaaa gtctatctct tgtctaaaac ctgctcgact tccaattat caaaggaaac      780
cttttatagc tgcttggaat gctccaacag atcagtgttt gataaaatat aattttaagac   840
taaatttgaa aatgtttcct gtgattggaa gcccactggc caaggccagg gggcaaaatg    900
tcactatatt ttatgtcaac agattgggat actatccgtg gtatacatca caggggggtcc   960
ccattaatgg aggtctccca cagaacataa gttacaagt acatctggaa aaagctgacc    1020
aagatattaa ttattacatc cctgctgaag atttcagtgg acttgctgtt atagattggg    1080
aatattggag accacagtgg gcccggaact ggaactcaaa agatgtttac agacagaagt    1140
caagaaagct tatttccgat atgggaaaga atgtatcagc taccgatatt gaatatttag    1200
ccaaagtgac ctttgaagaa agtgcaaaag ctttcatgaa ggaaaccatc aaattgggaa    1260
ttaagagccg acccaaaggc ctttggggtt attatttata tcctgattgc cacaattata    1320
acgtttatgc cccaaactac tctgggtcat gcccagaaga cgaagtcttg aggaacaatg    1380
agctctcttg gctctggaac agcagtgctg ctttatatcc ttctatctgt gtctggaaat    1440
cccttggaga cagtgaaaac attttgcgct tctccaaatt tcgggtgcat gaatccatga    1500
ggatctccac catgacatct catgattatg ctctgcctgt atttgtctac acaaggctag    1560
ggtacagaga tgaaccttta ttttcctttt ctaagcaaga tctagtcagc accataggag    1620
aaagtgctgc cttgggagct gcaggcattg ttatttgggg agacatgaat ttaactgcat    1680
ccaaggccaa ctgtacaaag gtgaagcagt tgtgagttc tgatttaggg agctacatag    1740
ccaatgtgac cagagctgct gaggtatgca gccttcacct ctgcaggaac aatggcaggt    1800
gcataaggaa gatgtggaac gcgcccagtt accttcactt gaaccctgca agttaccaca    1860
tagaggcctc tgaggacggg gagtttactg tgaaaggaaa agcatctgat acagacctgg    1920
cagtgatggc agatacattt tcctgtcatt gttatcaggg atatgaagga gctgattgca    1980
gagaaataaa gacggctgat ggctgctctg ggtttcccc ttctcctggt tcactaatga    2040
cactttgtct actgctttta gcaagttatc gaagcattca gttgtgagat aattgagttt    2100
aaagggaatt gtgtggcctc tagcctagtc atttaaagaa ggatgtaact tataacattt    2160
tttttctctt atgaattcta ttgagagata ttataagtag acattatgta tgtcacttaa    2220
cataaacaga aacattattt tatttgcctc cagtctggct aggaaaccag atctggggta    2280
```

```
aagtcaatgt acacttcctc cttattggaa tatttaagtt gcatttaaac taaaactagt    2340
ataatttagt cttttcatga atgtacatac ataaaattat acataaaaat attaaattat    2400
tcatttcaaa aaaa                                                      2414
```

<210> SEQ ID NO 4
<211> LENGTH: 3255
<212> TYPE: DNA
<213> ORGANISM: Mus musculus

<400> SEQUENCE: 4

```
tggctctgga gcaggtgaat aaaggaccag caggcaaaca aaagcaaagg ttttaaaca      60 tagtttatca cagctgttct gctgagagga gagtggcttt ttcactaact ccagtctata    120
tgtggcaaac ctgtctccac ccaaggaata gctattcacc tttttcgcta actggaagag    180
tgaaccaaag aggccttttg gattacgttg aagaaaggt agtgaaggtt ctatcttatc     240
atgcaactat tgcctgaagg acaattaaga ctctgtgttt ttcaaccagt acatcttaca    300
tcggggctgc tcatactttt tatcctgaag tctatctcat ccctaaaacc tgcccgactt    360
ccagtttatc aaaggaaacc ttttattgct gcttggaatg ctccaacaga cctgtgtttg    420
ataaaatata atttaacact gaacttaaaa gtgtttcaga tggttggaag ccctcggctc    480
aaagacaggg ggcaaaatgt tgttatattt tatgccaaca gattgggata ttacccatgg    540
tatacatcag aagggtacc catcaatggt ggtcttcccc aaaacacaag cttacaagta     600
cacctgaaag gggctggcca ggatattaat tattacatcc cttctgaaaa tttcagtgga    660
cttgctgtta tagactggga atattggcgc ccacagtggg cccggaactg gaacacaaag    720
gatatctaca gacagaagtc aagaactctt atttctgata tgaaagagaa catatctgct    780
gctgatattg aatattcagc caaggcaact tttgagaaaa gtgcaaaagc tttcatggag    840
gaaactatca aattgggaag taagagcaga cccaagggcc tttggggtta ttatttatat    900
cctgattgcc acaattataa tgtttatgcc acaaactata ctgggtcatg cccagaagag    960
gaagttttga ggaacaatga cctctcttgg ctctggaaca gcagtacagc cctgtatcct   1020
gctgtcagta ttaggaaatc ctttgcagac agtgaaaaca ctttgcactt ctcacgattt   1080
cgggtgcgtg aatcactgag gatttccacc atgacatcac aggattatgc tctgcctgta   1140
tttgtctaca cacagctggg ctacaaagag gaacctttac ttttcccttt taagcaagat   1200
ctaattagta ccataggaga aagtgctgcg ttgggagcgg caggcattgt tgtttgggga   1260
gacatgaatt taacttcatc tgaggagaac tgtacgaaag tgaaccgctt tgtgaattct   1320
gattttggca gctacataat caatgtgacc agagcagctg aggtgtccag tcgtcacctt   1380
tgcaagaata atgggaggtg tgtacggaag acatggaaag cagctcatta cctccatttg   1440
aaccctgcaa gttaccacat agaggcctct gaggatggag aattcatagt gaggggaaga   1500
gcatcagaca ctgacctagc tgtgatggca gagaatttcc tatgtcactg ttatgaggga   1560 tatgagggg ctgactgtag agaaatgaca gaggccagtg gccctcggg gctttccctt     1620 tcctctagct ctgtaataac actgtgtctg ctagttctag caggttatca aagcattcag   1680
ttgtgacata attgacttta aagggaatcg catccttta aaaagggtgt tagggaacag    1740
atagacactc ttctctctta ggagttcctc tgagaggcct tataaatcaa catatgtgtc   1800
acaacataaa tagaacctgt taccttattt gctacacttt gtttagagcc agctttaaaa   1860
gaacaaagca atgcacacca ttttcttact tgagtatttc aattacactt aaattgaatt   1920
```

```
ttattctctt tctaattata taaacaccag tgtatacatg aatactaagt tgttatttc      1980 aagcacattt tctaggtagc agtttaagga ctggttacaa tgtaaccacc tcattcaaca     2040
gatggatcaa ctcagccatg acccagtcaa ctaattcatc agagaaggtg aaatgcaggg    2100
ctactgtgcc agcctcccct tcacttgtat ctgtttccct gatggaggac agggttacta   2160
ccggtatggt ttcttaggaa agagaggtca gggacctggt tccaattcat cgcaaccatc   2220
aacctcttcc ttcatagacc ctaccagttt gcaaaccaca aaaaaggtcc aggattcatt   2280
gagctgtaga tccaaaagct gtagtgatgg tgactttga aagtgaaacc ttttatttaa    2340
tgaaaagtaa gttataagga aaatcagcta ctctgccttc ctctgctgcc catatcattt    2400
tgagtagtat acttggattt agaatccatt tgaacctgat ttaaatcatg ctttccacaa    2460
tttatgtgtg gtataaatct tagcaaattc tttataatcc cctttttcca tctgaaattt    2520
ggtagtataa ttttatctta acaaattagc acaggaattt gctctgcact cctgggttct    2580
tagtgatgta agggatgcag acaatctct tggtcaccaa agagaagtca agctgtttcc    2640
ttccatggcc agggaccatt tatcatcact tagacattgt gttgtggtct tgagcgacac   2700
tctcagggga tacggttttc actccataaa gataatttag tgggaaaaga agctcagaag   2760
tgatatgatg atgctgttaa agaagggcac caccacttga tgtcttctct ttcttaactc   2820
tttcaactca ggatccctgc ttgccagagg tgactgtgaa agcttaattt tgaaatgtac    2880
gatacaaaca aacaaggctt taataatact gtgaatgaaa gttatgttta aatacataga    2940
ttagctattt agaaattaaa ttaatttta tatgaaagta gatgtgatta gcactataga    3000
acatttacac aactttaata ataaccaaag aaatcaccaa caaaccccta ccatatgctg    3060
gtaacttttg gtgtactatt tactaatatt tcttgtaaaa tgatttttgt attattgttg    3120
taattatatt ttatgatctg tgtttcaatt tatgatgtga gtggttttca tatcatttca    3180
taatattcat gcatattatt taaaaatctt tttctcttcc agtagaggga ttaaaggtaa    3240
agatttatac aaacc                                                    3255

<210> SEQ ID NO 5
<211> LENGTH: 1269
<212> TYPE: DNA
<213> ORGANISM: Homo sapiens

<400> SEQUENCE: 5
ctaaaacctg ctcgacttcc aatttatcaa aggaaacctt ttatagctgc ttggaatgct     60
ccaacagatc agtgtttgat aaaatataat ttaagactaa atttgaaaat gtttcctgtg    120
attggaagcc cactggccaa ggccaggggg caaaatgtca ctatatttta tgtcaacaga    180
ttgggatact atccgtggta tacatcacag ggggtcccca ttaatggagg ctctcccacag   240 aacataagtt tacaagtaca tctggaaaaa gctgaccaag atattaatta ttacatccct    300
gctgaagatt tcagtggact tgctgttata gattgggaat attggagacc acagtggggcc    360 cggaactgga actcaaaaga tgtttacaga cagaagtcaa gaaagcttat ttccgatatg    420
ggaaagaatg tatcagctac cgatattgaa tatttagcca aagtgacctt tgaagaaagt    480
gcaaaagctt tcatgaagga aaccatcaaa ttgggaatta gagccgacc caaaggcctt    540 tggggttatt atttatatcc tgattgccac aattataacg tttatgcccc aaactactct    600
gggtcatgcc cagaagacga agtcttgagg acaatgagc tctcttggct ctggaacagc    660
agtgctgctt tatatccttc tatctgtgtc tggaaatccc ttggagacag tgaaaacatt    720
ttgcgcttct ccaaatttcg ggtgcatgaa tccatgagga tctccaccat gacatctcat    780
```

-continued

```
gattatgctc tgcctgtatt tgtctacaca aggctagggt acagagatga acctttattt      840
ttcctttcta agcaagatct agtcagcacc ataggagaaa gtgctgcctt gggagctgca      900
ggcattgtta tttggggaga catgaattta actgcatcca aggccaactg tacaaaggtg      960
aagcagtttg tgagttctga tttagggagc tacatagcca atgtgaccag agctgctgag     1020
gtatgcagcc ttcacctctg caggaacaat ggcaggtgca taaggaagat gtggaacgcg     1080
cccagttacc ttcacttgaa ccctgcaagt taccacatag aggcctctga ggacggggag     1140
tttactgtga aaggaaaagc atctgataca gacctggcag tgatggcaga tacattttcc     1200
tgtcattgtt atcagggata tgaaggagct gattgcagag aaataaagac ggctgatggc     1260
tgctctggg                                                             1269
```

<210> SEQ ID NO 6
<211> LENGTH: 423
<212> TYPE: PRT
<213> ORGANISM: Homo sapiens

<400> SEQUENCE: 6

```
Leu Lys Pro Ala Arg Leu Pro Ile Tyr Gln Arg Lys Pro Phe Ile Ala
1               5                   10                  15

Ala Trp Asn Ala Pro Thr Asp Gln Cys Leu Ile Lys Tyr Asn Leu Arg
            20                  25                  30

Leu Asn Leu Lys Met Phe Pro Val Ile Gly Ser Pro Leu Ala Lys Ala
        35                  40                  45

Arg Gly Gln Asn Val Thr Ile Phe Tyr Val Asn Arg Leu Gly Tyr Tyr
    50                  55                  60

Pro Trp Tyr Thr Ser Gln Gly Val Pro Ile Asn Gly Gly Leu Pro Gln
65                  70                  75                  80

Asn Ile Ser Leu Gln Val His Leu Glu Lys Ala Asp Gln Asp Ile Asn
                85                  90                  95

Tyr Tyr Ile Pro Ala Glu Asp Phe Ser Gly Leu Ala Val Ile Asp Trp
            100                 105                 110

Glu Tyr Trp Arg Pro Gln Trp Ala Arg Asn Trp Asn Ser Lys Asp Val
        115                 120                 125

Tyr Arg Gln Lys Ser Arg Lys Leu Ile Ser Asp Met Gly Lys Asn Val
    130                 135                 140

Ser Ala Thr Asp Ile Glu Tyr Leu Ala Lys Val Thr Phe Glu Glu Ser
145                 150                 155                 160

Ala Lys Ala Phe Met Lys Glu Thr Ile Lys Leu Gly Ile Lys Ser Arg
                165                 170                 175

Pro Lys Gly Leu Trp Gly Tyr Tyr Leu Tyr Pro Asp Cys His Asn Tyr
            180                 185                 190

Asn Val Tyr Ala Pro Asn Tyr Ser Gly Ser Cys Pro Glu Asp Glu Val
        195                 200                 205

Leu Arg Asn Asn Glu Leu Ser Trp Leu Trp Asn Ser Ser Ala Ala Leu
    210                 215                 220

Tyr Pro Ser Ile Cys Val Trp Lys Ser Leu Gly Asp Ser Glu Asn Ile
225                 230                 235                 240

Leu Arg Phe Ser Lys Phe Arg Val His Glu Ser Met Arg Ile Ser Thr
                245                 250                 255

Met Thr Ser His Asp Tyr Ala Leu Pro Val Phe Val Tyr Thr Arg Leu
            260                 265                 270

Gly Tyr Arg Asp Glu Pro Leu Phe Phe Leu Ser Lys Gln Asp Leu Val
```

```
                275                 280                 285
Ser Thr Ile Gly Glu Ser Ala Ala Leu Gly Ala Ala Gly Ile Val Ile
    290                 295                 300

Trp Gly Asp Met Asn Leu Thr Ala Ser Lys Ala Asn Cys Thr Lys Val
305                 310                 315                 320

Lys Gln Phe Val Ser Ser Asp Leu Gly Ser Tyr Ile Ala Asn Val Thr
                325                 330                 335

Arg Ala Ala Glu Val Cys Ser Leu His Leu Cys Arg Asn Asn Gly Arg
            340                 345                 350

Cys Ile Arg Lys Met Trp Asn Ala Pro Ser Tyr Leu His Leu Asn Pro
        355                 360                 365

Ala Ser Tyr His Ile Glu Ala Ser Glu Asp Gly Glu Phe Thr Val Lys
    370                 375                 380

Gly Lys Ala Ser Asp Thr Asp Leu Ala Val Met Ala Asp Thr Phe Ser
385                 390                 395                 400

Cys His Cys Tyr Gln Gly Tyr Glu Gly Ala Asp Cys Arg Glu Ile Lys
                405                 410                 415

Thr Ala Asp Gly Cys Ser Gly
            420

<210> SEQ ID NO 7
<211> LENGTH: 34
<212> TYPE: DNA
<213> ORGANISM: Artificial Sequence
<220> FEATURE:
<223> OTHER INFORMATION: NHECHASEGP Forward Primer

<400> SEQUENCE: 7
ggccgctagc atgaaagtat tatctgaagg acag                              34

<210> SEQ ID NO 8
<211> LENGTH: 29
<212> TYPE: DNA
<213> ORGANISM: Artificial Sequence
<220> FEATURE:
<223> OTHER INFORMATION: BAMH1CHASEGP Reverse Primer

<400> SEQUENCE: 8
ggaatggatc ctcacaactg aatgcttcg                                    29

<210> SEQ ID NO 9
<211> LENGTH: 28
<212> TYPE: DNA
<213> ORGANISM: Artificial Sequence
<220> FEATURE:
<223> OTHER INFORMATION: CHASEGPSTOPBAMH1 Reverse Primer

<400> SEQUENCE: 9
aattggatcc tcacccagag cagccatc                                     28

<210> SEQ ID NO 10
<211> LENGTH: 27
<212> TYPE: DNA
<213> ORGANISM: Artificial Sequence
<220> FEATURE:
<223> OTHER INFORMATION: CHASEGP455STOP BAMH1 Reverse Primer

<400> SEQUENCE: 10
aattggatcc tcagcagcca tcagccg                                      27
```